US009984522B2

(12) United States Patent
Ricci

(10) Patent No.: US 9,984,522 B2
(45) Date of Patent: May 29, 2018

(54) VEHICLE IDENTIFICATION OR AUTHENTICATION

(71) Applicant: NIO USA, Inc., San Jose, CA (US)

(72) Inventor: Christopher P. Ricci, Saratoga, CA (US)

(73) Assignee: NIO USA, Inc., San Jose, CA (US)

( * ) Notice: Subject to any disclaimer, the term of this patent is extended or adjusted under 35 U.S.C. 154(b) by 0 days. days.

(21) Appl. No.: 15/339,599

(22) Filed: Oct. 31, 2016

(65) Prior Publication Data
US 2018/0012433 A1     Jan. 11, 2018

Related U.S. Application Data

(60) Provisional application No. 62/359,563, filed on Jul. 7, 2016, provisional application No. 62/378,348, filed on Aug. 23, 2016.

(51) Int. Cl.
*G07C 9/00* (2006.01)
*G07C 5/00* (2006.01)
(Continued)

(52) U.S. Cl.
CPC ........ *G07C 9/00563* (2013.01); *A61B 5/1171* (2016.02); *A61B 5/1172* (2013.01);
(Continued)

(58) Field of Classification Search
CPC .......... G06F 21/32; G06F 21/34; G06F 21/35; G06F 21/83; G06F 21/31; G06F 21/36; G06F 21/606; G06F 21/6245; G06F 21/88
(Continued)

(56) References Cited

U.S. PATENT DOCUMENTS 4,361,202 A    11/1982  Minovitch
4,476,954 A    10/1984  Johnson et al.
(Continued)

FOREIGN PATENT DOCUMENTS

CN     1417755     5/2003
CN     1847817     10/2006
(Continued)

OTHER PUBLICATIONS

"Multi-factor authentication," Wikipedia, retrieved from https://en.wikipedia.org/wiki/Multi-factor_authentication, retrieved on Dec. 9, 2016, 6 pages.
(Continued)

*Primary Examiner* — Mark Blouin
(74) *Attorney, Agent, or Firm* — Sheridan Ross P.C.

(57) ABSTRACT

A vehicle includes an on board microprocessor that is programmed to receive and transmit multiple authentication factors or a key derived therefrom to a remote server to authenticate the vehicle or a vehicle occupant to a remote server. The multiple authentication factors comprise a plurality of an electronic address of a portable communication device of the occupant sensed by an on board sensor, a wireless remote signal description sensed by an on board sensor, a vehicle-related identifier, a vehicle parameter sensed by the on board processor, an environmental parameter sensed by the on board processor, and a passcode received by the microprocessor from the remote server.

24 Claims, 27 Drawing Sheets

(51) Int. Cl.
  *G07C 5/08* (2006.01)
  *G07C 5/02* (2006.01)
  *A61B 5/1171* (2016.01)
  *A61B 5/1172* (2016.01)
  *B60L 11/18* (2006.01)
  *B60M 1/00* (2006.01)
  *B60K 6/20* (2007.10)

(52) U.S. Cl.
  CPC ............ *A61B 5/1176* (2013.01); *G07C 5/008* (2013.01); *G07C 5/02* (2013.01); *G07C 5/0858* (2013.01); *B60K 6/20* (2013.01); *B60L 11/182* (2013.01); *B60L 11/1827* (2013.01); *B60M 1/00* (2013.01); *B60Y 2200/91* (2013.01); *B60Y 2200/912* (2013.01); *B60Y 2200/92* (2013.01)

(58) Field of Classification Search
  USPC ...................................................... 340/5.53
  See application file for complete search history.

(56) References Cited

U.S. PATENT DOCUMENTS

| | | | |
|---|---|---|---|
| 4,754,255 A | 6/1988 | Sanders et al. | |
| 4,875,391 A | 10/1989 | Leising et al. | |
| 5,136,498 A | 8/1992 | McLaughlin et al. | |
| 5,204,817 A | 4/1993 | Yoshida | |
| 5,363,306 A | 11/1994 | Kuwahara et al. | |
| 5,508,689 A | 4/1996 | Rado et al. | |
| 5,521,815 A | 5/1996 | Rose | |
| 5,529,138 A | 6/1996 | Shaw et al. | |
| 5,531,122 A | 7/1996 | Chatham et al. | |
| 5,572,450 A | 11/1996 | Worthy | |
| 5,610,821 A | 3/1997 | Gazis et al. | |
| 5,648,769 A | 7/1997 | Sato et al. | |
| 5,710,702 A | 1/1998 | Hayashi et al. | |
| 5,794,164 A | 8/1998 | Beckert et al. | |
| 5,797,134 A | 8/1998 | McMillan et al. | |
| 5,808,372 A | 9/1998 | Schwegler et al. | |
| 5,812,067 A | 9/1998 | Bergholz et al. | |
| 5,825,283 A | 10/1998 | Camhi | |
| 5,838,251 A | 11/1998 | Brinkmeyer et al. | |
| 5,847,661 A | 12/1998 | Ricci | |
| 5,890,080 A | 3/1999 | Coverdill et al. | |
| 5,928,294 A | 7/1999 | Zelinkovsky | |
| 5,949,345 A | 9/1999 | Beckert et al. | |
| 5,983,161 A | 11/1999 | Lemelson et al. | |
| 5,986,575 A | 11/1999 | Jones et al. | |
| 6,038,426 A | 3/2000 | Williams, Jr. | |
| 6,081,756 A | 6/2000 | Mio et al. | |
| D429,684 S | 8/2000 | Johnson | |
| 6,128,003 A | 10/2000 | Smith et al. | |
| 6,141,620 A | 10/2000 | Zyburt et al. | |
| 6,148,261 A | 11/2000 | Obradovich et al. | |
| 6,152,514 A | 11/2000 | McLellen | |
| 6,157,321 A | 12/2000 | Ricci | |
| 6,191,703 B1 | 2/2001 | Wallace | |
| 6,198,996 B1 | 3/2001 | Berstis | |
| 6,199,001 B1 | 3/2001 | Ohta et al. | |
| 6,202,008 B1 | 3/2001 | Beckert et al. | |
| 6,252,544 B1 | 6/2001 | Hoffberg | |
| 6,267,428 B1 | 7/2001 | Baldas et al. | |
| 6,302,438 B1 | 10/2001 | Stopper, Jr. et al. | |
| 6,310,542 B1 | 10/2001 | Gehlot | |
| 6,317,058 B1 | 11/2001 | Lemelson et al. | |
| 6,339,826 B2 | 1/2002 | Hayes, Jr. et al. | |
| 6,356,838 B1 | 3/2002 | Paul | |
| 6,388,579 B1 | 5/2002 | Adcox et al. | |
| 6,445,084 B1 | 9/2002 | Daiss et al. | |
| 6,480,224 B1 | 11/2002 | Brown | |
| 6,496,100 B1 | 12/2002 | Hiebl | |
| 6,502,022 B1 | 12/2002 | Chastain et al. | |
| 6,519,519 B1 | 2/2003 | Stopczynski | |
| 6,542,071 B1 | 4/2003 | Ohtsubo et al. | |
| 6,557,752 B1 | 5/2003 | Yacoob | |
| 6,563,910 B2 | 5/2003 | Menard et al. | |
| 6,587,739 B1 | 7/2003 | Abrams et al. | |
| 6,598,227 B1 | 7/2003 | Berry et al. | |
| 6,607,212 B1 | 8/2003 | Reimer et al. | |
| 6,617,981 B2 | 9/2003 | Basinger | |
| 6,662,077 B2 | 12/2003 | Haag | |
| 6,675,081 B2 | 1/2004 | Shuman et al. | |
| 6,678,747 B2 | 1/2004 | Goossen et al. | |
| 6,681,176 B2 | 1/2004 | Funk et al. | |
| 6,690,260 B1 | 2/2004 | Ashihara | |
| 6,690,940 B1 | 2/2004 | Brown et al. | |
| 6,724,920 B1 | 4/2004 | Berenz et al. | |
| 6,754,580 B1 | 6/2004 | Ask et al. | |
| 6,757,593 B2 | 6/2004 | Mori et al. | |
| 6,762,684 B1 | 7/2004 | Camhi | |
| 6,765,495 B1 | 7/2004 | Dunning et al. | |
| 6,778,888 B2 | 8/2004 | Cataldo et al. | |
| 6,782,240 B1 | 8/2004 | Tabe | |
| 6,785,531 B2 | 8/2004 | Lepley et al. | |
| 6,816,783 B2 | 11/2004 | Hashima et al. | |
| 6,820,259 B1 | 11/2004 | Kawamata et al. | |
| 6,944,533 B2 | 9/2005 | Obradovich et al. | |
| 6,950,022 B2 | 9/2005 | Breed | |
| 6,952,156 B2 | 10/2005 | Arshad et al. | |
| 6,958,707 B1 | 10/2005 | Siegel | |
| 6,965,816 B2 * | 11/2005 | Walker | B64C 13/20 244/189 |
| 6,992,580 B2 | 1/2006 | Kotzin et al. | |
| 7,019,641 B1 | 3/2006 | Lakshmanan et al. | |
| 7,020,544 B2 | 3/2006 | Shinada et al. | |
| 7,021,691 B1 | 4/2006 | Schmidt et al. | |
| 7,042,345 B2 | 5/2006 | Ellis | |
| 7,047,129 B2 | 5/2006 | Uotani | |
| 7,058,898 B2 | 6/2006 | McWalter et al. | |
| 7,096,431 B2 | 8/2006 | Tambata et al. | |
| 7,142,696 B1 | 11/2006 | Engelsberg et al. | |
| 7,164,117 B2 | 1/2007 | Breed et al. | |
| 7,187,947 B1 | 3/2007 | White et al. | |
| 7,203,598 B1 | 4/2007 | Whitsell | |
| 7,233,861 B2 | 6/2007 | Van Buer et al. | |
| 7,239,960 B2 | 7/2007 | Yokota et al. | |
| 7,277,454 B2 | 10/2007 | Mocek et al. | |
| 7,284,769 B2 | 10/2007 | Breed | |
| 7,289,645 B2 | 10/2007 | Yamamoto et al. | |
| 7,295,921 B2 | 11/2007 | Spencer et al. | |
| 7,313,547 B2 | 12/2007 | Mocek et al. | |
| 7,333,012 B1 | 2/2008 | Nguyen | |
| 7,343,148 B1 | 3/2008 | O'Neil | |
| 7,386,376 B2 | 6/2008 | Basir et al. | |
| 7,386,799 B1 | 6/2008 | Clanton et al. | |
| 7,432,829 B2 | 10/2008 | Poltorak | |
| 7,474,264 B2 | 1/2009 | Bolduc et al. | |
| 7,493,140 B2 | 2/2009 | Michmerhuizen et al. | |
| 7,526,539 B1 | 4/2009 | Hsu | |
| 7,548,815 B2 | 6/2009 | Watkins et al. | |
| 7,566,083 B2 | 7/2009 | Vitito | |
| 7,606,660 B2 | 10/2009 | Diaz et al. | |
| 7,606,867 B1 | 10/2009 | Singhal et al. | |
| 7,643,913 B2 | 1/2010 | Taki et al. | |
| 7,650,234 B2 | 1/2010 | Obradovich et al. | |
| 7,671,764 B2 | 3/2010 | Uyeki et al. | |
| 7,680,596 B2 | 3/2010 | Uyeki et al. | |
| 7,683,771 B1 | 3/2010 | Loeb | |
| 7,711,468 B1 | 5/2010 | Levy | |
| 7,734,315 B2 | 6/2010 | Rathus et al. | |
| 7,748,021 B2 | 6/2010 | Obradovich et al. | |
| RE41,449 E | 7/2010 | Krahnstoever et al. | |
| 7,791,499 B2 | 9/2010 | Mohan et al. | |
| 7,796,190 B2 | 9/2010 | Basso et al. | |
| 7,802,832 B2 | 9/2010 | Carnevali | |
| 7,821,421 B2 | 10/2010 | Tamir et al. | |
| 7,832,762 B2 | 11/2010 | Breed | |
| 7,864,073 B2 | 1/2011 | Lee et al. | |
| 7,864,987 B2 | 1/2011 | Venkatanna et al. | |
| 7,872,591 B2 | 1/2011 | Kane et al. | |
| 7,873,471 B2 | 1/2011 | Gieseke | |
| 7,881,703 B2 | 2/2011 | Roundtree et al. | |
| 7,891,004 B1 | 2/2011 | Gelvin et al. | |

(56) References Cited

U.S. PATENT DOCUMENTS

| | | |
|---|---|---|
| 7,891,719 B2 | 2/2011 | Carnevali |
| 7,899,610 B2 | 3/2011 | McClellan |
| 7,966,678 B2 | 6/2011 | Ten Eyck et al. |
| 7,969,290 B2 | 6/2011 | Waeller et al. |
| 7,969,324 B2 | 6/2011 | Chevion et al. |
| 8,060,631 B2 | 11/2011 | Collart et al. |
| 8,064,925 B1 | 11/2011 | Sun et al. |
| 8,066,313 B2 | 11/2011 | Carnevali |
| 8,098,170 B1 | 1/2012 | Szczerba et al. |
| 8,113,564 B2 | 2/2012 | Carnevali |
| 8,131,419 B2 | 3/2012 | Ampunan et al. |
| 8,157,310 B2 | 4/2012 | Carnevali |
| 8,162,368 B2 | 4/2012 | Carnevali |
| 8,175,802 B2 | 5/2012 | Forstall et al. |
| 8,233,919 B2 | 7/2012 | Haag et al. |
| 8,245,609 B1 | 8/2012 | Greenwald et al. |
| 8,306,514 B1 | 11/2012 | Nunally |
| 8,334,847 B2 | 12/2012 | Tomkins |
| 8,346,233 B2 | 1/2013 | Aaron et al. |
| 8,346,432 B2 | 1/2013 | Van Wiemeersch et al. |
| 8,350,721 B2 | 1/2013 | Carr |
| 8,352,282 B2 | 1/2013 | Jensen et al. |
| 8,369,263 B2 | 2/2013 | Dowling et al. |
| 8,417,449 B1 | 4/2013 | Denise |
| 8,432,260 B2 | 4/2013 | Talty et al. |
| 8,442,389 B2 | 5/2013 | Kashima et al. |
| 8,442,758 B1 | 5/2013 | Rovik et al. |
| 8,467,965 B2 | 6/2013 | Chang |
| 8,497,842 B2 | 7/2013 | Tomkins et al. |
| 8,498,809 B2 | 7/2013 | Bill |
| 8,509,982 B2 | 8/2013 | Montemerlo et al. |
| 8,521,410 B2 | 8/2013 | Mizuno et al. |
| 8,527,143 B2 | 9/2013 | Tan |
| 8,527,146 B1 | 9/2013 | Jackson et al. |
| 8,532,574 B2 | 9/2013 | Kirsch |
| 8,543,330 B2 | 9/2013 | Taylor et al. |
| 8,547,340 B2 | 10/2013 | Sizelove et al. |
| 8,548,669 B2 | 10/2013 | Naylor |
| 8,559,183 B1 | 10/2013 | Davis |
| 8,577,600 B1 | 11/2013 | Pierfelice |
| 8,578,279 B2 | 11/2013 | Chen et al. |
| 8,583,292 B2 | 11/2013 | Preston et al. |
| 8,589,073 B2 | 11/2013 | Guha et al. |
| 8,600,611 B2 | 12/2013 | Seize |
| 8,613,385 B1 | 12/2013 | Hulet et al. |
| 8,621,645 B1 | 12/2013 | Spackman |
| 8,624,727 B2 | 1/2014 | Saigh et al. |
| 8,634,984 B2 | 1/2014 | Sumizawa |
| 8,644,165 B2 | 2/2014 | Saarimaki et al. |
| 8,660,735 B2 | 2/2014 | Tengler et al. |
| 8,671,068 B2 | 3/2014 | Harber et al. |
| 8,688,372 B2 | 4/2014 | Bhogal et al. |
| 8,705,527 B1 | 4/2014 | Addepalli et al. |
| 8,706,143 B1 | 4/2014 | Elias |
| 8,718,797 B1 | 5/2014 | Addepalli et al. |
| 8,725,311 B1 | 5/2014 | Breed |
| 8,730,033 B2 | 5/2014 | Yarnold et al. |
| 8,737,986 B2 | 5/2014 | Rhoads et al. |
| 8,761,673 B2 | 6/2014 | Sakata |
| 8,774,842 B2 | 7/2014 | Jones et al. |
| 8,779,947 B2 | 7/2014 | Tengler et al. |
| 8,782,262 B2 | 7/2014 | Collart et al. |
| 8,793,065 B2 | 7/2014 | Seltzer et al. |
| 8,798,918 B2 | 8/2014 | Onishi et al. |
| 8,799,657 B2 | 8/2014 | Bhattacharya et al. |
| 8,805,110 B2 | 8/2014 | Rhoads et al. |
| 8,812,171 B2 | 8/2014 | Filev et al. |
| 8,817,761 B2 | 8/2014 | Gruberman et al. |
| 8,825,031 B2 | 9/2014 | Aaron et al. |
| 8,825,277 B2 | 9/2014 | McClellan et al. |
| 8,825,382 B2 | 9/2014 | Liu |
| 8,826,261 B1 | 9/2014 | Ag et al. |
| 8,838,088 B1 | 9/2014 | Henn et al. |
| 8,862,317 B2 | 10/2014 | Shin et al. |
| 8,977,408 B1 | 3/2015 | Cazanas et al. |
| 8,989,053 B1 * | 3/2015 | Skaaksrud ............ H04W 12/06 370/255 |
| 9,043,016 B2 | 5/2015 | Filippov et al. |
| 9,229,905 B1 | 1/2016 | Penilla et al. |
| 9,501,666 B2 | 11/2016 | Lockett et al. |
| 2001/0010516 A1 | 8/2001 | Roh et al. |
| 2001/0015888 A1 | 8/2001 | Shaler et al. |
| 2002/0009978 A1 | 1/2002 | Dukach et al. |
| 2002/0023010 A1 | 2/2002 | Rittmaster et al. |
| 2002/0026278 A1 | 2/2002 | Feldman et al. |
| 2002/0045484 A1 | 4/2002 | Eck et al. |
| 2002/0065046 A1 | 5/2002 | Mankins et al. |
| 2002/0077985 A1 | 6/2002 | Kobata et al. |
| 2002/0095249 A1 | 7/2002 | Lang |
| 2002/0097145 A1 | 7/2002 | Tumey et al. |
| 2002/0103622 A1 | 8/2002 | Burge |
| 2002/0105968 A1 | 8/2002 | Pruzan et al. |
| 2002/0126876 A1 | 9/2002 | Paul et al. |
| 2002/0128774 A1 | 9/2002 | Takezaki et al. |
| 2002/0143461 A1 | 10/2002 | Burns et al. |
| 2002/0143643 A1 | 10/2002 | Catan |
| 2002/0152010 A1 | 10/2002 | Colmenarez et al. |
| 2002/0154217 A1 | 10/2002 | Ikeda |
| 2002/0169551 A1 | 11/2002 | Inoue et al. |
| 2002/0174021 A1 | 11/2002 | Chu et al. |
| 2003/0004624 A1 | 1/2003 | Wilson et al. |
| 2003/0007227 A1 | 1/2003 | Ogino |
| 2003/0055557 A1 | 3/2003 | Dutta et al. |
| 2003/0060937 A1 | 3/2003 | Shinada et al. |
| 2003/0065432 A1 | 4/2003 | Shuman et al. |
| 2003/0101451 A1 | 5/2003 | Bentolila et al. |
| 2003/0109972 A1 | 6/2003 | Tak |
| 2003/0125846 A1 | 7/2003 | Yu et al. |
| 2003/0132666 A1 | 7/2003 | Bond et al. |
| 2003/0149530 A1 | 8/2003 | Stopczynski |
| 2003/0158638 A1 | 8/2003 | Yakes et al. |
| 2003/0182435 A1 | 9/2003 | Redlich et al. |
| 2003/0202683 A1 | 10/2003 | Ma et al. |
| 2003/0204290 A1 | 10/2003 | Sadler et al. |
| 2003/0229492 A1 | 12/2003 | Nolan |
| 2003/0230443 A1 | 12/2003 | Cramer et al. |
| 2004/0017292 A1 | 1/2004 | Reese et al. |
| 2004/0024502 A1 | 2/2004 | Squires et al. |
| 2004/0036622 A1 | 2/2004 | Dukach et al. |
| 2004/0039500 A1 | 2/2004 | Amendola et al. |
| 2004/0039504 A1 | 2/2004 | Coffee et al. |
| 2004/0068364 A1 | 4/2004 | Zhao et al. |
| 2004/0070920 A1 | 4/2004 | Flueli |
| 2004/0093155 A1 | 5/2004 | Simonds et al. |
| 2004/0117494 A1 | 6/2004 | Mitchell et al. |
| 2004/0128062 A1 | 7/2004 | Ogino et al. |
| 2004/0143438 A1 | 7/2004 | Cabezas et al. |
| 2004/0153356 A1 | 8/2004 | Lockwood et al. |
| 2004/0162019 A1 | 8/2004 | Horita et al. |
| 2004/0180653 A1 | 9/2004 | Royalty |
| 2004/0182574 A1 | 9/2004 | Adnan et al. |
| 2004/0193347 A1 | 9/2004 | Harumoto et al. |
| 2004/0203974 A1 | 10/2004 | Seibel |
| 2004/0204837 A1 | 10/2004 | Singleton |
| 2004/0209594 A1 | 10/2004 | Naboulsi |
| 2004/0217850 A1 | 11/2004 | Perttunen et al. |
| 2004/0225557 A1 | 11/2004 | Phelan et al. |
| 2004/0255123 A1 | 12/2004 | Noyama et al. |
| 2004/0257208 A1 | 12/2004 | Huang et al. |
| 2004/0260470 A1 | 12/2004 | Rast |
| 2005/0012599 A1 | 1/2005 | DeMatteo |
| 2005/0031100 A1 | 2/2005 | Iggulden et al. |
| 2005/0038598 A1 | 2/2005 | Oesterling et al. |
| 2005/0042999 A1 | 2/2005 | Rappaport |
| 2005/0065678 A1 | 3/2005 | Smith et al. |
| 2005/0065711 A1 | 3/2005 | Dahlgren et al. |
| 2005/0086051 A1 | 4/2005 | Brulle-Drews |
| 2005/0093717 A1 | 5/2005 | Lilja |
| 2005/0096906 A1 | 5/2005 | Barzilay |
| 2005/0097541 A1 | 5/2005 | Holland |
| 2005/0114864 A1 | 5/2005 | Surace |
| 2005/0122235 A1 | 6/2005 | Teffer et al. |
| 2005/0124211 A1 | 6/2005 | Diessner et al. |
| 2005/0130744 A1 | 6/2005 | Eck et al. |

(56) References Cited

U.S. PATENT DOCUMENTS

| | | |
|---|---|---|
| 2005/0144156 A1 | 6/2005 | Barber |
| 2005/0149752 A1 | 7/2005 | Johnson et al. |
| 2005/0153760 A1 | 7/2005 | Varley |
| 2005/0159853 A1 | 7/2005 | Takahashi et al. |
| 2005/0159892 A1 | 7/2005 | Chung |
| 2005/0192727 A1 | 9/2005 | Shostak et al. |
| 2005/0197748 A1 | 9/2005 | Holst et al. |
| 2005/0197767 A1 | 9/2005 | Nortrup |
| 2005/0251324 A1 | 11/2005 | Wiener et al. |
| 2005/0261815 A1 | 11/2005 | Cowelchuk et al. |
| 2005/0278093 A1 | 12/2005 | Kameyama |
| 2005/0283284 A1 | 12/2005 | Grenier et al. |
| 2006/0015819 A1 | 1/2006 | Hawkins et al. |
| 2006/0036358 A1 | 2/2006 | Hale et al. |
| 2006/0044119 A1 | 3/2006 | Egelhaaf |
| 2006/0047386 A1 | 3/2006 | Kanevsky et al. |
| 2006/0058948 A1 | 3/2006 | Blass et al. |
| 2006/0059229 A1 | 3/2006 | Bain et al. |
| 2006/0125631 A1 | 6/2006 | Sharony |
| 2006/0130033 A1 | 6/2006 | Stoffels et al. |
| 2006/0142933 A1 | 6/2006 | Feng |
| 2006/0173841 A1 | 8/2006 | Bill |
| 2006/0175403 A1 | 8/2006 | McConnell et al. |
| 2006/0184319 A1 | 8/2006 | Seick et al. |
| 2006/0212909 A1 | 9/2006 | Girard et al. |
| 2006/0241836 A1 | 10/2006 | Kachouh et al. |
| 2006/0243056 A1 | 11/2006 | Sundermeyer et al. |
| 2006/0250272 A1 | 11/2006 | Puamau |
| 2006/0253307 A1 | 11/2006 | Warren et al. |
| 2006/0259210 A1 | 11/2006 | Tanaka et al. |
| 2006/0259304 A1 | 11/2006 | Barzilay |
| 2006/0274829 A1 | 12/2006 | Siemens et al. |
| 2006/0282204 A1 | 12/2006 | Breed |
| 2006/0286969 A1 | 12/2006 | Talmor et al. |
| 2006/0287807 A1 | 12/2006 | Teffer |
| 2006/0287865 A1 | 12/2006 | Cross et al. |
| 2006/0288382 A1 | 12/2006 | Vitito |
| 2006/0290516 A1 | 12/2006 | Muehlsteff et al. |
| 2007/0001831 A1 | 1/2007 | Raz et al. |
| 2007/0002032 A1 | 1/2007 | Powers et al. |
| 2007/0010942 A1 | 1/2007 | Bill |
| 2007/0015485 A1 | 1/2007 | DeBiasio et al. |
| 2007/0028370 A1 | 2/2007 | Seng |
| 2007/0032225 A1 | 2/2007 | Konicek et al. |
| 2007/0057781 A1 | 3/2007 | Breed |
| 2007/0061057 A1 | 3/2007 | Huang et al. |
| 2007/0067614 A1 | 3/2007 | Berry et al. |
| 2007/0069880 A1 | 3/2007 | Best et al. |
| 2007/0083298 A1 | 4/2007 | Pierce et al. |
| 2007/0088488 A1 | 4/2007 | Reeves et al. |
| 2007/0103328 A1 | 5/2007 | Lakshmanan et al. |
| 2007/0115101 A1 | 5/2007 | Creekbaum et al. |
| 2007/0118301 A1 | 5/2007 | Andarawis et al. |
| 2007/0120697 A1 | 5/2007 | Ayoub et al. |
| 2007/0135995 A1 | 6/2007 | Kikuchi et al. |
| 2007/0156317 A1 | 7/2007 | Breed |
| 2007/0182625 A1 | 8/2007 | Kerai et al. |
| 2007/0182816 A1 | 8/2007 | Fox |
| 2007/0185969 A1 | 8/2007 | Davis |
| 2007/0192486 A1 | 8/2007 | Wilson et al. |
| 2007/0194902 A1 | 8/2007 | Blanco et al. |
| 2007/0194944 A1 | 8/2007 | Galera et al. |
| 2007/0195997 A1 | 8/2007 | Paul et al. |
| 2007/0200663 A1 | 8/2007 | White et al. |
| 2007/0208860 A1 | 9/2007 | Zellner et al. |
| 2007/0213090 A1 | 9/2007 | Holmberg |
| 2007/0228826 A1 | 10/2007 | Jordan et al. |
| 2007/0233341 A1 | 10/2007 | Logsdon |
| 2007/0250228 A1 | 10/2007 | Reddy et al. |
| 2007/0257815 A1 | 11/2007 | Gunderson et al. |
| 2007/0276596 A1 | 11/2007 | Solomon et al. |
| 2007/0280505 A1 | 12/2007 | Breed |
| 2008/0005974 A1 | 1/2008 | Vazquez et al. |
| 2008/0023253 A1 | 1/2008 | Prost-Fin et al. |
| 2008/0027337 A1 | 1/2008 | Dugan et al. |
| 2008/0033635 A1 | 2/2008 | Obradovich et al. |
| 2008/0042824 A1 | 2/2008 | Kates |
| 2008/0051957 A1 | 2/2008 | Breed et al. |
| 2008/0052627 A1 | 2/2008 | Oguchi |
| 2008/0071465 A1 | 3/2008 | Chapman et al. |
| 2008/0082237 A1 | 4/2008 | Breed |
| 2008/0086455 A1 | 4/2008 | Meisels et al. |
| 2008/0090522 A1 | 4/2008 | Oyama |
| 2008/0104227 A1 | 5/2008 | Birnie et al. |
| 2008/0119994 A1 | 5/2008 | Kameyama |
| 2008/0129475 A1 | 6/2008 | Breed et al. |
| 2008/0143085 A1 | 6/2008 | Breed et al. |
| 2008/0147280 A1 | 6/2008 | Breed |
| 2008/0148374 A1 | 6/2008 | Spaur et al. |
| 2008/0154712 A1 | 6/2008 | Wellman |
| 2008/0154957 A1 | 6/2008 | Taylor et al. |
| 2008/0161986 A1 | 7/2008 | Breed |
| 2008/0164985 A1 | 7/2008 | Iketani et al. |
| 2008/0169940 A1 | 7/2008 | Lee et al. |
| 2008/0174451 A1 | 7/2008 | Harrington et al. |
| 2008/0212215 A1 | 9/2008 | Schofield et al. |
| 2008/0216067 A1 | 9/2008 | Villing |
| 2008/0228358 A1 | 9/2008 | Wang et al. |
| 2008/0234919 A1 | 9/2008 | Ritter et al. |
| 2008/0252487 A1 | 10/2008 | McClellan et al. |
| 2008/0253613 A1 | 10/2008 | Jones et al. |
| 2008/0255721 A1 | 10/2008 | Yamada |
| 2008/0255722 A1 | 10/2008 | McClellan et al. |
| 2008/0269958 A1 | 10/2008 | Filev et al. |
| 2008/0281508 A1 | 11/2008 | Fu |
| 2008/0300778 A1 | 12/2008 | Kuznetsov |
| 2008/0305780 A1 | 12/2008 | Williams et al. |
| 2008/0319602 A1 | 12/2008 | McClellan et al. |
| 2009/0006525 A1 | 1/2009 | Moore |
| 2009/0024419 A1 | 1/2009 | McClellan et al. |
| 2009/0037719 A1 | 2/2009 | Sakthikumar et al. |
| 2009/0040026 A1 | 2/2009 | Tanaka |
| 2009/0055178 A1 | 2/2009 | Coon |
| 2009/0082951 A1 | 3/2009 | Graessley |
| 2009/0099720 A1 | 4/2009 | Elgali |
| 2009/0112393 A1 | 4/2009 | Maten et al. |
| 2009/0112452 A1 | 4/2009 | Buck et al. |
| 2009/0119657 A1 | 5/2009 | Link, II |
| 2009/0125174 A1 | 5/2009 | Delean |
| 2009/0132294 A1 | 5/2009 | Haines |
| 2009/0138336 A1 | 5/2009 | Ashley et al. |
| 2009/0144622 A1 | 6/2009 | Evans et al. |
| 2009/0157312 A1 | 6/2009 | Black et al. |
| 2009/0158200 A1 | 6/2009 | Palahnuk et al. |
| 2009/0180668 A1 | 7/2009 | Jones et al. |
| 2009/0189373 A1 | 7/2009 | Schramm et al. |
| 2009/0189979 A1 | 7/2009 | Smyth |
| 2009/0195370 A1 | 8/2009 | Huffman et al. |
| 2009/0210257 A1 | 8/2009 | Chalfant et al. |
| 2009/0216935 A1 | 8/2009 | Flick |
| 2009/0222200 A1 | 9/2009 | Link et al. |
| 2009/0224931 A1 | 9/2009 | Dietz et al. |
| 2009/0224942 A1 | 9/2009 | Goudy et al. |
| 2009/0234578 A1 | 9/2009 | Newby et al. |
| 2009/0241883 A1 | 10/2009 | Nagoshi et al. |
| 2009/0254446 A1 | 10/2009 | Chernyak |
| 2009/0264849 A1 | 10/2009 | La Croix |
| 2009/0275321 A1 | 11/2009 | Crowe |
| 2009/0278750 A1 | 11/2009 | Man et al. |
| 2009/0278915 A1 | 11/2009 | Kramer et al. |
| 2009/0279839 A1 | 11/2009 | Nakamura et al. |
| 2009/0284359 A1 | 11/2009 | Huang et al. |
| 2009/0287405 A1 | 11/2009 | Liu et al. |
| 2009/0299572 A1 | 12/2009 | Fujikawa et al. |
| 2009/0312998 A1 | 12/2009 | Berckmans et al. |
| 2009/0319181 A1 | 12/2009 | Khosravy et al. |
| 2010/0008053 A1 | 1/2010 | Osternack et al. |
| 2010/0023204 A1 | 1/2010 | Basir et al. |
| 2010/0035620 A1 | 2/2010 | Naden et al. |
| 2010/0036560 A1 | 2/2010 | Wright et al. |
| 2010/0042498 A1 | 2/2010 | Schalk |
| 2010/0052945 A1 | 3/2010 | Breed |
| 2010/0057337 A1 | 3/2010 | Fuchs |
| 2010/0066498 A1 | 3/2010 | Fenton |

(56) References Cited

U.S. PATENT DOCUMENTS

| | | |
|---|---|---|
| 2010/0069115 A1 | 3/2010 | Liu |
| 2010/0070338 A1 | 3/2010 | Siotia et al. |
| 2010/0077094 A1 | 3/2010 | Howarter et al. |
| 2010/0087987 A1 | 4/2010 | Huang et al. |
| 2010/0090817 A1 | 4/2010 | Yamaguchi et al. |
| 2010/0097178 A1 | 4/2010 | Pisz et al. |
| 2010/0097239 A1 | 4/2010 | Campbell et al. |
| 2010/0097458 A1 | 4/2010 | Zhang et al. |
| 2010/0106344 A1 | 4/2010 | Edwards et al. |
| 2010/0106418 A1 | 4/2010 | Kindo et al. |
| 2010/0118025 A1 | 5/2010 | Smith et al. |
| 2010/0121570 A1 | 5/2010 | Tokue et al. |
| 2010/0121645 A1 | 5/2010 | Seitz et al. |
| 2010/0125387 A1 | 5/2010 | Sehyun et al. |
| 2010/0125405 A1 | 5/2010 | Chae et al. |
| 2010/0125811 A1 | 5/2010 | Moore et al. |
| 2010/0127847 A1 | 5/2010 | Evans et al. |
| 2010/0131300 A1 | 5/2010 | Collopy et al. |
| 2010/0134958 A1 | 6/2010 | Disaverio et al. |
| 2010/0136944 A1 | 6/2010 | Taylor et al. |
| 2010/0137037 A1 | 6/2010 | Basir |
| 2010/0144284 A1 | 6/2010 | Chutorash et al. |
| 2010/0145700 A1 | 6/2010 | Kennewick et al. |
| 2010/0145987 A1 | 6/2010 | Harper et al. |
| 2010/0152976 A1 | 6/2010 | White et al. |
| 2010/0169432 A1 | 7/2010 | Santori et al. |
| 2010/0174474 A1 | 7/2010 | Nagase |
| 2010/0179712 A1 | 7/2010 | Pepitone et al. |
| 2010/0185341 A1 | 7/2010 | Wilson et al. |
| 2010/0188831 A1 | 7/2010 | Ortel |
| 2010/0197359 A1 | 8/2010 | Harris |
| 2010/0202346 A1 | 8/2010 | Sitzes et al. |
| 2010/0211259 A1 | 8/2010 | McClellan |
| 2010/0211282 A1 | 8/2010 | Nakata et al. |
| 2010/0211300 A1 | 8/2010 | Jaffe et al. |
| 2010/0211304 A1 | 8/2010 | Hwang et al. |
| 2010/0211441 A1 | 8/2010 | Sprigg et al. |
| 2010/0217458 A1 | 8/2010 | Schweiger et al. |
| 2010/0222939 A1 | 9/2010 | Namburu et al. |
| 2010/0228404 A1 | 9/2010 | Link et al. |
| 2010/0234071 A1 | 9/2010 | Shabtay et al. |
| 2010/0235042 A1 | 9/2010 | Ying |
| 2010/0235744 A1 | 9/2010 | Schultz |
| 2010/0235891 A1 | 9/2010 | Oglesbee et al. |
| 2010/0250071 A1 | 9/2010 | Pala et al. |
| 2010/0253493 A1 | 10/2010 | Szczerba et al. |
| 2010/0256836 A1 | 10/2010 | Mudalige |
| 2010/0265104 A1 | 10/2010 | Zlojutro |
| 2010/0268426 A1 | 10/2010 | Pathak et al. |
| 2010/0274410 A1 | 10/2010 | Tsien et al. |
| 2010/0280751 A1 | 11/2010 | Breed |
| 2010/0287303 A1 | 11/2010 | Smith et al. |
| 2010/0289632 A1 | 11/2010 | Seder et al. |
| 2010/0289643 A1 | 11/2010 | Trundle et al. |
| 2010/0291427 A1 | 11/2010 | Zhou |
| 2010/0295676 A1 | 11/2010 | Khachaturov et al. |
| 2010/0304640 A1 | 12/2010 | Sofman et al. |
| 2010/0305807 A1 | 12/2010 | Basir et al. |
| 2010/0306080 A1 | 12/2010 | Trandal et al. |
| 2010/0306309 A1 | 12/2010 | Santori et al. |
| 2010/0306435 A1 | 12/2010 | Nigoghosian et al. |
| 2010/0315218 A1 | 12/2010 | Cades et al. |
| 2010/0321151 A1 | 12/2010 | Matsuura et al. |
| 2010/0325626 A1 | 12/2010 | Greschler et al. |
| 2010/0332130 A1 | 12/2010 | Shimizu et al. |
| 2011/0015853 A1 | 1/2011 | DeKock et al. |
| 2011/0018736 A1 | 1/2011 | Carr |
| 2011/0021213 A1 | 1/2011 | Carr |
| 2011/0021234 A1 | 1/2011 | Tibbits et al. |
| 2011/0028138 A1 | 2/2011 | Davies-Moore et al. |
| 2011/0035098 A1 | 2/2011 | Goto et al. |
| 2011/0035141 A1 | 2/2011 | Barker et al. |
| 2011/0040438 A1 | 2/2011 | Kluge et al. |
| 2011/0050589 A1 | 3/2011 | Yan et al. |
| 2011/0053506 A1 | 3/2011 | Lemke et al. |
| 2011/0077808 A1 | 3/2011 | Hyde et al. |
| 2011/0078024 A1 | 3/2011 | Messier et al. |
| 2011/0080282 A1 | 4/2011 | Kleve et al. |
| 2011/0082615 A1 | 4/2011 | Small et al. |
| 2011/0084824 A1 | 4/2011 | Tewari et al. |
| 2011/0090078 A1 | 4/2011 | Kim et al. |
| 2011/0092159 A1 | 4/2011 | Park et al. |
| 2011/0093154 A1 | 4/2011 | Moinzadeh et al. |
| 2011/0093158 A1 | 4/2011 | Theisen et al. |
| 2011/0093438 A1 | 4/2011 | Poulsen |
| 2011/0093846 A1 | 4/2011 | Moinzadeh et al. |
| 2011/0105097 A1 | 5/2011 | Tadayon et al. |
| 2011/0106375 A1 | 5/2011 | Sundaram et al. |
| 2011/0112717 A1 | 5/2011 | Resner |
| 2011/0112969 A1 | 5/2011 | Zaid et al. |
| 2011/0117933 A1 | 5/2011 | Andersson |
| 2011/0119344 A1 | 5/2011 | Eustis |
| 2011/0130915 A1 | 6/2011 | Wright et al. |
| 2011/0134749 A1 | 6/2011 | Speks et al. |
| 2011/0137520 A1 | 6/2011 | Rector et al. |
| 2011/0145331 A1 | 6/2011 | Christie et al. |
| 2011/0172873 A1 | 7/2011 | Szwabowski et al. |
| 2011/0175754 A1 | 7/2011 | Karpinsky |
| 2011/0183658 A1 | 7/2011 | Zellner |
| 2011/0187520 A1 | 8/2011 | Filev et al. |
| 2011/0193707 A1 | 8/2011 | Ngo |
| 2011/0193726 A1 | 8/2011 | Szwabowski et al. |
| 2011/0195699 A1 | 8/2011 | Tadayon et al. |
| 2011/0197187 A1 | 8/2011 | Roh |
| 2011/0205047 A1 | 8/2011 | Patel et al. |
| 2011/0209079 A1 | 8/2011 | Tarte et al. |
| 2011/0210867 A1 | 9/2011 | Benedikt |
| 2011/0212717 A1 | 9/2011 | Rhoads et al. |
| 2011/0221656 A1 | 9/2011 | Haddick et al. |
| 2011/0224865 A1 | 9/2011 | Gordon et al. |
| 2011/0224898 A1 | 9/2011 | Scofield et al. |
| 2011/0225527 A1 | 9/2011 | Law et al. |
| 2011/0227757 A1 | 9/2011 | Chen et al. |
| 2011/0231091 A1 | 9/2011 | Gourlay et al. |
| 2011/0234369 A1 | 9/2011 | Cai et al. |
| 2011/0245999 A1 | 10/2011 | Kordonowy |
| 2011/0246210 A1 | 10/2011 | Matsur |
| 2011/0247013 A1 | 10/2011 | Feller et al. |
| 2011/0251734 A1 | 10/2011 | Schepp et al. |
| 2011/0257973 A1 | 10/2011 | Chutorash et al. |
| 2011/0267204 A1 | 11/2011 | Chuang et al. |
| 2011/0267205 A1 | 11/2011 | McClellan et al. |
| 2011/0286676 A1 | 11/2011 | El Dokor |
| 2011/0291886 A1 | 12/2011 | Krieter |
| 2011/0291926 A1 | 12/2011 | Gokturk et al. |
| 2011/0298808 A1 | 12/2011 | Rovik |
| 2011/0301844 A1 | 12/2011 | Aono |
| 2011/0307354 A1 | 12/2011 | Erman et al. |
| 2011/0307570 A1 | 12/2011 | Speks |
| 2011/0309926 A1 | 12/2011 | Eikelenberg et al. |
| 2011/0309953 A1 | 12/2011 | Petite et al. |
| 2011/0313653 A1 | 12/2011 | Lindner |
| 2011/0320089 A1 | 12/2011 | Lewis |
| 2012/0006610 A1 | 1/2012 | Wallace et al. |
| 2012/0010807 A1 | 1/2012 | Zhou |
| 2012/0016581 A1 | 1/2012 | Mochizuki et al. |
| 2012/0029852 A1 | 2/2012 | Goff et al. |
| 2012/0030002 A1 | 2/2012 | Bous et al. |
| 2012/0030512 A1 | 2/2012 | Wadhwa et al. |
| 2012/0038489 A1 | 2/2012 | Goldshmidt |
| 2012/0046822 A1 | 2/2012 | Anderson |
| 2012/0047530 A1 | 2/2012 | Shkedi |
| 2012/0053793 A1 | 3/2012 | Sala et al. |
| 2012/0053888 A1 | 3/2012 | Stahlin et al. |
| 2012/0059789 A1 | 3/2012 | Sakai et al. |
| 2012/0065815 A1 | 3/2012 | Hess |
| 2012/0065834 A1 | 3/2012 | Senart |
| 2012/0068956 A1 | 3/2012 | Jira et al. |
| 2012/0071097 A1 | 3/2012 | Matsushita et al. |
| 2012/0072244 A1 | 3/2012 | Collins et al. |
| 2012/0074770 A1 | 3/2012 | Lee |
| 2012/0083960 A1 | 4/2012 | Zhu et al. |
| 2012/0083971 A1 | 4/2012 | Preston |
| 2012/0084773 A1 | 4/2012 | Lee et al. |

(56) References Cited

U.S. PATENT DOCUMENTS

| | | |
|---|---|---|
| 2012/0089299 A1 | 4/2012 | Breed |
| 2012/0092251 A1 | 4/2012 | Hashimoto et al. |
| 2012/0101876 A1 | 4/2012 | Truvey et al. |
| 2012/0101914 A1 | 4/2012 | Kumar et al. |
| 2012/0105613 A1 | 5/2012 | Weng et al. |
| 2012/0106114 A1 | 5/2012 | Caron et al. |
| 2012/0109446 A1 | 5/2012 | Yousefi et al. |
| 2012/0109451 A1 | 5/2012 | Tan |
| 2012/0110356 A1 | 5/2012 | Yousefi et al. |
| 2012/0113822 A1 | 5/2012 | Letner |
| 2012/0115446 A1 | 5/2012 | Guatama et al. |
| 2012/0116609 A1 | 5/2012 | Jung et al. |
| 2012/0116678 A1 | 5/2012 | Witmer |
| 2012/0116696 A1 | 5/2012 | Wank |
| 2012/0146766 A1 | 6/2012 | Geisler et al. |
| 2012/0146809 A1 | 6/2012 | Oh et al. |
| 2012/0149341 A1 | 6/2012 | Tadayon et al. |
| 2012/0150651 A1 | 6/2012 | Hoffberg et al. |
| 2012/0155636 A1 | 6/2012 | Muthaiah |
| 2012/0158436 A1 | 6/2012 | Bauer et al. |
| 2012/0173900 A1 | 7/2012 | Diab et al. |
| 2012/0173905 A1 | 7/2012 | Diab et al. |
| 2012/0179325 A1 | 7/2012 | Faenger |
| 2012/0179547 A1 | 7/2012 | Besore et al. |
| 2012/0188876 A1 | 7/2012 | Chow et al. |
| 2012/0197523 A1 | 8/2012 | Kirsch |
| 2012/0197669 A1 | 8/2012 | Kote et al. |
| 2012/0204166 A1 | 8/2012 | Ichihara |
| 2012/0210160 A1 | 8/2012 | Fuhrman |
| 2012/0215375 A1 | 8/2012 | Chang |
| 2012/0217928 A1 | 8/2012 | Kulidjian |
| 2012/0218125 A1 | 8/2012 | Demirdjian et al. |
| 2012/0226413 A1 | 9/2012 | Chen et al. |
| 2012/0238286 A1 | 9/2012 | Mallavarapu et al. |
| 2012/0239242 A1 | 9/2012 | Uehara |
| 2012/0242510 A1 | 9/2012 | Choi et al. |
| 2012/0254763 A1 | 10/2012 | Protopapas et al. |
| 2012/0254804 A1 | 10/2012 | Shema et al. |
| 2012/0259951 A1 | 10/2012 | Schalk et al. |
| 2012/0265359 A1 | 10/2012 | Das |
| 2012/0274459 A1 | 11/2012 | Jaisimha et al. |
| 2012/0274481 A1 | 11/2012 | Ginsberg et al. |
| 2012/0284292 A1 | 11/2012 | Rechsteiner et al. |
| 2012/0289217 A1 | 11/2012 | Reimer et al. |
| 2012/0289253 A1 | 11/2012 | Haag et al. |
| 2012/0296567 A1 | 11/2012 | Breed |
| 2012/0313771 A1 | 12/2012 | Wottlifff, III |
| 2012/0316720 A1 | 12/2012 | Hyde et al. |
| 2012/0317561 A1 | 12/2012 | Aslam et al. |
| 2012/0323413 A1 | 12/2012 | Kedar-Dongarkar et al. |
| 2012/0327231 A1 | 12/2012 | Cochran et al. |
| 2013/0005263 A1 | 1/2013 | Sakata |
| 2013/0005414 A1 | 1/2013 | Bindra et al. |
| 2013/0013157 A1 | 1/2013 | Kim et al. |
| 2013/0019252 A1 | 1/2013 | Haase et al. |
| 2013/0024060 A1 | 1/2013 | Sukkarie et al. |
| 2013/0030645 A1 | 1/2013 | Divine et al. |
| 2013/0030811 A1 | 1/2013 | Olleon et al. |
| 2013/0031540 A1 | 1/2013 | Throop et al. |
| 2013/0031541 A1 | 1/2013 | Wilks et al. |
| 2013/0035063 A1 | 2/2013 | Fisk et al. |
| 2013/0046624 A1 | 2/2013 | Calman |
| 2013/0050069 A1 | 2/2013 | Ota |
| 2013/0055096 A1 | 2/2013 | Kim et al. |
| 2013/0059607 A1 | 3/2013 | Herz et al. |
| 2013/0063336 A1 | 3/2013 | Sugimoto et al. |
| 2013/0066512 A1 | 3/2013 | Willard et al. |
| 2013/0067599 A1 | 3/2013 | Raje et al. |
| 2013/0075530 A1 | 3/2013 | Shander et al. |
| 2013/0079964 A1 | 3/2013 | Sukkarie et al. |
| 2013/0083805 A1 | 4/2013 | Lu et al. |
| 2013/0085787 A1 | 4/2013 | Gore et al. |
| 2013/0086164 A1 | 4/2013 | Wheeler et al. |
| 2013/0099915 A1 | 4/2013 | Prasad et al. |
| 2013/0103196 A1 | 4/2013 | Monceaux et al. |
| 2013/0105264 A1 | 5/2013 | Ruth et al. |
| 2013/0116882 A1 | 5/2013 | Link et al. |
| 2013/0116915 A1 | 5/2013 | Ferreira et al. |
| 2013/0134730 A1 | 5/2013 | Ricci |
| 2013/0135118 A1 | 5/2013 | Ricci |
| 2013/0138591 A1 | 5/2013 | Ricci |
| 2013/0138714 A1 | 5/2013 | Ricci |
| 2013/0139140 A1 | 5/2013 | Rao et al. |
| 2013/0141247 A1 | 6/2013 | Ricci |
| 2013/0141252 A1 | 6/2013 | Ricci |
| 2013/0143495 A1 | 6/2013 | Ricci |
| 2013/0143546 A1 | 6/2013 | Ricci |
| 2013/0143601 A1 | 6/2013 | Ricci |
| 2013/0144459 A1 | 6/2013 | Ricci |
| 2013/0144460 A1 | 6/2013 | Ricci |
| 2013/0144461 A1 | 6/2013 | Ricci |
| 2013/0144462 A1 | 6/2013 | Ricci |
| 2013/0144463 A1 | 6/2013 | Ricci et al. |
| 2013/0144469 A1 | 6/2013 | Ricci |
| 2013/0144470 A1 | 6/2013 | Ricci |
| 2013/0144474 A1 | 6/2013 | Ricci |
| 2013/0144486 A1 | 6/2013 | Ricci |
| 2013/0144520 A1 | 6/2013 | Ricci |
| 2013/0144657 A1 | 6/2013 | Ricci |
| 2013/0145065 A1 | 6/2013 | Ricci |
| 2013/0145279 A1 | 6/2013 | Ricci |
| 2013/0145297 A1 | 6/2013 | Ricci et al. |
| 2013/0145360 A1 | 6/2013 | Ricci |
| 2013/0145401 A1 | 6/2013 | Ricci |
| 2013/0145482 A1 | 6/2013 | Ricci et al. |
| 2013/0147638 A1 | 6/2013 | Ricci |
| 2013/0151031 A1 | 6/2013 | Ricci |
| 2013/0151065 A1 | 6/2013 | Ricci |
| 2013/0151088 A1 | 6/2013 | Ricci |
| 2013/0151288 A1 | 6/2013 | Bowne et al. |
| 2013/0152003 A1 | 6/2013 | Ricci et al. |
| 2013/0154298 A1 | 6/2013 | Ricci |
| 2013/0157640 A1 | 6/2013 | Aycock |
| 2013/0157647 A1 | 6/2013 | Kolodziej |
| 2013/0158778 A1 | 6/2013 | Tengler et al. |
| 2013/0158821 A1 | 6/2013 | Ricci |
| 2013/0166096 A1 | 6/2013 | Jotanovic |
| 2013/0166097 A1 | 6/2013 | Ricci |
| 2013/0166098 A1 | 6/2013 | Lavie et al. |
| 2013/0166152 A1 | 6/2013 | Butterworth |
| 2013/0166208 A1 | 6/2013 | Forstall et al. |
| 2013/0167159 A1 | 6/2013 | Ricci et al. |
| 2013/0173531 A1 | 7/2013 | Rinearson et al. |
| 2013/0179689 A1 | 7/2013 | Matsumoto et al. |
| 2013/0190978 A1 | 7/2013 | Kato et al. |
| 2013/0194108 A1 | 8/2013 | Lapiotis et al. |
| 2013/0197796 A1 | 8/2013 | Obradovich et al. |
| 2013/0198031 A1 | 8/2013 | Mitchell et al. |
| 2013/0198737 A1 | 8/2013 | Ricci |
| 2013/0198802 A1 | 8/2013 | Ricci |
| 2013/0200991 A1 | 8/2013 | Ricci et al. |
| 2013/0203400 A1 | 8/2013 | Ricci |
| 2013/0204455 A1 | 8/2013 | Chia et al. |
| 2013/0204457 A1 | 8/2013 | King |
| 2013/0204466 A1 | 8/2013 | Ricci |
| 2013/0204484 A1 | 8/2013 | Ricci |
| 2013/0204493 A1 | 8/2013 | Ricci et al. |
| 2013/0204943 A1 | 8/2013 | Ricci |
| 2013/0205026 A1 | 8/2013 | Ricci |
| 2013/0205412 A1 | 8/2013 | Ricci |
| 2013/0207794 A1 | 8/2013 | Patel et al. |
| 2013/0212065 A1 | 8/2013 | Rahnama |
| 2013/0212659 A1 | 8/2013 | Maher et al. |
| 2013/0215116 A1 | 8/2013 | Siddique et al. |
| 2013/0218412 A1 | 8/2013 | Ricci |
| 2013/0218445 A1 | 8/2013 | Basir |
| 2013/0219039 A1 | 8/2013 | Ricci |
| 2013/0226365 A1 | 8/2013 | Brozovich |
| 2013/0226371 A1 | 8/2013 | Rovik et al. |
| 2013/0226392 A1 | 8/2013 | Schneider et al. |
| 2013/0226449 A1 | 8/2013 | Rovik et al. |
| 2013/0226622 A1 | 8/2013 | Adamson et al. |
| 2013/0227648 A1 | 8/2013 | Ricci |
| 2013/0231784 A1 | 9/2013 | Rovik et al. |

(56) References Cited

U.S. PATENT DOCUMENTS

| | | |
|---|---|---|
| 2013/0231800 A1 | 9/2013 | Ricci |
| 2013/0232142 A1 | 9/2013 | Nielsen et al. |
| 2013/0238165 A1 | 9/2013 | Garrett et al. |
| 2013/0241720 A1 | 9/2013 | Ricci et al. |
| 2013/0245882 A1 | 9/2013 | Ricci |
| 2013/0250933 A1 | 9/2013 | Yousefi et al. |
| 2013/0261871 A1 | 10/2013 | Hobbs et al. |
| 2013/0261966 A1 | 10/2013 | Wang et al. |
| 2013/0265178 A1 | 10/2013 | Tengler et al. |
| 2013/0274997 A1 | 10/2013 | Chien |
| 2013/0279111 A1 | 10/2013 | Lee |
| 2013/0279491 A1 | 10/2013 | Rubin et al. |
| 2013/0282238 A1 | 10/2013 | Ricci et al. |
| 2013/0282357 A1 | 10/2013 | Rubin et al. |
| 2013/0282946 A1 | 10/2013 | Ricci |
| 2013/0288606 A1 | 10/2013 | Kirsch |
| 2013/0293364 A1 | 11/2013 | Ricci et al. |
| 2013/0293452 A1 | 11/2013 | Ricci et al. |
| 2013/0293480 A1 | 11/2013 | Kritt et al. |
| 2013/0295901 A1 | 11/2013 | Abramson et al. |
| 2013/0295908 A1 | 11/2013 | Zeinstra et al. |
| 2013/0295913 A1 | 11/2013 | Matthews et al. |
| 2013/0300554 A1 | 11/2013 | Braden |
| 2013/0301584 A1 | 11/2013 | Addepalli et al. |
| 2013/0304371 A1 | 11/2013 | Kitatani et al. |
| 2013/0308265 A1 | 11/2013 | Arnouse |
| 2013/0309977 A1 | 11/2013 | Heines et al. |
| 2013/0311038 A1 | 11/2013 | Kim et al. |
| 2013/0325453 A1 | 12/2013 | Levien et al. |
| 2013/0325568 A1 | 12/2013 | Mangalvedkar et al. |
| 2013/0329372 A1 | 12/2013 | Wilkins |
| 2013/0332023 A1 | 12/2013 | Bertosa et al. |
| 2013/0338914 A1 | 12/2013 | Weiss |
| 2013/0339027 A1 | 12/2013 | Dokor et al. |
| 2013/0345929 A1 | 12/2013 | Bowden et al. |
| 2014/0028542 A1 | 1/2014 | Lovitt et al. |
| 2014/0032014 A1 | 1/2014 | DeBiasio et al. |
| 2014/0054957 A1 | 2/2014 | Bellis |
| 2014/0058672 A1 | 2/2014 | Wansley et al. |
| 2014/0066014 A1 | 3/2014 | Nicholson et al. |
| 2014/0067201 A1 | 3/2014 | Visintainer et al. |
| 2014/0067564 A1 | 3/2014 | Yuan |
| 2014/0070917 A1 | 3/2014 | Protopapas |
| 2014/0081544 A1 | 3/2014 | Fry |
| 2014/0088798 A1 | 3/2014 | Himmelstein |
| 2014/0096068 A1 | 4/2014 | Dewan et al. |
| 2014/0097955 A1 | 4/2014 | Lovitt et al. |
| 2014/0109075 A1 | 4/2014 | Hoffman et al. |
| 2014/0109080 A1 | 4/2014 | Ricci |
| 2014/0120829 A1 | 5/2014 | Bhamidipati et al. |
| 2014/0121862 A1 | 5/2014 | Zarrella et al. |
| 2014/0125802 A1 | 5/2014 | Beckert et al. |
| 2014/0143839 A1 | 5/2014 | Ricci |
| 2014/0164611 A1 | 6/2014 | Molettiere et al. |
| 2014/0168062 A1 | 6/2014 | Katz et al. |
| 2014/0168436 A1 | 6/2014 | Pedicino |
| 2014/0169621 A1 | 6/2014 | Burr |
| 2014/0171752 A1 | 6/2014 | Park et al. |
| 2014/0172727 A1 | 6/2014 | Abhyanker et al. |
| 2014/0188533 A1 | 7/2014 | Davidson |
| 2014/0195272 A1 | 7/2014 | Sadiq et al. |
| 2014/0198216 A1 | 7/2014 | Zhai et al. |
| 2014/0200737 A1 | 7/2014 | Lortz et al. |
| 2014/0207328 A1 | 7/2014 | Wolf et al. |
| 2014/0220966 A1 | 8/2014 | Muetzel et al. |
| 2014/0222298 A1 | 8/2014 | Gurin |
| 2014/0223384 A1 | 8/2014 | Graumann |
| 2014/0240089 A1 | 8/2014 | Chang |
| 2014/0244078 A1 | 8/2014 | Downey et al. |
| 2014/0244111 A1 | 8/2014 | Gross et al. |
| 2014/0244156 A1 | 8/2014 | Magnusson et al. |
| 2014/0245277 A1 | 8/2014 | Petro et al. |
| 2014/0245278 A1 | 8/2014 | Zellen |
| 2014/0245284 A1 | 8/2014 | Alrabady et al. |
| 2014/0252091 A1 | 9/2014 | Morse et al. |
| 2014/0257627 A1 | 9/2014 | Hagan, Jr. |
| 2014/0267035 A1 | 9/2014 | Schalk et al. |
| 2014/0277936 A1 | 9/2014 | El Dokor et al. |
| 2014/0278070 A1 | 9/2014 | McGavran et al. |
| 2014/0278071 A1 | 9/2014 | San Filippo et al. |
| 2014/0281971 A1 | 9/2014 | Isbell, III et al. |
| 2014/0282161 A1 | 9/2014 | Cash |
| 2014/0282278 A1 | 9/2014 | Anderson et al. |
| 2014/0282470 A1 | 9/2014 | Buga et al. |
| 2014/0282931 A1 | 9/2014 | Protopapas |
| 2014/0292545 A1 | 10/2014 | Nemoto |
| 2014/0292665 A1 | 10/2014 | Lathrop et al. |
| 2014/0303899 A1 | 10/2014 | Fung |
| 2014/0306799 A1 | 10/2014 | Ricci |
| 2014/0306814 A1 | 10/2014 | Ricci |
| 2014/0306817 A1 | 10/2014 | Ricci |
| 2014/0306826 A1 | 10/2014 | Ricci |
| 2014/0306833 A1 | 10/2014 | Ricci |
| 2014/0306834 A1 | 10/2014 | Ricci |
| 2014/0306835 A1 | 10/2014 | Ricci |
| 2014/0307655 A1 | 10/2014 | Ricci |
| 2014/0307724 A1 | 10/2014 | Ricci |
| 2014/0308902 A1 | 10/2014 | Ricci |
| 2014/0309789 A1 | 10/2014 | Ricci |
| 2014/0309790 A1 | 10/2014 | Ricci |
| 2014/0309804 A1 | 10/2014 | Ricci |
| 2014/0309805 A1 | 10/2014 | Ricci |
| 2014/0309806 A1 | 10/2014 | Ricci |
| 2014/0309813 A1 | 10/2014 | Ricci |
| 2014/0309814 A1 | 10/2014 | Ricci et al. |
| 2014/0309815 A1 | 10/2014 | Ricci et al. |
| 2014/0309838 A1 | 10/2014 | Ricci |
| 2014/0309839 A1 | 10/2014 | Ricci et al. |
| 2014/0309847 A1 | 10/2014 | Ricci |
| 2014/0309849 A1 | 10/2014 | Ricci |
| 2014/0309852 A1 | 10/2014 | Ricci |
| 2014/0309853 A1 | 10/2014 | Ricci |
| 2014/0309862 A1 | 10/2014 | Ricci |
| 2014/0309863 A1 | 10/2014 | Ricci |
| 2014/0309864 A1 | 10/2014 | Ricci |
| 2014/0309865 A1 | 10/2014 | Ricci |
| 2014/0309866 A1 | 10/2014 | Ricci |
| 2014/0309867 A1 | 10/2014 | Ricci |
| 2014/0309868 A1 | 10/2014 | Ricci |
| 2014/0309869 A1 | 10/2014 | Ricci |
| 2014/0309870 A1 | 10/2014 | Ricci et al. |
| 2014/0309871 A1 | 10/2014 | Ricci |
| 2014/0309872 A1 | 10/2014 | Ricci |
| 2014/0309873 A1 | 10/2014 | Ricci |
| 2014/0309874 A1 | 10/2014 | Ricci |
| 2014/0309875 A1 | 10/2014 | Ricci |
| 2014/0309876 A1 | 10/2014 | Ricci |
| 2014/0309877 A1 | 10/2014 | Ricci |
| 2014/0309878 A1 | 10/2014 | Ricci |
| 2014/0309879 A1 | 10/2014 | Ricci |
| 2014/0309880 A1 | 10/2014 | Ricci |
| 2014/0309885 A1 | 10/2014 | Ricci |
| 2014/0309886 A1 | 10/2014 | Ricci |
| 2014/0309891 A1 | 10/2014 | Ricci |
| 2014/0309892 A1 | 10/2014 | Ricci |
| 2014/0309893 A1 | 10/2014 | Ricci |
| 2014/0309913 A1 | 10/2014 | Ricci et al. |
| 2014/0309919 A1 | 10/2014 | Ricci |
| 2014/0309920 A1 | 10/2014 | Ricci |
| 2014/0309921 A1 | 10/2014 | Ricci et al. |
| 2014/0309922 A1 | 10/2014 | Ricci |
| 2014/0309923 A1 | 10/2014 | Ricci |
| 2014/0309927 A1 | 10/2014 | Ricci |
| 2014/0309929 A1 | 10/2014 | Ricci |
| 2014/0309930 A1 | 10/2014 | Ricci |
| 2014/0309934 A1 | 10/2014 | Ricci |
| 2014/0309935 A1 | 10/2014 | Ricci |
| 2014/0309982 A1 | 10/2014 | Ricci |
| 2014/0310031 A1 | 10/2014 | Ricci |
| 2014/0310075 A1 | 10/2014 | Ricci |
| 2014/0310103 A1 | 10/2014 | Ricci |
| 2014/0310186 A1 | 10/2014 | Ricci |
| 2014/0310277 A1 | 10/2014 | Ricci |
| 2014/0310379 A1 | 10/2014 | Ricci et al. |

(56) References Cited

U.S. PATENT DOCUMENTS

| | | |
|---|---|---|
| 2014/0310594 A1 | 10/2014 | Ricci et al. |
| 2014/0310610 A1 | 10/2014 | Ricci |
| 2014/0310702 A1 | 10/2014 | Ricci et al. |
| 2014/0310739 A1 | 10/2014 | Ricci et al. |
| 2014/0310788 A1 | 10/2014 | Ricci |
| 2014/0322676 A1 | 10/2014 | Raman |
| 2014/0347207 A1 | 11/2014 | Zeng et al. |
| 2014/0347265 A1 | 11/2014 | Allen et al. |
| 2015/0007155 A1 | 1/2015 | Hoffman et al. |
| 2015/0012186 A1 | 1/2015 | Horseman |
| 2015/0032366 A1 | 1/2015 | Man et al. |
| 2015/0032670 A1 | 1/2015 | Brazell |
| 2015/0057839 A1 | 2/2015 | Chang et al. |
| 2015/0061895 A1 | 3/2015 | Ricci |
| 2015/0081133 A1 | 3/2015 | Schulz |
| 2015/0081167 A1 | 3/2015 | Pisz et al. |
| 2015/0088423 A1 | 3/2015 | Tuukkanen |
| 2015/0088515 A1 | 3/2015 | Beaumont et al. |
| 2015/0116200 A1 | 4/2015 | Kurosawa et al. |
| 2015/0158499 A1 | 6/2015 | Koravadi |
| 2015/0161832 A1 | 6/2015 | Esselink et al. |
| 2015/0178034 A1 | 6/2015 | Penilla et al. |
| 2016/0008985 A1 | 1/2016 | Kim et al. |
| 2016/0039356 A1 | 2/2016 | Talwar et al. |
| 2016/0070527 A1 | 3/2016 | Ricci |
| 2016/0086391 A1 | 3/2016 | Ricci |
| 2016/0269456 A1 | 9/2016 | Ricci |
| 2016/0269469 A1 | 9/2016 | Ricci |
| 2017/0053460 A1* | 2/2017 | Hauser ............... G07C 5/008 |

FOREIGN PATENT DOCUMENTS

| | | |
|---|---|---|
| CN | 101303878 | 11/2008 |
| CN | 102467827 | 5/2012 |
| EP | 1223567 | 7/2002 |
| EP | 1484729 | 12/2004 |
| EP | 2192015 | 6/2010 |
| JP | 2004-284450 | 10/2004 |
| KR | 2006-0128484 | 12/2006 |
| WO | WO 2007/126204 | 11/2007 |
| WO | WO 2012/102879 | 8/2012 |
| WO | WO 2013/074866 | 5/2013 |
| WO | WO 2013/074867 | 5/2013 |
| WO | WO 2013/074868 | 5/2013 |
| WO | WO 2013/074897 | 5/2013 |
| WO | WO 2013/074899 | 5/2013 |
| WO | WO 2013/074901 | 5/2013 |
| WO | WO 2013/074919 | 5/2013 |
| WO | WO 2013/074981 | 5/2013 |
| WO | WO 2013/074983 | 5/2013 |
| WO | WO 2013/075005 | 5/2013 |
| WO | WO 2013/181310 | 12/2013 |
| WO | WO 2014/014862 | 1/2014 |
| WO | WO 2014/143563 | 9/2014 |
| WO | WO 2014/158667 | 10/2014 |
| WO | WO 2014/158672 | 10/2014 |
| WO | WO 2014/158766 | 10/2014 |
| WO | WO 2014/172312 | 10/2014 |
| WO | WO 2014/172313 | 10/2014 |
| WO | WO 2014/172316 | 10/2014 |
| WO | WO 2014/172320 | 10/2014 |
| WO | WO 2014/172322 | 10/2014 |
| WO | WO 2014/172323 | 10/2014 |
| WO | WO 2014/172327 | 10/2014 |
| WO | WO 2016/145073 | 9/2016 |
| WO | WO 2016/145100 | 9/2016 |

OTHER PUBLICATIONS

"Radio-frequency identification," Wikipedia, retrieved from https://en.wikipedia.org/wiki/Radio-frequency_identification, retrieved on Dec. 9, 2016, 23 pages.

"Product code," Wikipedia, retrieved from https://en.wikipedia.org/wiki/Product_code, retrieved on Dec. 9, 2016, 1 page.

"Electronic Product Code," Wikipedia, retrieved from https://en.wikipedia.org/wiki/Electronic_Product_Code, retrieved on Dec. 9, 2016, 4 page.

U.S. Appl. No. 61/567,962, filed Dec. 7, 2011, Baarman et al.

U.S. Appl. No. 15/406,138, filed Jan. 13, 2017, Newman

U.S. Appl. No. 15/407,480, filed Jan. 17, 2017, Falkson et al.

U.S. Appl. No. 15/414,897, filed Jan. 25, 2017, Chen et al.

"Nexus 10 Guidebook for Android," Google Inc., © 2012, Edition 1.2, 166 pages.

"Self-Driving: Self-Driving Autonomous Cars," available at http://www.automotivetechnologies.com/autonomous-self-driving-cars, accessed Dec. 2016, 9 pages.

Amor-Segan et al., "Towards the Self Healing Vehicle," Automotive Electronics, Jun. 2007, 2007 3rd Institution of Engineering and Technology Conference, 7 pages.

Bennett, "Meet Samsung's Version of Apple AirPlay," CNET.com, Oct. 10, 2012, 11 pages.

Cairnie et al., "Using Finger-Pointing to Operate Secondary Controls in Automobiles," Proceedings of the IEEE Intelligent Vehicles Symposium 2000, Oct. 3-5, 2000, 6 pages.

Clark, "How Self-Driving Cars Work: The Nuts and Bolts Behind Google's Autonomous Car Program," Feb. 21, 2015, available at http://www.makeuseof.com/tag/how-self-driving-cars-work-the-nuts-and-bolts-behind-googles-autonomous-car-program/, 9 pages.

Deaton et al., "How Driverless Cars Will Work," Jul. 1, 2008, HowStuffWorks.com. <http://auto.howstuffworks.com/under-the-hood/trends-innovations/driverless-car.htm> Sep. 18, 2017, 10 pages.

Dumbaugh, "Safe Streets, Livable Streets: A Positive Approach to urban Roadside Design," Ph.D. dissertation for School of Civil & Environ. Engr., Georgia Inst. of Technology, Dec. 2005, 235 pages.

Fei et al., "A QoS-aware Dynamic Bandwidth Allocation Algorithm for Relay Stations in IEEE 802.16j-based Vehicular Networks," Proceedings of the 2010 IEEE Global Telecommunications Conference, Dec. 10, 2010, 10 pages.

Ge et al., "Optimal Relay Selection in IEEE 802.16j Multihop Relay Vehicular Networks," IEEE Transactions on Vehicular Technology, 2010, vol. 59(5), pp. 2198-2206.

Guizzo, Erico, "How Google's Self-Driving Car Works," Oct. 18, 2011, available at https://spectrum.ieee.org/automaton/robotics/artificial-intelligence/how-google-self-driving-car-works, 5 pages.

Heer et al., "ALPHA: An Adaptive and Lightweight Protocol for Hop-by-hop Authentication," Proceedings of CoNEXT 2008, Dec. 2008, pp. 1-12.

Jahnich et al., "Towards a Middleware Approach for a Self-Configurable Automotive Embedded System," International Federation for Information Processing, 2008, pp. 55-65.

Persson "Adaptive Middleware for Self-Configurable Embedded Real-Time Systems," KTH Industrial Engineering and Management, 2009, pp. iii-71 and references.

Raychaudhuri et al., "Emerging Wireless Technologies and the Future Mobile Internet," p. 48, Cambridge Press, 2011, 3 pages.

Stephens, Leah, "How Driverless Cars Work," Interesting Engineering, Apr. 28, 2016, available at https://interestingengineering.com/driverless-cars-work/, 7 pages.

Stoller, "Leader Election in Distributed Systems with Crash Failures," Indiana University, 1997, pp. 1-15.

Strunk et al., "The Elements of Style," 3d ed., Macmillan Publishing Co., 1979, 3 pages.

Suwatthikul, "Fault detection and diagnosis for in-vehicle networks," Intech, 2010, pp. 283-286 [retrieved from: www.intechopen.com/books/fault-detection-and-diagnosis-for-in-vehicle-networks].

Walter et al., "The smart car seat: personalized monitoring of vital signs in automotive applications." Personal and Ubiquitous Computing, Oct. 2011, vol. 15, No. 7, pp. 707-715.

Wolf et al., "Design, Implementation, and Evaluation of a Vehicular Hardware Security Module," ICISC'11 Proceedings of the 14th Int'l Conf. Information Security & Cryptology, Springer-Verlag Berlin, Heidelberg, 2011, pp. 302-318.

Official Action for U.S. Appl. No. 15/407,480, dated Sep. 6, 2017, 13 pages.

(56) References Cited

OTHER PUBLICATIONS

Official Action for U.S. Appl. No. 15/406,138, dated Jul. 13, 2017, 6 pages.
Official Action for U.S. Appl. No. 15/406,138, dated Dec. 28, 2017, 7 pages.

* cited by examiner

Fig. 3

| Charging Type | Compatible Vehicle Charging Panel Types | Compatible Vehicle Storage Units | Available Automation Level | Charging Service Status | Charge Rate | Cost | Other | Shielding |
|---|---|---|---|---|---|---|---|---|
| Station: manual | Roof, Side | x, z | Low | Up | Low | $100 | A, B, C | On |
| Station: manual | Roof, Side | x, z | Low | Up | Medium | $150 | A, C | On |
| Station: manual | Roof, Side | x, z | Low | Up | High | $400 | A, B, C | On |
| Station: robotic | Roof, Side | x, z | Medium | Down | Medium | $150 | A, B, D | On |
| Station: robotic | Roof, Side | x, z | High | Down | High | $500 | B, D | On |
| Station: robotic | Roof, Side | x, z | High | Down | High | $500 | B, C | On |
| Roadway | Side, Lower | x, z | Low | Up | Low | $50 | A, C, E | Off |
| Roadway | Side, Lower | x, z | Medium | Up | Low | $100 | A, C, E | Off |
| Roadway | Side, Lower | x, z | Medium | Up | Low | $100 | A, C, E | Off |
| Emergency: truck | Roof, Side, Lower | x, y | Low | Up | Low | $150 | A, B | Off |
| Emergency: truck | Roof, Side, Lower | x, y | Medium | Up | Medium | $200 | A, B | Off |
| Emergency: truck | Roof, Side, Lower | x, y | Medium | Up | High | $500 | A, D | Off |
| Emergency: UAV | Roof | x | Medium | Down | Medium | $500 | A, B, C | Off |
| Emergency: UAV | Roof | x | High | Down | High | $800 | B | Off |
| Emergency: UAV | Roof | x | High | Down | High | $800 | B | Off |
| Overhead | Roof | x, y | Low | Up | Low | $150 | B, D | Off |
| Overhead | Roof | x, y | Medium | Up | Low | $200 | B, C | Off |
| Overhead | Roof | x, y | Medium | Up | Low | $200 | B, C | Off |

VEHICLE IDENTIFICATION OR AUTHENTICATION

CROSS REFERENCE TO RELATED APPLICATIONS

The present application claims the benefit of and priority, under 35 U.S.C. § 119(e), to U.S. Provisional Application Ser. Nos. 62/359,563, filed Jul. 7, 2016, entitled "Next Generation Vehicle", and 62/378,348, filed Aug. 23, 2016, entitled "Next Generation Vehicle." The entire disclosures of the applications listed above are hereby incorporated by reference, in their entirety, for all that they teach and for all purposes.

FIELD

The present disclosure is generally directed to vehicle systems, in particular, toward electric and/or hybrid-electric vehicles.

BACKGROUND

In recent years, transportation methods have changed substantially. This change is due in part to a concern over the limited availability of natural resources, a proliferation in personal technology, and a societal shift to adopt more environmentally friendly transportation solutions. These considerations have encouraged the development of a number of new flexible-fuel vehicles, hybrid-electric vehicles, and electric vehicles.

While these vehicles appear to be new they are generally implemented as a number of traditional subsystems that are merely tied to an alternative power source. In fact, the design and construction of the vehicles is limited to standard frame sizes, shapes, materials, and transportation concepts. Among other things, these limitations fail to take advantage of the benefits of new technology, power sources, and support infrastructure.

BRIEF DESCRIPTION OF THE DRAWINGS

FIG. 3 is a diagram of an embodiment of a data structure for storing information about a vehicle in an environment;

DETAILED DESCRIPTION

Embodiments of the present disclosure will be described in connection with a vehicle, and in accordance with one exemplary embodiment an electric vehicle and/or hybrid-electric vehicle and associated systems.

With attention to FIGS. 1-11, embodiments of the electric vehicle system 10 and method of use are depicted.

Figure 1:
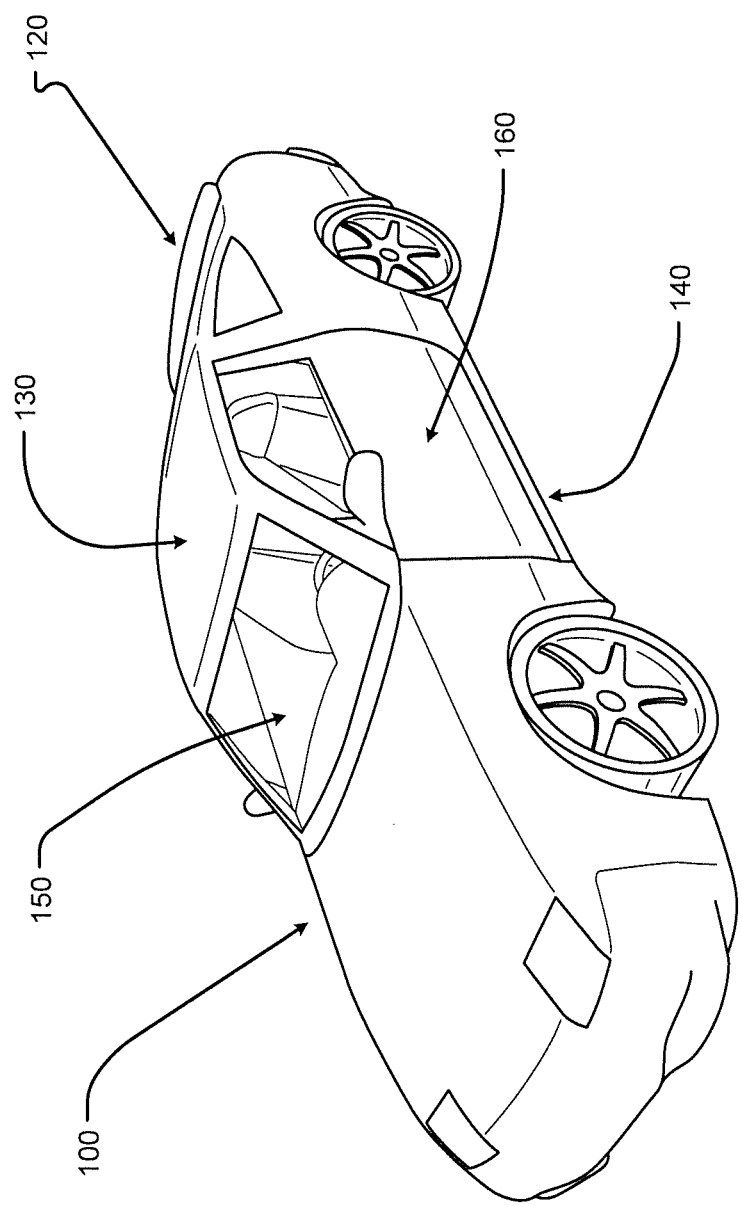
FIG. 1 shows a vehicle in accordance with embodiments of the present disclosure.

Referring to FIG. 1, the electric vehicle system comprises electric vehicle 100. The electric vehicle 100 comprises vehicle front 110, vehicle aft 120, vehicle roof 130, vehicle side 160, vehicle undercarriage 140 and vehicle interior 150.

Figure 2:
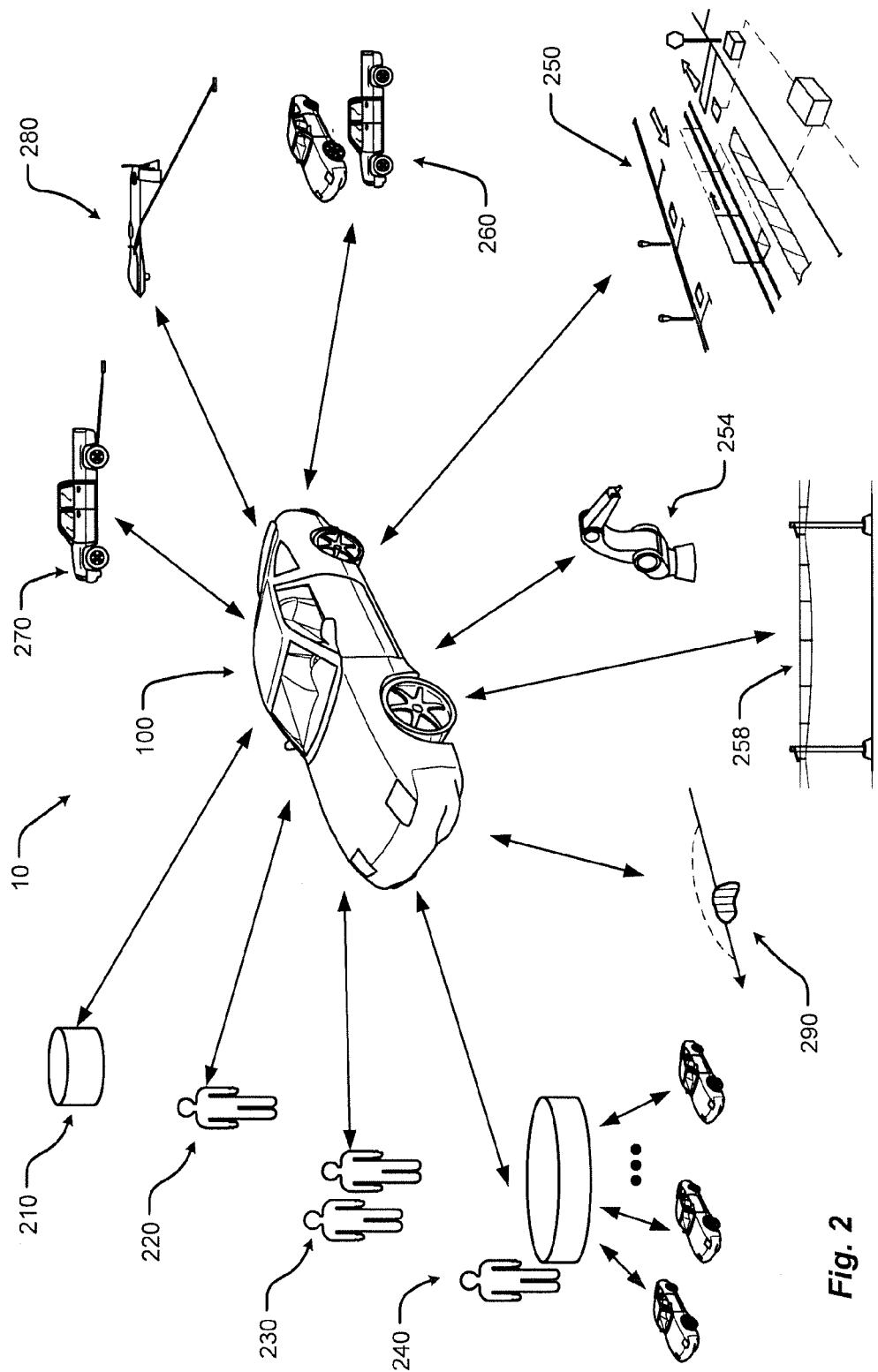
FIG. 2 shows a vehicle in an environment in accordance with embodiments of the present disclosure.

Referring to FIG. 2, the vehicle 100 is depicted in a plurality of exemplary environments. The vehicle 100 may operate in any one or more of the depicted environments in any combination. Other embodiments are possible but are not depicted in FIG. 2. Generally, the vehicle 100 may operate in environments which enable charging of the vehicle 100 and/or operation of the vehicle 100. More specifically, the vehicle 100 may receive a charge via one or more means comprising emergency charging vehicle system 270, aerial vehicle charging system 280, roadway system 250, robotic charging system 254 and overhead charging system 258. The vehicle 100 may interact and/or operate in an environment comprising one or more other roadway vehicles 260. The vehicle 100 may engage with elements within the vehicle 100 comprising vehicle driver 220, vehicle passengers 220 and vehicle database 210. In one embodiment, vehicle database 210 does not physically reside in the vehicle 100 but is instead accessed remotely, e.g. by wireless communication, and resides in another location such as a residence or business location. Vehicle 100 may operate autonomously and/or semi-autonomously in an autonomous environment 290 (here, depicted as a roadway environment presenting a roadway obstacle of which the vehicle 100 autonomously identifies and steers the vehicle 100 clear of the obstacle). Furthermore, the vehicle 100 may engage with a remote operator system 240, which may provide fleet management instructions or control.

FIG. 3 is a diagram of an embodiment of a data structure 300 for storing information about a vehicle 100 in an environment. The data structure may be stored in vehicle database 210. Generally, data structure 300 identifies operational data associated with charging types 310A. The data structures 300 may be accessible by a vehicle controller. The data contained in data structure 300 enables, among other things, for the vehicle 100 to receive a charge from a given charging type.

Data may comprise charging type 310A comprising a manual charging station 310J, robotic charging station 310K such as robotic charging system 254, a roadway charging system 310L such as those of roadway system 250, an emergency charging system 310M such as that of emergency charging vehicle system 270, an emergency charging system 310N such as that of aerial vehicle charging system 280, and overhead charging type 310O such as that of overhead charging system 258.

Compatible vehicle charging panel types 310B comprise locations on vehicle 100 wherein charging may be received, such as vehicle roof 130, vehicle side 160 and vehicle lower or undercarriage 140. Compatible vehicle storage units 310C data indicates storage units types that may receive power from a given charging type 310A. Available automation level 310D data indicates the degree of automation available for a given charging type; a high level may indicate full automation, allowing the vehicle driver 220 and/or vehicle passengers 230 to not involve themselves in charging operations, while a low level of automation may require the driver 220 and/or occupant 230 to manipulate/position a vehicle charging device to engage with a particular charging type 310A to receive charging. Charging status 310E indicates whether a charging type 310A is available for charging (i.e. is "up") or is unavailable for charging (i.e. is "down"). Charge rate 310F provides a relative value for time to charge, while Cost 310G indicates the cost to vehicle 100 to receive a given charge. The Other data element 310H may provide additional data relevant to a given charging type 310A, such as a recommended separation distance between a vehicle charging plate and the charging source. The Shielding data element 310I indicates if electromagnetic shielding is recommended for a given charging type 310A and/or charging configuration. Further data fields 310P, 310Q are possible.

Figure 4A:
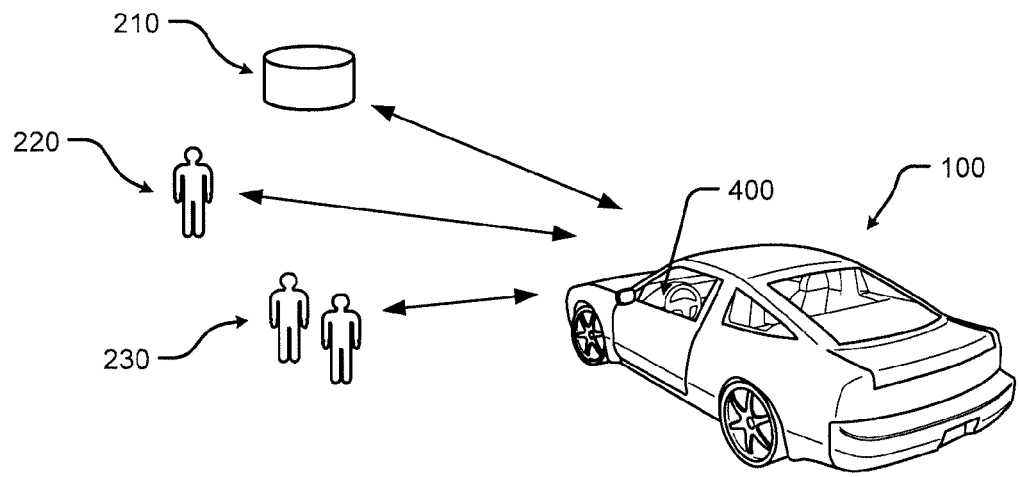
FIG. 4A shows a vehicle in a user environment in accordance with embodiments of the present disclosure.

FIG. 4A depicts the vehicle 100 in a user environment comprising vehicle database 210, vehicle driver 220 and vehicle passengers 230. Vehicle 100 further comprises vehicle instrument panel 400 to facilitate or enable interactions with one or more of vehicle database 210, vehicle driver 220 and vehicle passengers 230. In one embodiment, driver 210 interacts with instrument panel 400 to query database 210 so as to locate available charging options and to consider or weigh associated terms and conditions of the charging options. Once a charging option is selected, driver 210 may engage or operate a manual control device (e.g., a joystick) to position a vehicle charging receiver panel so as to receive a charge.

Figure 4B:
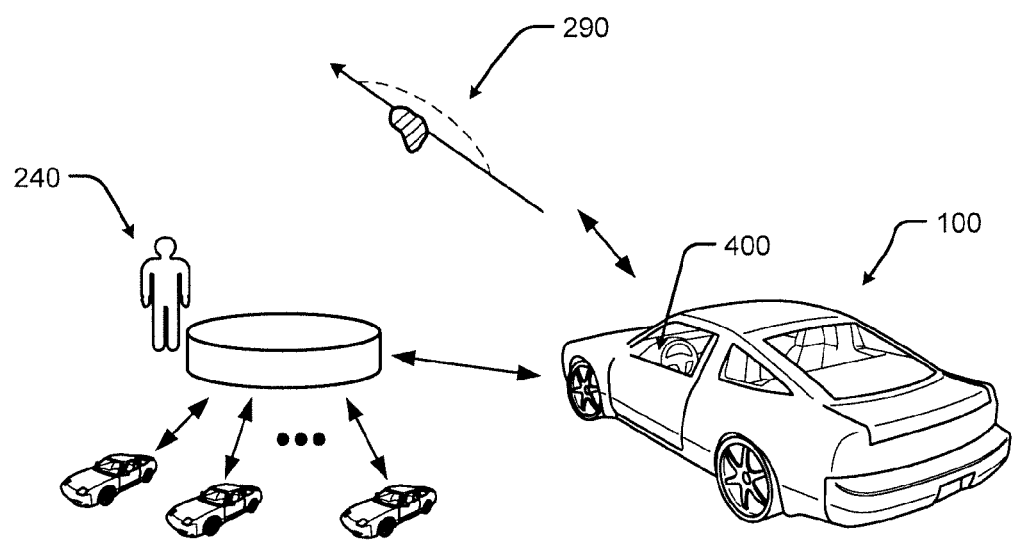
FIG. 4B shows a vehicle in a fleet management and automated operation environment in accordance with embodiments of the present disclosure.

FIG. 4B depicts the vehicle 100 in a user environment comprising a remote operator system 240 and an autonomous driving environment 290. In the remote operator system 240 environment, a fleet of electric vehicles 100 (or mixture of electric and non-electric vehicles) is managed and/or controlled remotely. For example, a human operator may dictate that only certain types of charging types are to be used, or only those charging types below a certain price point are to be used. The remote operator system 240 may comprise a database comprising operational data, such as fleet-wide operational data. In another example, the vehicle 100 may operate in an autonomous driving environment 290 wherein the vehicle 100 is operated with some degree of autonomy, ranging from complete autonomous operation to semi-automation wherein only specific driving parameters (e.g., speed control or obstacle avoidance) are maintained or controlled autonomously. In FIG. 4B, autonomous driving environment 290 depicts an oil slick roadway hazard that triggers that triggers the vehicle 100, while in an automated obstacle avoidance mode, to automatically steer around the roadway hazard.

Figure 4C:
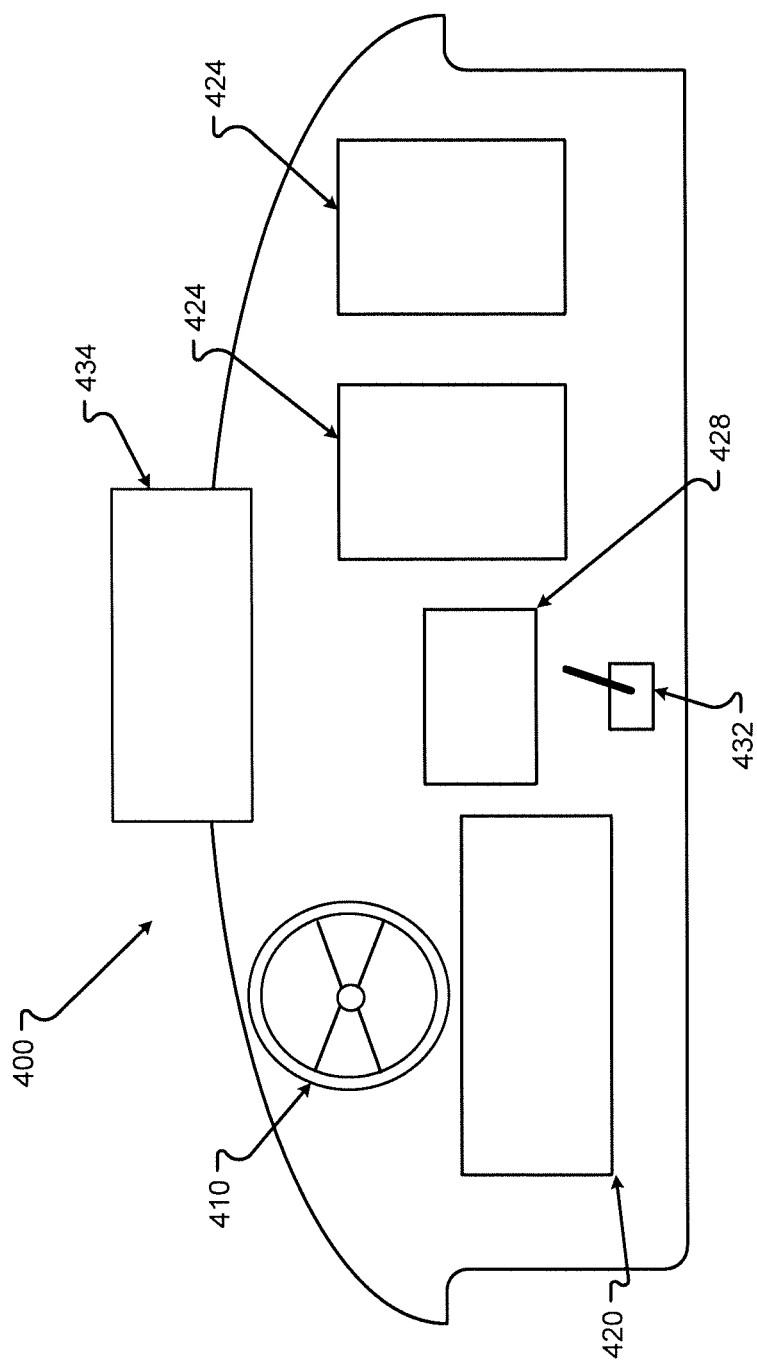
FIG. 4C shows an embodiment of the instrument panel of the vehicle according to one embodiment of the present disclosure.

FIG. 4C shows one embodiment of the vehicle instrument panel 400 of vehicle 100. Instrument panel 400 of vehicle 100 comprises steering wheel 410, vehicle operational display 420 (which would provide basic driving data such as speed), one or more auxiliary displays 424 (which may display, e.g., entertainment applications such as music or radio selections), heads-up display 434 (which may provide, e.g., guidance information such as route to destination, or obstacle warning information to warn of a potential collision, or some or all primary vehicle operational data such as speed), power management display 428 (which may provide, e.g., data as to electric power levels of vehicle 100), and charging manual controller 432 (which provides a physical input, e.g. a joystick, to manual maneuver, e.g., a vehicle charging plate to a desired separation distance). One or more of displays of instrument panel 400 may be touch-screen displays. One or more displays of instrument panel 400 may be mobile devices and/or applications residing on a mobile device such as a smart phone.

Figure 5:
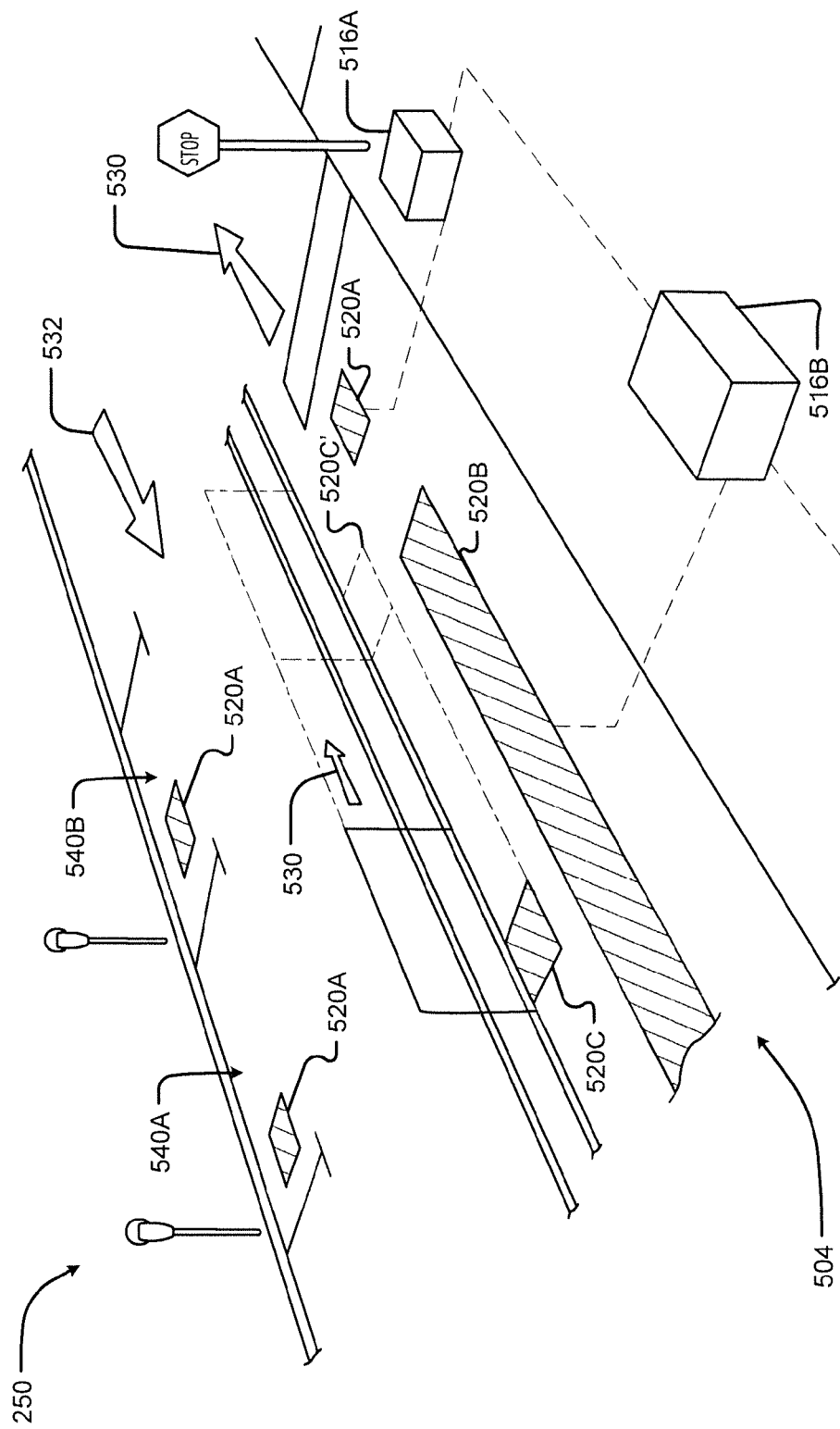
FIG. 5 shows charging areas associated with an environment in accordance with embodiments of the present disclosure.

FIG. 5 depicts a charging environment of a roadway charging system 250. The charging area may be in the roadway 504, on the roadway 504, or otherwise adjacent to the roadway 504, and/or combinations thereof. This static charging area 520B may allow a charge to be transferred even while the electrical vehicle 100 is moving. For example, the static charging area 520B may include a charging transmitter (e.g., conductor, etc.) that provides a transfer of energy when in a suitable range of a receiving unit (e.g., an inductor pick up, etc.). In this example, the receiving unit may be a part of the charging panel associated with the electrical vehicle 100.

The static charging areas 520A, 520B may be positioned a static area such as a designated spot, pad, parking space 540A, 540B, traffic controlled space (e.g., an area adjacent to a stop sign, traffic light, gate, etc.), portion of a building, portion of a structure, etc., and/or combinations thereof. Some static charging areas may require that the electric vehicle 100 is stationary before a charge, or electrical energy transfer, is initiated. The charging of vehicle 100 may occur by any of several means comprising a plug or other protruding feature. The power source 516A, 516B may include a receptacle or other receiving feature, and/or vice versa.

The charging area may be a moving charging area 520C. Moving charging areas 520C may include charging areas associated with one or more portions of a vehicle, a robotic charging device, a tracked charging device, a rail charging device, etc., and/or combinations thereof. In a moving charging area 520C, the electrical vehicle 100 may be configured to receive a charge, via a charging panel, while the vehicle 100 is moving and/or while the vehicle 100 is stationary. In some embodiments, the electrical vehicle 100 may synchronize to move at the same speed, acceleration, and/or path as the moving charging area 520C. In one embodiment, the moving charging area 520C may synchronize to move at the same speed, acceleration, and/or path as the electrical vehicle 100. In any event, the synchronization may be based on an exchange of information communicated across a communications channel between the electric vehicle 100 and the charging area 520C. Additionally or alternatively, the synchronization may be based on information associated with a movement of the electric vehicle 100 and/or the moving charging area 520C. In some embodiments, the moving charging area 520C may be configured to move along a direction or path 532 from an origin position to a destination position 520C'.

In some embodiments, a transformer may be included to convert a power setting associated with a main power supply to a power supply used by the charging areas 520A-C. For example, the transformer may increase or decrease a voltage associated with power supplied via one or more power transmission lines.

Figure 6:
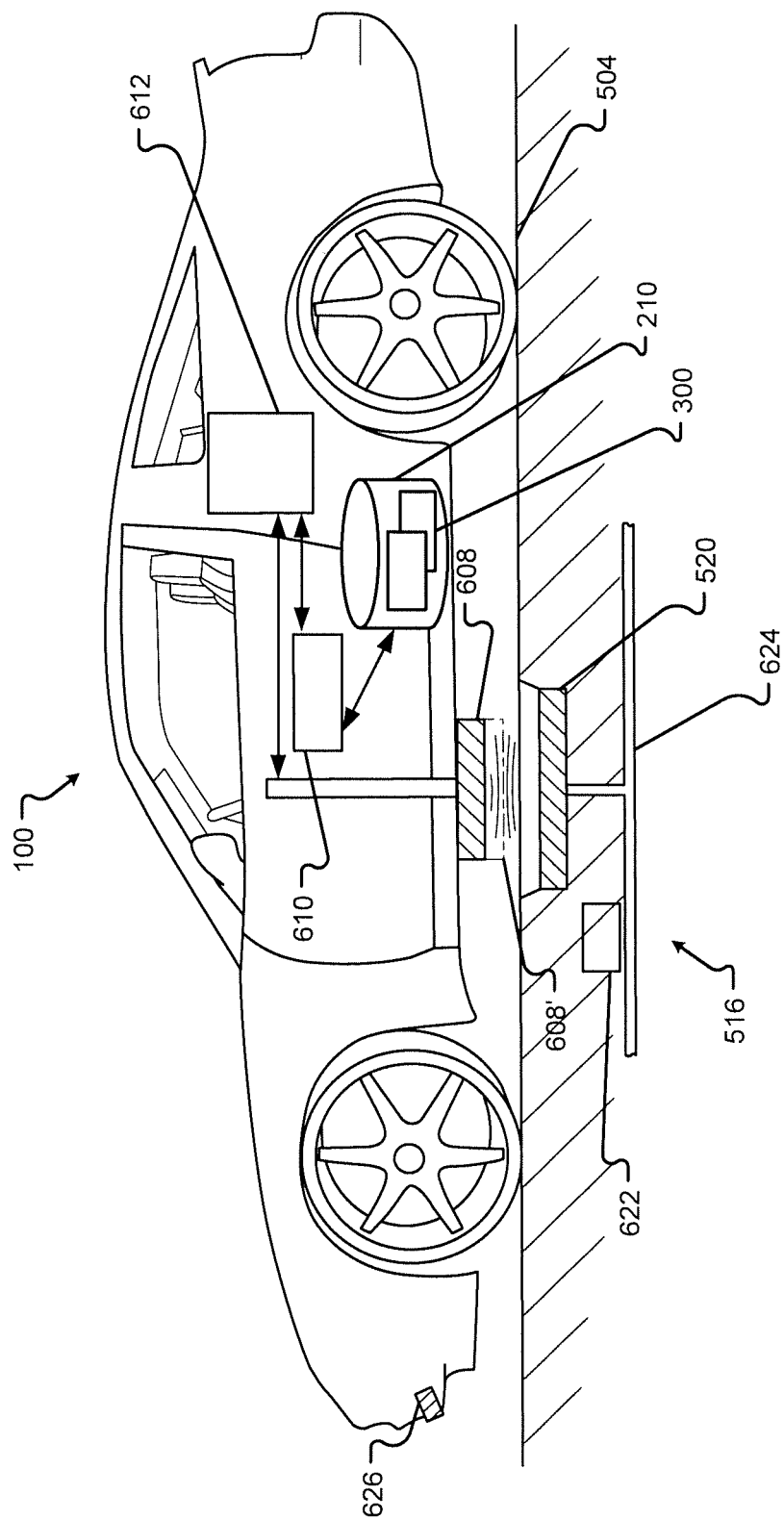
FIG. 6 shows a vehicle in a roadway charging environment in accordance with embodiments of the present disclosure.

Referring to FIG. 6, a vehicle 100 is shown in a charging environment in accordance with embodiments of the present disclosure. The system 10 comprises a vehicle 100, an electrical storage unit 612, an external power source 516 able to provide a charge to the vehicle 100, a charging panel 608 mounted on the vehicle 100 and in electrical communication with the electrical storage unit 612, and a vehicle charging panel controller 610. The charging panel controller 610 may determine if the electrical storage unit requires charging and if conditions allow for deployment of a charging panel. The vehicle charging panel 608 may operate in at least a retracted state and a deployed state (608 and 608' as shown is FIG. 6), and is movable by way of an armature.

The charging panel controller 610 may receive signals from vehicle sensors 626 to determine, for example, if a hazard is present in the path of the vehicle 100 such that deployment of the vehicle charging panel 608 is inadvisable. The charging panel controller 610 may also query vehicle database 210 comprising data structures 300 to establish other required conditions for deployment. For example, the database may provide that a particular roadway does not provide a charging service or the charging service is inactive, wherein the charging panel 108 would not be deployed.

The power source 516 may include at least one electrical transmission line 624 and at least one power transmitter or charging area 520. During a charge, the charging panel 608 may serve to transfer energy from the power source 516 to at least one energy storage unit 612 (e.g., battery, capacitor, power cell, etc.) of the electric vehicle 100.

Figure 7:
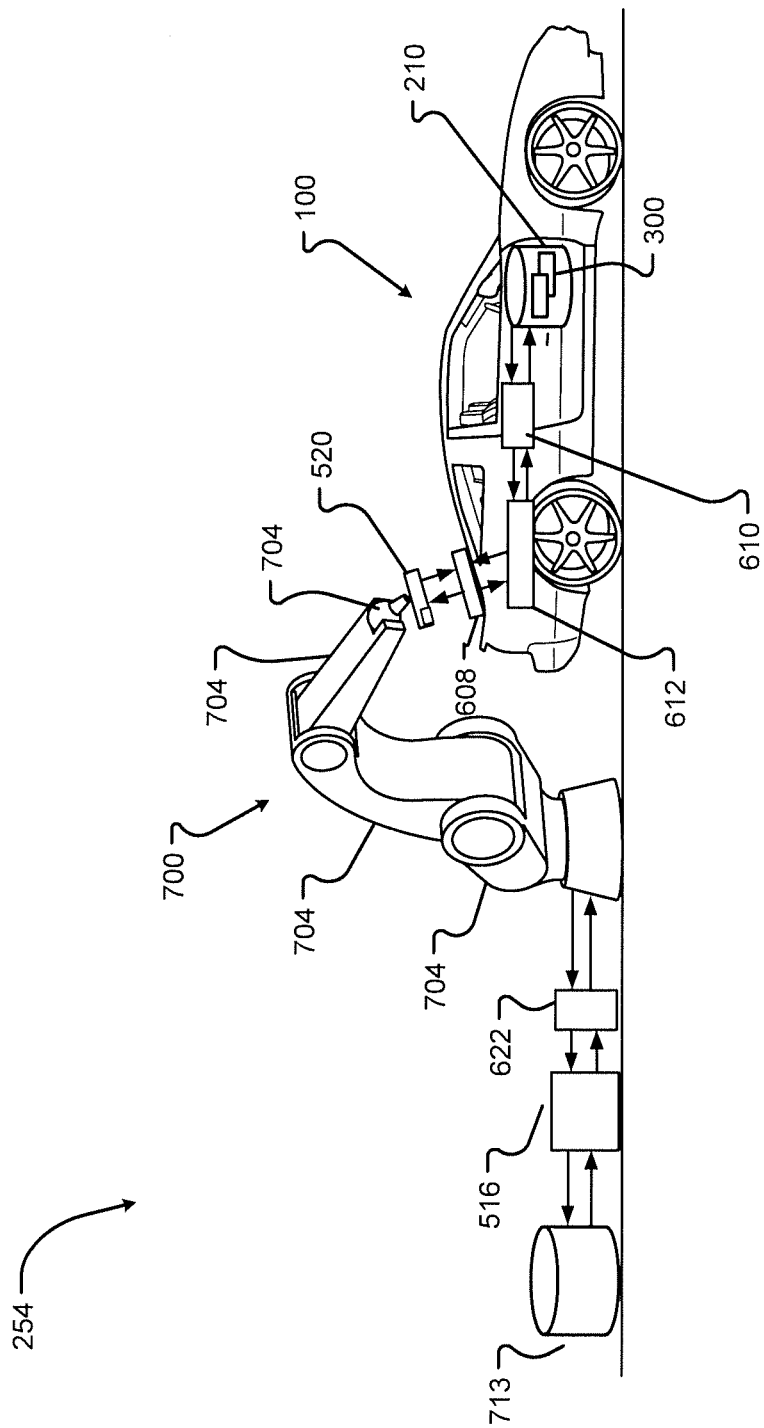
FIG. 7 shows a vehicle in a robotic charging station environment in accordance with another embodiment of the present disclosure.

FIG. 7 shows a vehicle 100 in a charging station environment 254 in accordance with another embodiment of the present disclosure. Generally, in this embodiment of the disclosure, charging occurs from a robotic unit 700.

Robotic charging unit 700 comprises one or more robotic unit arms 704, at least one robotic unit arm 704 interconnected with charging plate 520. The one or more robotic unit arms 704 manoeuver charging plate 520 relative to charging panel 608 of vehicle 100. Charging plate 520 is positioned to a desired or selectable separation distance, as assisted by a separation distance sensor disposed on charging plate 520. Charging plate 520 may remain at a finite separation distance from charging panel 608, or may directly contact charging panel (i.e. such that separation distance is zero). Charging may be by induction. In alternative embodiments, separation distance sensor is alternatively or additionally disposed on robotic arm 704. Vehicle 100 receives charging via charging panel 608 which in turn charges energy storage unit 612. Charging panel controller 610 is in communication with energy storage unit 612, charging panel 608, vehicle database 300, charge provider controller 622, and/or any one of elements of instrument panel 400.

Robotic unit further comprises, is in communication with and/or is interconnected with charge provider controller 622, power source 516 and a robotic unit database. Power source 516 supplies power, such as electrical power, to charge plate 520 to enable charging of vehicle 100 via charging panel 608. Controller 622 manoeuvers or operates robotic unit 704, either directly and/or completely or with assistance from a remote user, such as a driver or passenger in vehicle 100 by way of, in one embodiment, charging manual controller 432.

Figure 8:
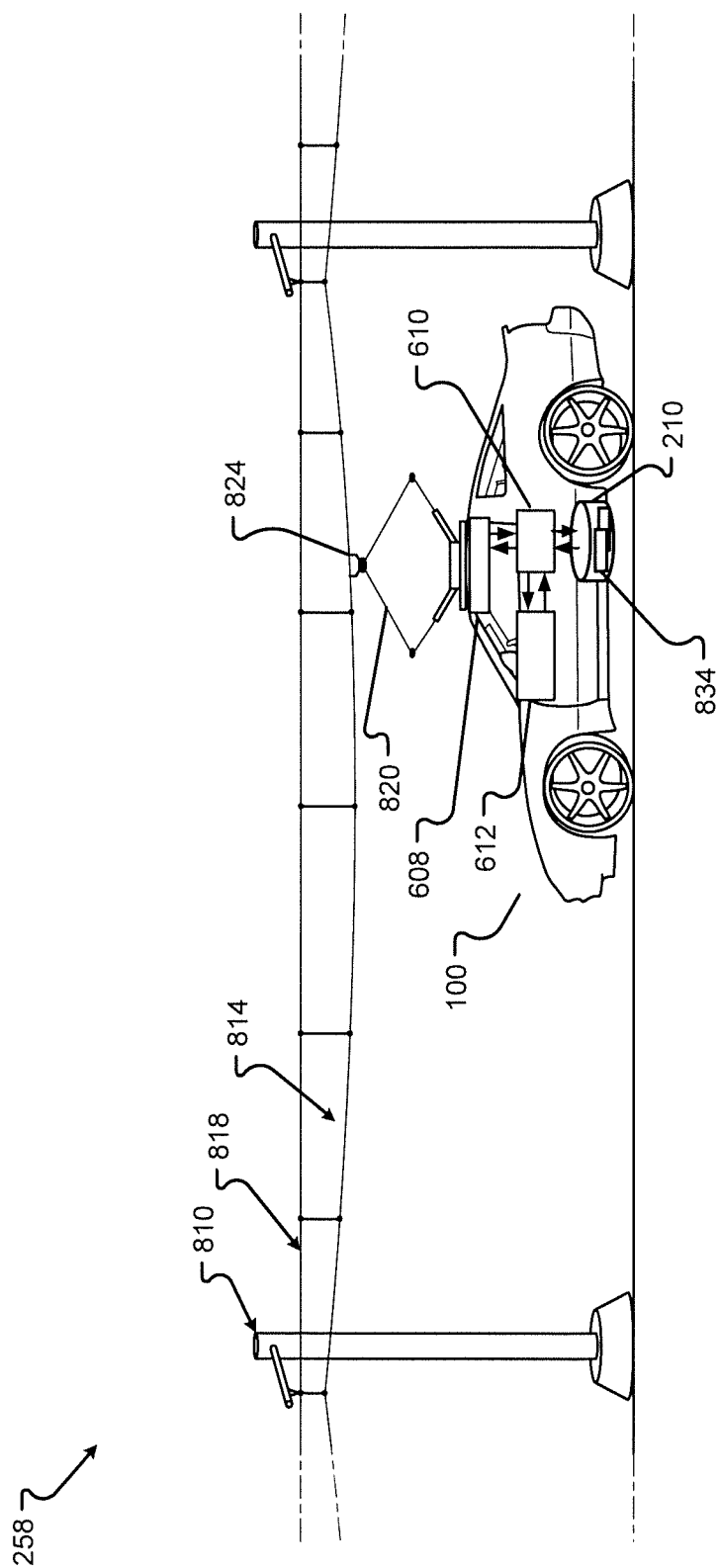
FIG. 8 shows a vehicle in an overhead charging environment in accordance with another embodiment of the present disclosure.

FIG. 8 shows a vehicle 100 in an overhead charging environment in accordance with another embodiment of the present disclosure. Generally, in this embodiment of the disclosure, charging occurs from an overhead towered charging system 258, similar to existing commuter rail systems. Such an overhead towered system 258 may be easier to build and repair compared to in-roadway systems. Generally, the disclosure includes a specially-designed overhead roadway charging system comprising an overhead charging cable or first wire 814 that is configured to engage an overhead contact 824 which provides charge to charging panel 608 which provides charge to vehicle energy storage unit 612. The overhead towered charging system 258 may further comprise second wire 818 to provide stability and structural strength to the roadway charging system 800. The first wire 814 and second wire 818 are strung between towers 810.

The overhead charging cable or first wire 814 is analogous to a contact wire used to provide charging to electric trains or other vehicles. An external source provides or supplies electrical power to the first wire 814. The charge provider comprises an energy source i.e. a provider battery and a provider charge circuit or controller in communication with the provider battery. The overhead charging cable or first wire 814 engages the overhead contact 824 which is in electrical communication with charge receiver panel 108. The overhead contact 824 may comprise any known means to connect to overhead electrical power cables, such as a pantograph 820, a bow collector, a trolley pole or any means known to those skilled in the art. Further disclosure regarding electrical power or energy transfer via overhead systems is found in US Pat. Publ. No. 2013/0105264 to Ruth entitled "Pantograph Assembly," the entire contents of which are incorporated by reference for all purposes. In one embodiment, the charging of vehicle 100 by overhead charging system 800 via overhead contact 824 is by any means know to those skilled in the art, to include those described in the above-referenced US Pat. Publ. No. 2013/0105264 to Ruth.

The overhead contact 824 presses against the underside of the lowest overhead wire of the overhead charging system, i.e. the overhead charging cable or first wire 814, aka the contact wire. The overhead contact 824 may be electrically conductive. Alternatively or additionally, the overhead contact 824 may be adapted to receive electrical power from overhead charging cable or first wire 814 by inductive charging.

In one embodiment, the receipt and/or control of the energy provided via overhead contact 824 (as connected to the energy storage unit 612) is provided by receiver charge circuit or charging panel controller 110.

Overhead contact 824 and/or charging panel 608 may be located anywhere on vehicle 100, to include, for example, the roof, side panel, trunk, hood, front or rear bumper of the charge receiver 100 vehicle, as long as the overhead contact 824 may engage the overhead charging cable or first wire 814. Charging panel 108 may be stationary (e.g. disposed on the roof of vehicle 100) or may be moveable, e.g. moveable with the pantograph 820. Pantograph 820 may be positioned in at least two states comprising retracted and extended. In the extended state pantograph 820 engages first wire 814 by way of the overhead contact 824. In the retracted state, pantograph 820 may typically reside flush with the roof of vehicle 100 and extend only when required for charging. Control of the charging and/or positioning of the charging plate 608, pantograph 820 and/or overhead contact 824 may be manual, automatic or semi-automatic (such as via controller 610); said control may be performed through a GUI engaged by driver or occupant of receiving vehicle 100 and/or driver or occupant of charging vehicle.

Figure 9:
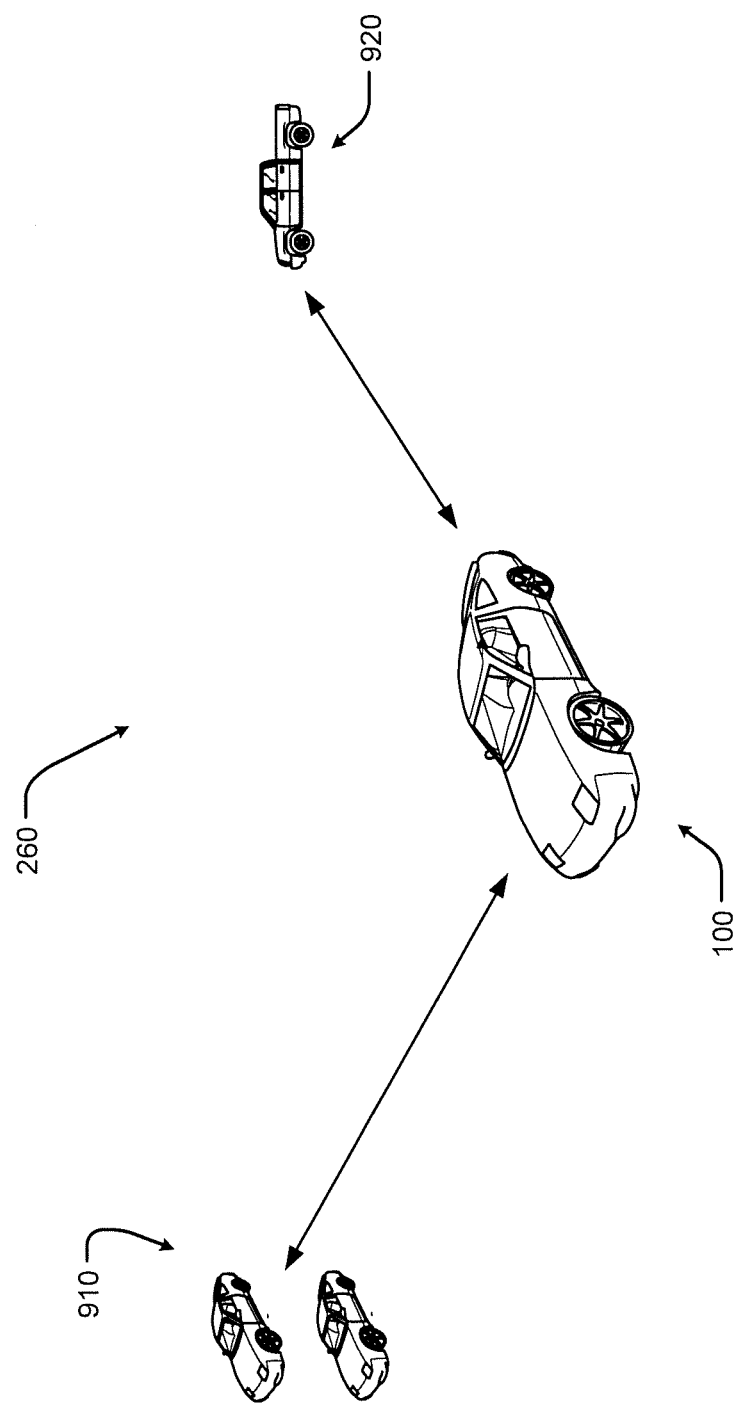
FIG. 9 shows a vehicle in a roadway environment comprising roadway vehicles in accordance with another embodiment of the present disclosure.

FIG. 9 shows a vehicle in a roadway environment comprising roadway vehicles 260 in accordance with another embodiment of the present disclosure. Roadway vehicles 260 comprise roadway passive vehicles 910 and roadway active vehicles 920. Roadway passive vehicles 910 comprise vehicles that are operating on the roadway of vehicle 100 but do no cooperatively or actively engage with vehicle 100. Stated another way, roadway passive vehicles 910 are simply other vehicles operating on the roadway with the vehicle 100 and must be, among other things, avoided (e.g., to include when vehicle 100 is operating in an autonomous or semi-autonomous manner). In contrast, roadway active vehicles 920 comprise vehicles that are operating on the roadway of vehicle 100 and have the capability to, or actually are, actively engaging with vehicle 100. For example, the emergency charging vehicle system 270 is a roadway active vehicle 920 in that it may cooperate or engage with vehicle 100 to provide charging. In some embodiments, vehicle 100 may exchange data with a roadway active vehicle 920 such as, for example, data regarding charging types available to the roadway active vehicle 920.

Figure 10:
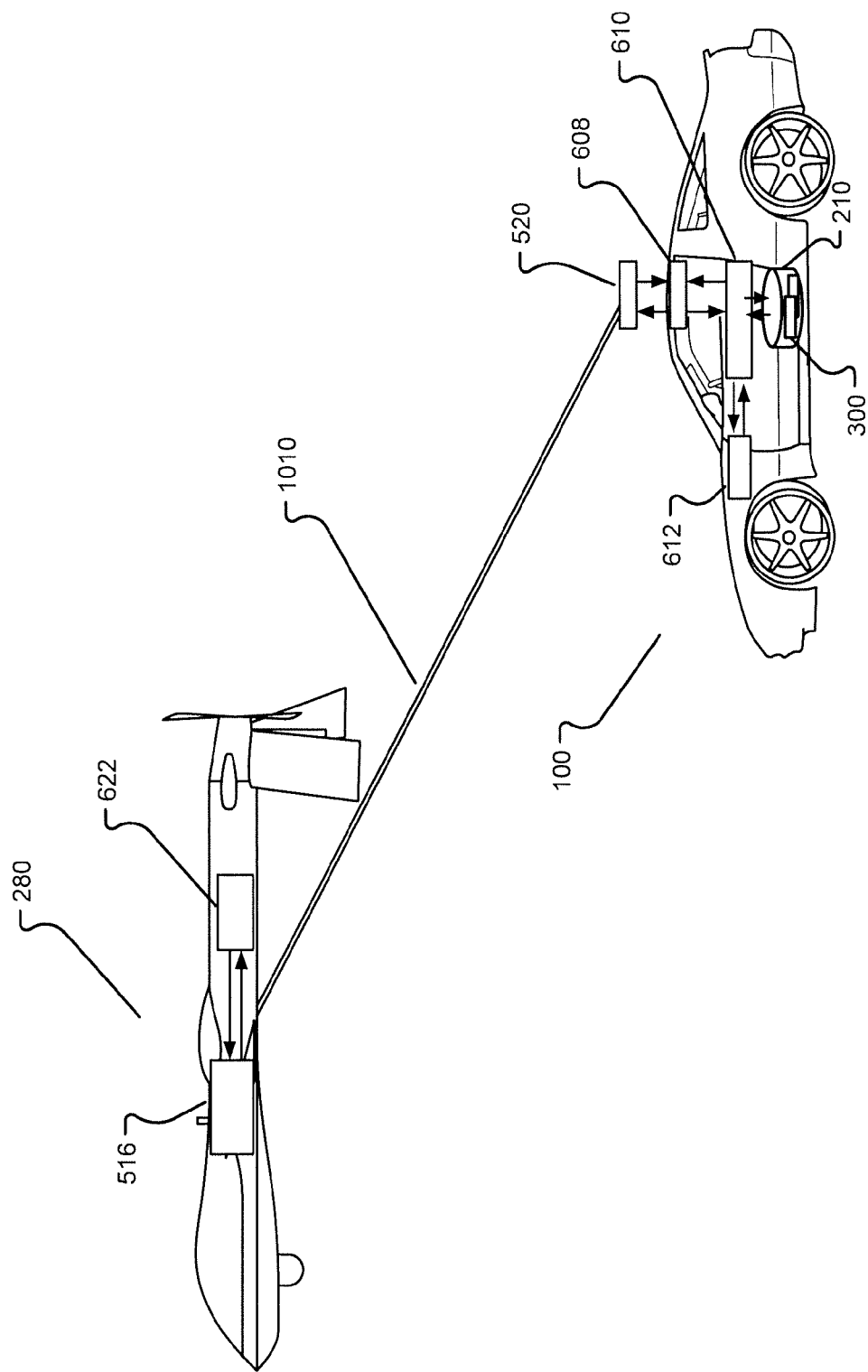
FIG. 10 shows a vehicle in an aerial vehicle charging environment in accordance with another embodiment of the present disclosure.

FIG. 10 shows a vehicle in an aerial vehicle charging environment in accordance with another embodiment of the present disclosure. Generally, this embodiment involves an aerial vehicle ("AV"), such as an Unmanned Aerial Vehicle (UAV), flying over or near a vehicle to provide a charge. The UAV may also land on the car to provide an emergency (or routine) charge. Such a charging scheme may be particularly suited for operations in remote areas, in high traffic situations, and/or when the car is moving. The AV may be a specially-designed UAV, aka RPV or drone, with a charging panel that can extend from the AV to provide a charge. The AV may include a battery pack and a charging circuit to deliver a charge to the vehicle. The AV may be a manned aerial vehicle, such as a piloted general aviation aircraft, such as a Cessna 172.

With reference to FIG. 10, an exemplar embodiment of a vehicle charging system 100 comprising a charge provider configured as an aerial vehicle 280, the aerial vehicle 280 comprising a power source 516 and charge provider controller 622. The AV may be semi-autonomous or fully autonomous. The AV may have a remote pilot/operator providing control inputs. The power source 516 is configured to provide a charge to a charging panel 608 of vehicle 100. The power source 516 is in communication with the charge provider controller 622. The aerial vehicle 280 provides a tether 1010 to deploy or extend charging plate 520 near to charging panel 608. The tether 1010 may comprise a chain, rope, rigid or semi-rigid tow bar or any means to position charging plate 520 near charging panel 608. For example, tether 1010 may be similar to a refueling probe used by airborne tanker aircraft when refueling another aircraft.

In one embodiment, the charging plate 520 is not in physical interconnection to AV 280, that is, there is no tether 1010. In this embodiment, the charging plate 520 is positioned and controlled by AV 280 by way of a controller on AV 280 or in communication with AV 280.

In one embodiment, the charging plate 520 position and/or characteristics (e.g. charging power level, flying separation distance, physical engagement on/off) are controlled by vehicle 100 and/or a user in or driver of vehicle 100.

Charge or power output of power source 516 is provided or transmitted to charger plate 620 by way of a charging cable or wire, which may be integral to tether 1010. In one embodiment, the charging cable is non-structural, that is, it provides zero or little structural support to the connection between AV 280 and charger plate 520.

Charging panel 608 of vehicle 100 receives power from charger plate 520. Charging panel 608 and charger plate 520 may be in direct physical contact (termed a "contact" charger configuration) or not in direct physical contact (termed a "flyer" charger configuration), but must be at or below a threshold (separation) distance to enable charging, such as by induction. Energy transfer or charging from the charger plate 520 to the charging panel 608 is inductive charging (i.e. use of an EM field to transfer energy between two objects). The charging panel 608 provides received power to energy storage unit 612 by way of charging panel controller 610. Charging panel controller 610 is in communication with vehicle database 210, vehicle database 210 comprising an AV charging data structure.

Charging panel 508 may be located anywhere on vehicle 100, to include, for example, the roof, side panel, trunk, hood, front or rear bumper and wheel hub of vehicle 100. Charging panel 608 is mounted on the roof of vehicle 100 in the embodiment of FIG. 10. In some embodiments, charging panel 608 may be deployable, i.e. may extend or deploy only when charging is needed. For example, charging panel 608 may typically reside flush with the roof of vehicle 100 and extend when required for charging. Similarly, charger plate 520 may, in one embodiment, not be connected to AV 280 by way of tether 1010 and may instead be mounted directly on the AV 280, to include, for example, the wing, empennage, undercarriage to include landing gear, and may be deployable or extendable when required. Tether 1010 may be configured to maneuver charging plate 520 to any position on vehicle 100 so as to enable charging. In one embodiment, the AV 280 may land on the vehicle 100 so as to enable charging through direct contact (i.e. the aforementioned contact charging configuration) between the charging plate 520 and the charging panel 608 of vehicle 100. Charging may occur while both AV 280 and vehicle 100 are moving, while both vehicle 100 and AV 280 are not moving (i.e., vehicle 100 is parked and AV 280 lands on top of vehicle 100), or while vehicle 100 is parked and AV 280 is hovering or circling above. Control of the charging and/or positioning of the charging plate 520 may be manual, automatic or semi-automatic; said control may be performed through a GUI engaged by driver or occupant of receiving vehicle 100 and/or driver or occupant of charging AV 280.

Figure 11:
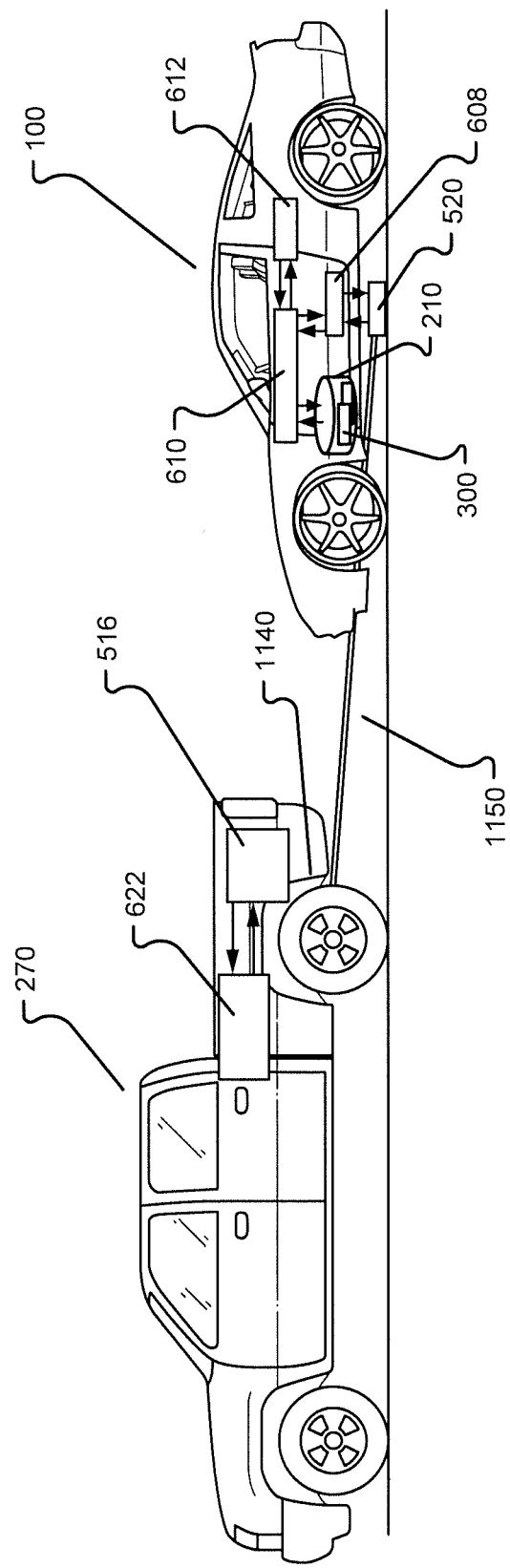
FIG. 11 shows a vehicle in an emergency charging environment in accordance with embodiments of the present disclosure.

FIG. 11 is an embodiment of a vehicle emergency charging system comprising an emergency charging vehicle 270 and charge receiver vehicle 100 is disclosed. The emergency charging vehicle 270 is a road vehicle, such as a pick-up truck, as shown in FIG. 11. The emergency charging vehicle 270 is configured to provide a charge to a charge receiver vehicle 100, such as an automobile. The emergency charging vehicle 270 comprises an energy source i.e. a charging power source 516 and a charge provider controller 622 in communication with the charging power source 516. The emergency charging vehicle 270 provides a towed and/or articulated charger plate 520, as connected to the emergency charging vehicle 270 by connector 1150. The connector 1150 may comprise a chain, rope, rigid or semi-rigid tow bar or any means to position charger plate 520 near the charging panel 608 of vehicle 100. Charge or power output of charging power source 516 is provided or transmitted to charger plate 520 by way of charging cable or wire 1140. In one embodiment, the charging cable 1140 is non-structural, that is, it provides little or no structural support to the connection between emergency charging vehicle 270 and charging panel 608. Charging panel 608 (of vehicle 100) receives power from charger plate 520. Charger plate 520 and charging panel 608 may be in direct physical contact or not in direct physical contact, but must be at or below a threshold separation distance to enable charging, such as by induction. Charger plate 520 may comprise wheels or rollers so as to roll along roadway surface. Charger plate 520 may also not contact the ground surface and instead be suspended above the ground; such a configuration may be termed a "flying" configuration. In the flying configuration, charger plate may form an aerodynamic surface to, for example, facilitate stability and control of the positioning of the charging plate 520. Energy transfer or charging from the charger plate 520 to the charge receiver panel 608 is through inductive charging (i.e. use of an EM field to transfer energy between two objects). The charging panel 608 provides received power to energy storage unit 612 directly or by way of charging panel controller 610. In one embodiment, the receipt and/or control of the energy provided via the charging panel 608 is provided by charging panel controller 610.

Charging panel controller 610 may be located anywhere on charge receiver vehicle 100, to include, for example, the roof, side panel, trunk, hood, front or rear bumper and wheel hub of charge receiver 100 vehicle. In some embodiments, charging panel 608 may be deployable, i.e. may extend or deploy only when charging is needed. For example, charging panel 608 may typically stow flush with the lower plane of vehicle 100 and extend when required for charging. Similarly, charger plate 520 may, in one embodiment, not be connected to the lower rear of the emergency charging vehicle 270 by way of connector 1150 and may instead be mounted on the emergency charging vehicle 270, to include, for example, the roof, side panel, trunk, hood, front or rear bumper and wheel hub of emergency charging vehicle 270. Connector 1150 may be configured to maneuver connector plate 520 to any position on emergency charging vehicle 270 so as to enable charging. Control of the charging and/or positioning of the charging plate may be manual, automatic or semi-automatic; said control may be performed through a GUI engaged by driver or occupant of receiving vehicle and/or driver or occupant of charging vehicle.

Figure 12:
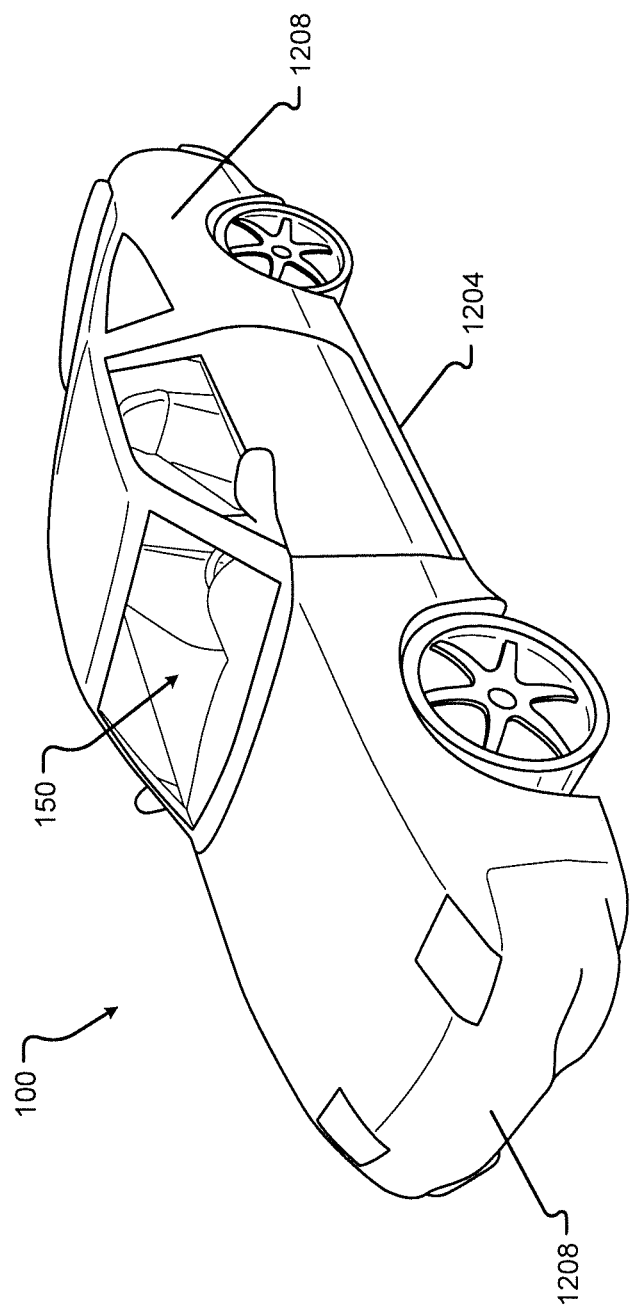
FIG. 12 is a perspective view of a vehicle in accordance with embodiments of the present disclosure.

FIG. 12 shows a perspective view of a vehicle 100 in accordance with embodiments of the present disclosure. Although shown in the form of a car, it should be appreciated that the vehicle 100 described herein may include any conveyance or model of a conveyance, where the conveyance was designed for the purpose of moving one or more tangible objects, such as people, animals, cargo, and the like. The term "vehicle" does not require that a conveyance moves or is capable of movement. Typical vehicles may include but are in no way limited to cars, trucks, motorcycles, busses, automobiles, trains, railed conveyances, boats, ships, marine conveyances, submarine conveyances, airplanes, space craft, flying machines, human-powered conveyances, and the like. In any event, the vehicle 100 may include a frame 1204 and one or more body panels 1208 mounted or affixed thereto. The vehicle 100 may include one or more interior components (e.g., components inside an interior space 150, or user space, of a vehicle 100, etc.), exterior components (e.g., components outside of the interior space 150, or user space, of a vehicle 100, etc.), drive systems, controls systems, structural components.

Figure 13:
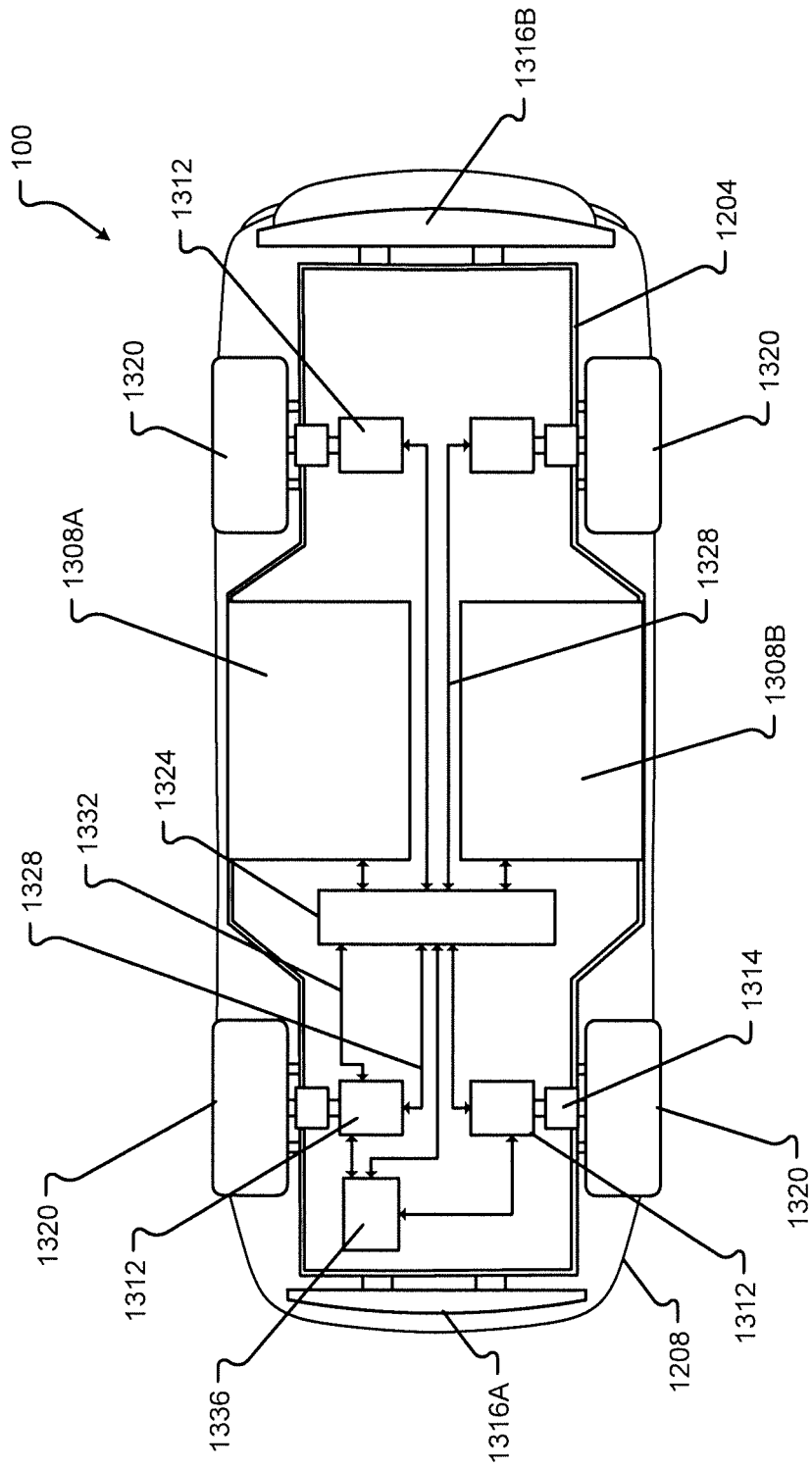
FIG. 13 is a plan view of a vehicle in accordance with at least some embodiments of the present disclosure.

Referring now to FIG. 13, a plan view of a vehicle 100 will be described in accordance with embodiments of the present disclosure. As provided above, the vehicle 100 may comprise a number of electrical and/or mechanical systems, subsystems, etc. The mechanical systems of the vehicle 100 can include structural, power, safety, and communications subsystems, to name a few. While each subsystem may be described separately, it should be appreciated that the components of a particular subsystem may be shared between one or more other subsystems of the vehicle 100.

The structural subsystem includes the frame 1204 of the vehicle 100. The frame 1204 may comprise a separate frame and body construction (i.e., body-on-frame construction), a unitary frame and body construction (i.e., a unibody construction), or any other construction defining the structure of the vehicle 100. The frame 1204 may be made from one or more materials including, but in no way limited to steel, titanium, aluminum, carbon fiber, plastic, polymers, etc., and/or combinations thereof. In some embodiments, the frame 1204 may be formed, welded, fused, fastened, pressed, etc., combinations thereof, or otherwise shaped to define a physical structure and strength of the vehicle 100. In any event, the frame 1204 may comprise one or more surfaces, connections, protrusions, cavities, mounting points, tabs, slots, or other features that are configured to receive other components that make up the vehicle 100. For example, the body panels, powertrain subsystem, controls systems, interior components, communications subsystem, and safety subsystem may interconnect with, or attach to, the frame 1204 of the vehicle 100.

The frame 1204 may include one or more modular system and/or subsystem connection mechanisms. These mechanisms may include features that are configured to provide a selectively interchangeable interface for one or more of the systems and/or subsystems described herein. The mechanisms may provide for a quick exchange, or swapping, of components while providing enhanced security and adaptability over conventional manufacturing or attachment. For instance, the ability to selectively interchange systems and/or subsystems in the vehicle 100 allow the vehicle 100 to adapt to the ever-changing technological demands of society and advances in safety. Among other things, the mechanisms may provide for the quick exchange of batteries, capacitors, power sources 1308A, 1308B, motors 1312, engines, safety equipment, controllers, user interfaces, interiors exterior components, body panels 1208, bumpers 1316, sensors, etc., and/or combinations thereof. Additionally or alternatively, the mechanisms may provide unique security hardware and/or software embedded therein that, among other things, can prevent fraudulent or low quality construction replacements from being used in the vehicle 100. Similarly, the mechanisms, subsystems, and/or receiving features in the vehicle 100 may employ poka-yoke, or mistake-proofing, features that ensure a particular mechanism is always interconnected with the vehicle 100 in a correct position, function, etc.

By way of example, complete systems or subsystems may be removed and/or replaced from a vehicle 100 utilizing a single minute exchange principle. In some embodiments, the frame 1204 may include slides, receptacles, cavities, protrusions, and/or a number of other features that allow for quick exchange of system components. In one embodiment, the frame 1204 may include tray or ledge features, mechanical interconnection features, locking mechanisms, retaining mechanisms, etc., and/or combinations thereof. In some embodiments, it may be beneficial to quickly remove a used power source 1308A, 1308B (e.g., battery unit, capacitor unit, etc.) from the vehicle 100 and replace the used power source 1308A, 1308B with a charged power source. Continuing this example, the power source 1308A, 1308B may include selectively interchangeable features that interconnect with the frame 1204 or other portion of the vehicle 100. For instance, in a power source 1308A, 1308B replacement, the quick release features may be configured to release the power source 1308A, 1308B from an engaged position and slide or move away from the frame 1204 of a vehicle 100. Once removed, the power source 1308A, 1308B may be replaced (e.g., with a new power source, a charged power source, etc.) by engaging the replacement power source into a system receiving position adjacent to the vehicle 100. In some embodiments, the vehicle 100 may include one or more actuators configured to position, lift, slide, or otherwise engage the replacement power source with the vehicle 100. In one embodiment, the replacement power source may be inserted into the vehicle 100 or vehicle frame 1204 with mechanisms and/or machines that are external or separate from the vehicle 100.

In some embodiments, the frame 1204 may include one or more features configured to selectively interconnect with other vehicles and/or portions of vehicles. These selectively interconnecting features can allow for one or more vehicles to selectively couple together and decouple for a variety of purposes. For example, it is an aspect of the present disclosure that a number of vehicles may be selectively coupled together to share energy, increase power output, provide security, decrease power consumption, provide towing services, and/or provide a range of other benefits. Continuing this example, the vehicles may be coupled together based on travel route, destination, preferences, settings, sensor information, and/or some other data. The coupling may be initiated by at least one controller of the vehicle and/or traffic control system upon determining that a coupling is beneficial to one or more vehicles in a group of vehicles or a traffic system. As can be appreciated, the power consumption for a group of vehicles traveling in a same direction may be reduced or decreased by removing any aerodynamic separation between vehicles. In this case, the vehicles may be coupled together to subject only the foremost vehicle in the coupling to air and/or wind resistance during travel. In one embodiment, the power output by the group of vehicles may be proportionally or selectively controlled to provide a specific output from each of the one or more of the vehicles in the group.

The interconnecting, or coupling, features may be configured as electromagnetic mechanisms, mechanical couplings, electromechanical coupling mechanisms, etc., and/or combinations thereof. The features may be selectively deployed from a portion of the frame 1204 and/or body of the vehicle 100. In some cases, the features may be built into the frame 1204 and/or body of the vehicle 100. In any event, the features may deploy from an unexposed position to an exposed position or may be configured to selectively engage/disengage without requiring an exposure or deployment of the mechanism from the frame 1204 and/or body. In some embodiments, the interconnecting features may be configured to interconnect one or more of power, communications, electrical energy, fuel, and/or the like. One or more of the power, mechanical, and/or communications connections between vehicles may be part of a single interconnection mechanism. In some embodiments, the interconnection mechanism may include multiple connection mechanisms. In any event, the single interconnection mechanism or the interconnection mechanism may employ the poka-yoke features as described above.

The power system of the vehicle 100 may include the powertrain, power distribution system, accessory power system, and/or any other components that store power, provide power, convert power, and/or distribute power to one or more portions of the vehicle 100. The powertrain may include the one or more electric motors 1312 of the vehicle 100. The electric motors 1312 are configured to convert electrical energy provided by a power source into mechanical energy. This mechanical energy may be in the form of a rotational or other output force that is configured to propel or otherwise provide a motive force for the vehicle 100.

In some embodiments, the vehicle 100 may include one or more drive wheels 1320 that are driven by the one or more electric motors 1312 and motor controllers 1314. In some cases, the vehicle 100 may include an electric motor 1312 configured to provide a driving force for each drive wheel 1320. In other cases, a single electric motor 1312 may be configured to share an output force between two or more drive wheels 1320 via one or more power transmission components. It is an aspect of the present disclosure that the powertrain include one or more power transmission components, motor controllers 1314, and/or power controllers that can provide a controlled output of power to one or more of the drive wheels 1320 of the vehicle 100. The power transmission components, power controllers, or motor controllers 1314 may be controlled by at least one other vehicle controller described herein.

As provided above, the powertrain of the vehicle 100 may include one or more power sources 1308A, 1308B. These one or more power sources 1308A, 1308B may be configured to provide drive power, system and/or subsystem power, accessory power, etc. While described herein as a single power source 1308 for sake of clarity, embodiments of the present disclosure are not so limited. For example, it should be appreciated that independent, different, or separate power sources 1308A, 1308B may provide power to various systems of the vehicle 100. For instance, a drive power source may be configured to provide the power for the one or more electric motors 1312 of the vehicle 100, while a system power source may be configured to provide the power for one or more other systems and/or subsystems of the vehicle 100. Other power sources may include an accessory power source, a backup power source, a critical system power source, and/or other separate power sources. Separating the power sources 1308A, 1308B in this manner may provide a number of benefits over conventional vehicle systems. For example, separating the power sources 1308A, 1308B allow one power source 1308 to be removed and/or replaced independently without requiring that power be removed from all systems and/or subsystems of the vehicle 100 during a power source 1308 removal/replacement. For instance, one or more of the accessories, communications, safety equipment, and/or backup power systems, etc., may be maintained even when a particular power source 1308A, 1308B is depleted, removed, or becomes otherwise inoperable.

In some embodiments, the drive power source may be separated into two or more cells, units, sources, and/or systems. By way of example, a vehicle 100 may include a first drive power source 1308A and a second drive power source 1308B. The first drive power source 1308A may be operated independently from or in conjunction with the second drive power source 1308B and vice versa. Continuing this example, the first drive power source 1308A may be removed from a vehicle while a second drive power source 1308B can be maintained in the vehicle 100 to provide drive power. This approach allows the vehicle 100 to significantly reduce weight (e.g., of the first drive power source 1308A, etc.) and improve power consumption, even if only for a temporary period of time. In some cases, a vehicle 100 running low on power may automatically determine that pulling over to a rest area, emergency lane, and removing, or "dropping off," at least one power source 1308A, 1308B may reduce enough weight of the vehicle 100 to allow the vehicle 100 to navigate to the closest power source replacement and/or charging area. In some embodiments, the removed, or "dropped off," power source 1308A may be collected by a collection service, vehicle mechanic, tow truck, or even another vehicle or individual.

The power source 1308 may include a GPS or other geographical location system that may be configured to emit a location signal to one or more receiving entities. For instance, the signal may be broadcast or targeted to a specific receiving party. Additionally or alternatively, the power source 1308 may include a unique identifier that may be used to associate the power source 1308 with a particular vehicle 100 or vehicle user. This unique identifier may allow an efficient recovery of the power source 1308 dropped off. In some embodiments, the unique identifier may provide information for the particular vehicle 100 or vehicle user to be billed or charged with a cost of recovery for the power source 1308.

The power source 1308 may include a charge controller 1324 that may be configured to determine charge levels of the power source 1308, control a rate at which charge is drawn from the power source 1308, control a rate at which charge is added to the power source 1308, and/or monitor a health of the power source 1308 (e.g., one or more cells, portions, etc.). In some embodiments, the charge controller 1324 or the power source 1308 may include a communication interface. The communication interface can allow the charge controller 1324 to report a state of the power source 1308 to one or more other controllers of the vehicle 100 or even communicate with a communication device separate and/or apart from the vehicle 100. Additionally or alternatively, the communication interface may be configured to receive instructions (e.g., control instructions, charge instructions, communication instructions, etc.) from one or more other controllers of the vehicle 100 or a communication device that is separate and/or apart from the vehicle 100.

The powertrain includes one or more power distribution systems configured to transmit power from the power source 1308 to one or more electric motors 1312 in the vehicle 100. The power distribution system may include electrical interconnections 1328 in the form of cables, wires, traces, wireless power transmission systems, etc., and/or combinations thereof. It is an aspect of the present disclosure that the vehicle 100 include one or more redundant electrical interconnections 1332 of the power distribution system. The redundant electrical interconnections 1332 can allow power to be distributed to one or more systems and/or subsystems of the vehicle 100 even in the event of a failure of an electrical interconnection portion of the vehicle 100 (e.g., due to an accident, mishap, tampering, or other harm to a particular electrical interconnection, etc.). In some embodiments, a user of a vehicle 100 may be alerted via a user interface associated with the vehicle 100 that a redundant electrical interconnection 1332 is being used and/or damage has occurred to a particular area of the vehicle electrical system. In any event, the one or more redundant electrical interconnections 1332 may be configured along completely different routes than the electrical interconnections 1328 and/or include different modes of failure than the electrical interconnections 1328 to, among other things, prevent a total interruption power distribution in the event of a failure.

In some embodiments, the power distribution system may include an energy recovery system 1336. This energy recovery system 1336, or kinetic energy recovery system, may be configured to recover energy produced by the movement of a vehicle 100. The recovered energy may be stored as electrical and/or mechanical energy. For instance, as a vehicle 100 travels or moves, a certain amount of energy is required to accelerate, maintain a speed, stop, or slow the vehicle 100. In any event, a moving vehicle has a certain amount of kinetic energy. When brakes are applied in a typical moving vehicle, most of the kinetic energy of the vehicle is lost as the generation of heat in the braking mechanism. In an energy recovery system 1336, when a vehicle 100 brakes, at least a portion of the kinetic energy is converted into electrical and/or mechanical energy for storage. Mechanical energy may be stored as mechanical movement (e.g., in a flywheel, etc.) and electrical energy may be stored in batteries, capacitors, and/or some other electrical storage system. In some embodiments, electrical energy recovered may be stored in the power source 1308. For example, the recovered electrical energy may be used to charge the power source 1308 of the vehicle 100.

The vehicle 100 may include one or more safety systems. Vehicle safety systems can include a variety of mechanical and/or electrical components including, but in no way limited to, low impact or energy-absorbing bumpers 1316A, 1316B, crumple zones, reinforced body panels, reinforced frame components, impact bars, power source containment zones, safety glass, seatbelts, supplemental restraint systems, air bags, escape hatches, removable access panels, impact sensors, accelerometers, vision systems, radar systems, etc., and/or the like. In some embodiments, the one or more of the safety components may include a safety sensor or group of safety sensors associated with the one or more of the safety components. For example, a crumple zone may include one or more strain gages, impact sensors, pressure transducers, etc. These sensors may be configured to detect or determine whether a portion of the vehicle 100 has been subjected to a particular force, deformation, or other impact. Once detected, the information collected by the sensors may be transmitted or sent to one or more of a controller of the vehicle 100 (e.g., a safety controller, vehicle controller, etc.)

or a communication device associated with the vehicle 100 (e.g., across a communication network, etc.).

Figure 14:
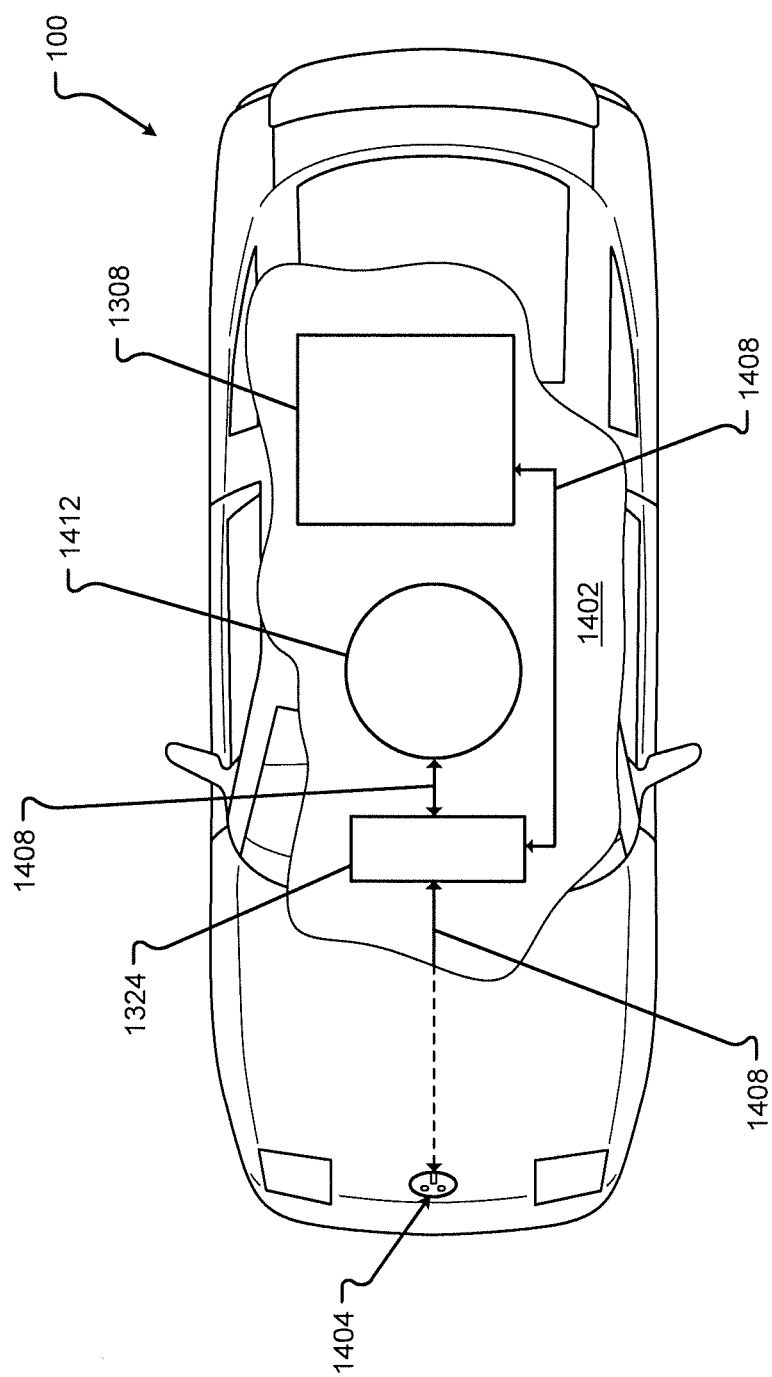
FIG. 14 is a plan view of a vehicle in accordance with embodiments of the present disclosure.

FIG. 14 shows a plan view of the vehicle 100 in accordance with embodiments of the present disclosure. In particular, FIG. 14 shows a broken section 1402 of a charging system for the vehicle 100. The charging system may include a plug or receptacle 1404 configured to receive power from an external power source (e.g., a source of power that is external to and/or separate from the vehicle 100, etc.). An example of an external power source may include the standard industrial, commercial, or residential power that is provided across power lines. Another example of an external power source may include a proprietary power system configured to provide power to the vehicle 100. In any event, power received at the plug/receptacle 1404 may be transferred via at least one power transmission interconnection 1408. Similar, if not identical, to the electrical interconnections 1328 described above, the at least one power transmission interconnection 1408 may be one or more cables, wires, traces, wireless power transmission systems, etc., and/or combinations thereof. Electrical energy in the form of charge can be transferred from the external power source to the charge controller 1324. As provided above, the charge controller 1324 may regulate the addition of charge to the power source 1308 of the vehicle 100 (e.g., until the power source 1308 is full or at a capacity, etc.).

In some embodiments, the vehicle 100 may include an inductive charging system and inductive charger 1412. The inductive charger 1412 may be configured to receive electrical energy from an inductive power source external to the vehicle 100. In one embodiment, when the vehicle 100 and/or the inductive charger 1412 is positioned over an inductive power source external to the vehicle 100, electrical energy can be transferred from the inductive power source to the vehicle 100. For example, the inductive charger 1412 may receive the charge and transfer the charge via at least one power transmission interconnection 1408 to the charge controller 1324 and/or the power source 1308 of the vehicle 100. The inductive charger 1412 may be concealed in a portion of the vehicle 100 (e.g., at least partially protected by the frame 1204, one or more body panels 1208, a shroud, a shield, a protective cover, etc., and/or combinations thereof) and/or may be deployed from the vehicle 100. In some embodiments, the inductive charger 1412 may be configured to receive charge only when the inductive charger 1412 is deployed from the vehicle 100. In other embodiments, the inductive charger 1412 may be configured to receive charge while concealed in the portion of the vehicle 100.

In addition to the mechanical components described herein, the vehicle 100 may include a number of user interface devices. The user interface devices receive and translate human input into a mechanical movement or electrical signal or stimulus. The human input may be one or more of motion (e.g., body movement, body part movement, in two-dimensional or three-dimensional space, etc.), voice, touch, and/or physical interaction with the components of the vehicle 100. In some embodiments, the human input may be configured to control one or more functions of the vehicle 100 and/or systems of the vehicle 100 described herein. User interfaces may include, but are in no way limited to, at least one graphical user interface of a display device, steering wheel or mechanism, transmission lever or button (e.g., including park, neutral, reverse, and/or drive positions, etc.), throttle control pedal or mechanism, brake control pedal or mechanism, power control switch, communications equipment, etc.

Figure 15:
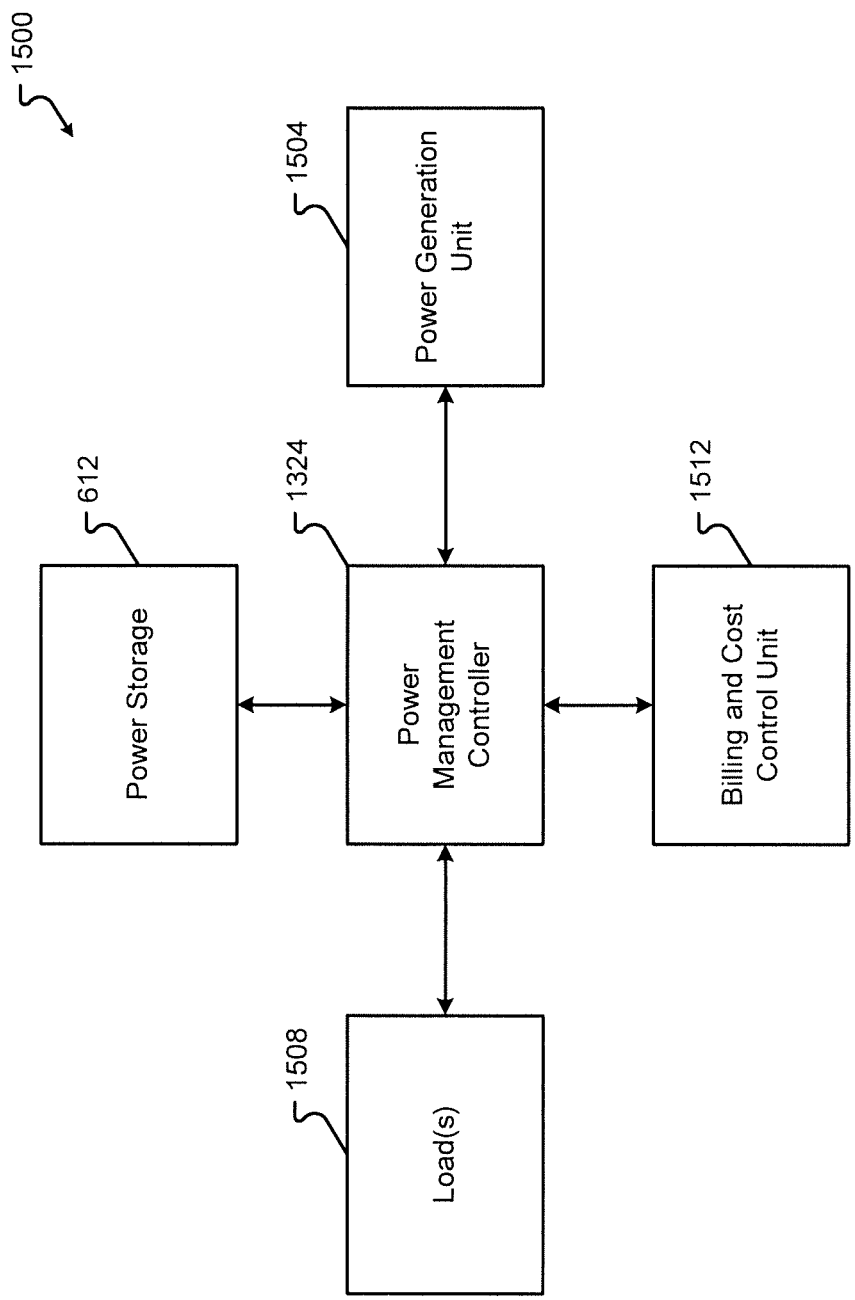
FIG. 15 is a block diagram of an embodiment of an electrical system of the vehicle.

An embodiment of the electrical system 1500 associated with the vehicle 100 may be as shown in FIG. 15. The electrical system 1500 can include power source(s) that generate power, power storage that stores power, and/or load(s) that consume power. Power sources may be associated with a power generation unit 1504. Power storage may be associated with a power storage system 612. Loads may be associated with loads 1508. The electrical system 1500 may be managed by a power management controller 1324. Further, the electrical system 1500 can include one or more other interfaces or controllers, which can include the billing and cost control unit 1512.

Figure 16:
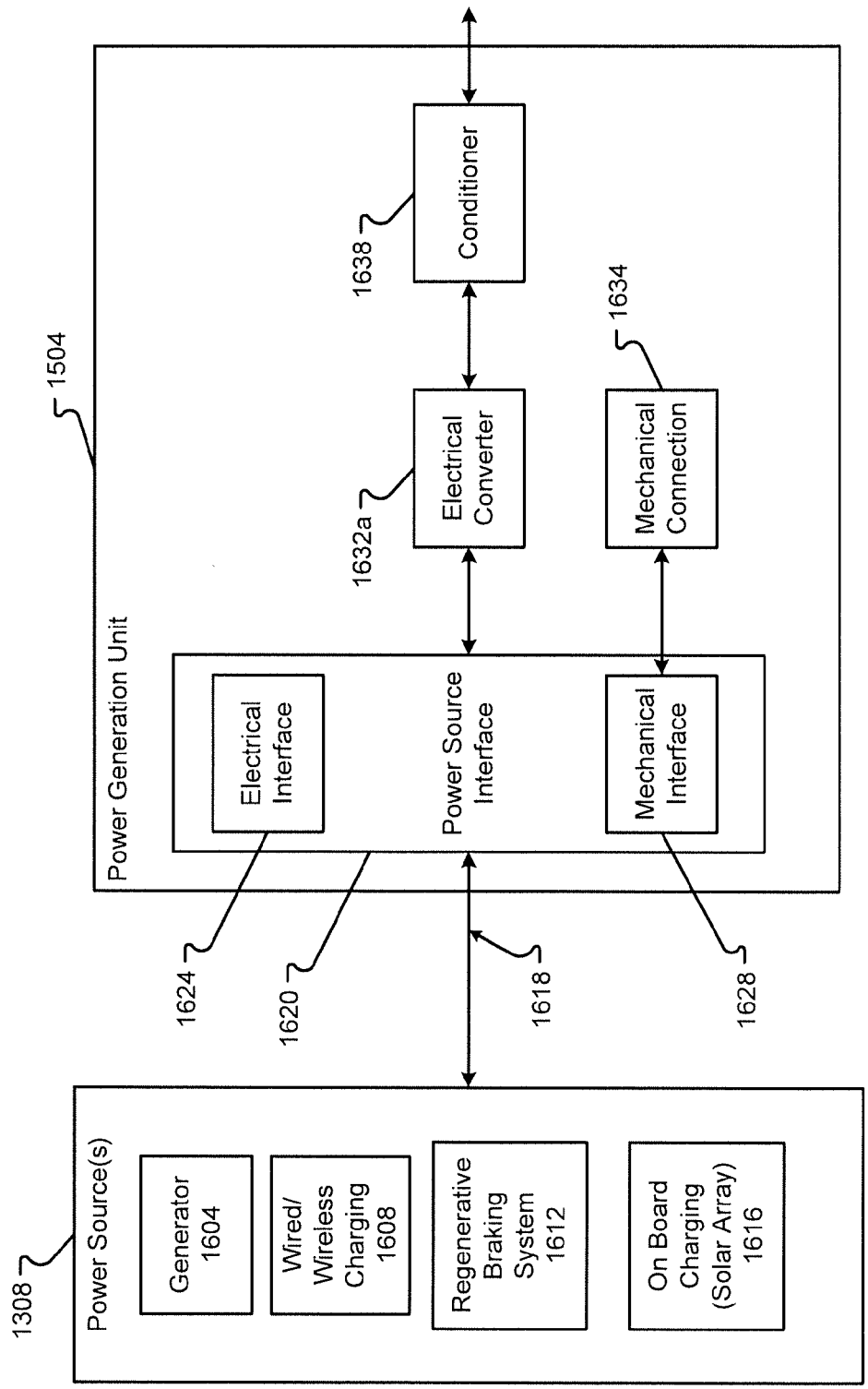
FIG. 16 is a block diagram of an embodiment of a power generation unit associated with the electrical system of the vehicle.

The power generation unit 1504 may be as described in conjunction with FIG. 16. The power storage component 612 may be as described in conjunction with FIG. 17. The loads 1508 may be as described in conjunction with FIG. 18.

The billing and cost control unit 1512 may interface with the power management controller 1324 to determine the amount of charge or power provided to the power storage 612 through the power generation unit 1504. The billing and cost control unit 1512 can then provide information for billing the vehicle owner. Thus, the billing and cost control unit 1512 can receive and/or send power information to third party system(s) regarding the received charge from an external source. The information provided can help determine an amount of money required, from the owner of the vehicle, as payment for the provided power. Alternatively, or in addition, if the owner of the vehicle provided power to another vehicle (or another device/system), that owner may be owed compensation for the provided power or energy, e.g., a credit.

The power management controller 1324 can be a computer or computing system(s) and/or electrical system with associated components, as described herein, capable of managing the power generation unit 1504 to receive power, routing the power to the power storage 612, and then providing the power from either the power generation unit 1504 and/or the power storage 612 to the loads 1508. Thus, the power management controller 1324 may execute programming that controls switches, devices, components, etc. involved in the reception, storage, and provision of the power in the electrical system 1500.

An embodiment of the power generation unit 1504 may be as shown in FIG. 16. Generally, the power generation unit 1504 may be electrically coupled to one or more power sources 1308. The power sources 1308 can include power sources internal and/or associated with the vehicle 100 and/or power sources external to the vehicle 100 to which the vehicle 100 electrically connects. One of the internal power sources can include an on board generator 1604. The generator 1604 may be an alternating current (AC) generator, a direct current (DC) generator or a self-excited generator. The AC generators can include induction generators, linear electric generators, and/or other types of generators. The DC generators can include homopolar generators and/or other types of generators. The generator 1604 can be brushless or include brush contacts and generate the electric field with permanent magnets or through induction. The generator 1604 may be mechanically coupled to a source of kinetic energy, such as an axle or some other power take-off. The generator 1604 may also have another mechanical coupling to an exterior source of kinetic energy, for example, a wind turbine.

Another power source 1308 may include wired or wireless charging 1608. The wireless charging system 1608 may include inductive and/or resonant frequency inductive charging systems that can include coils, frequency generators, controllers, etc. Wired charging may be any kind of grid-connected charging that has a physical connection, although, the wireless charging may be grid connected through a wireless interface. The wired charging system can include an connectors, wired interconnections, the controllers, etc. The wired and wireless charging systems 1608 can provide power to the power generation unit 1504 from external power sources 1308.

Internal sources for power may include a regenerative braking system 1612. The regenerative braking system 1612 can convert the kinetic energy of the moving car into electrical energy through a generation system mounted within the wheels, axle, and/or braking system of the vehicle 100. The regenerative braking system 1612 can include any coils, magnets, electrical interconnections, converters, controllers, etc. required to convert the kinetic energy into electrical energy.

Another source of power 1308, internal to or associated with the vehicle 100, may be a solar array 1616. The solar array 1616 may include any system or device of one or more solar cells mounted on the exterior of the vehicle 100 or integrated within the body panels of the vehicle 100 that provides or converts solar energy into electrical energy to provide to the power generation unit 1504.

The power sources 1308 may be connected to the power generation unit 1504 through an electrical interconnection 1618. The electrical interconnection 1618 can include any wire, interface, bus, etc. between the one or more power sources 1308 and the power generation unit 1504.

The power generation unit 1504 can also include a power source interface 1620. The power source interface 1620 can be any type of physical and/or electrical interface used to receive the electrical energy from the one or more power sources 1308; thus, the power source interface 1620 can include an electrical interface 1624 that receives the electrical energy and a mechanical interface 1628 which may include wires, connectors, or other types of devices or physical connections. The mechanical interface 1608 can also include a physical/electrical connection 1634 to the power generation unit 1504.

The electrical energy from the power source 1308 can be processed through the power source interface 1624 to an electric converter 1632. The electric converter 1632 may convert the characteristics of the power from one of the power sources into a useable form that may be used either by the power storage 612 or one or more loads 1508 within the vehicle 100. The electrical converter 1624 may include any electronics or electrical devices and/or component that can change electrical characteristics, e.g., AC frequency, amplitude, phase, etc. associated with the electrical energy provided by the power source 1308. The converted electrical energy may then be provided to an optional conditioner 1638. The conditioner 1638 may include any electronics or electrical devices and/or component that may further condition the converted electrical energy by removing harmonics, noise, etc. from the electrical energy to provide a more stable and effective form of power to the vehicle 100.

Figure 17:
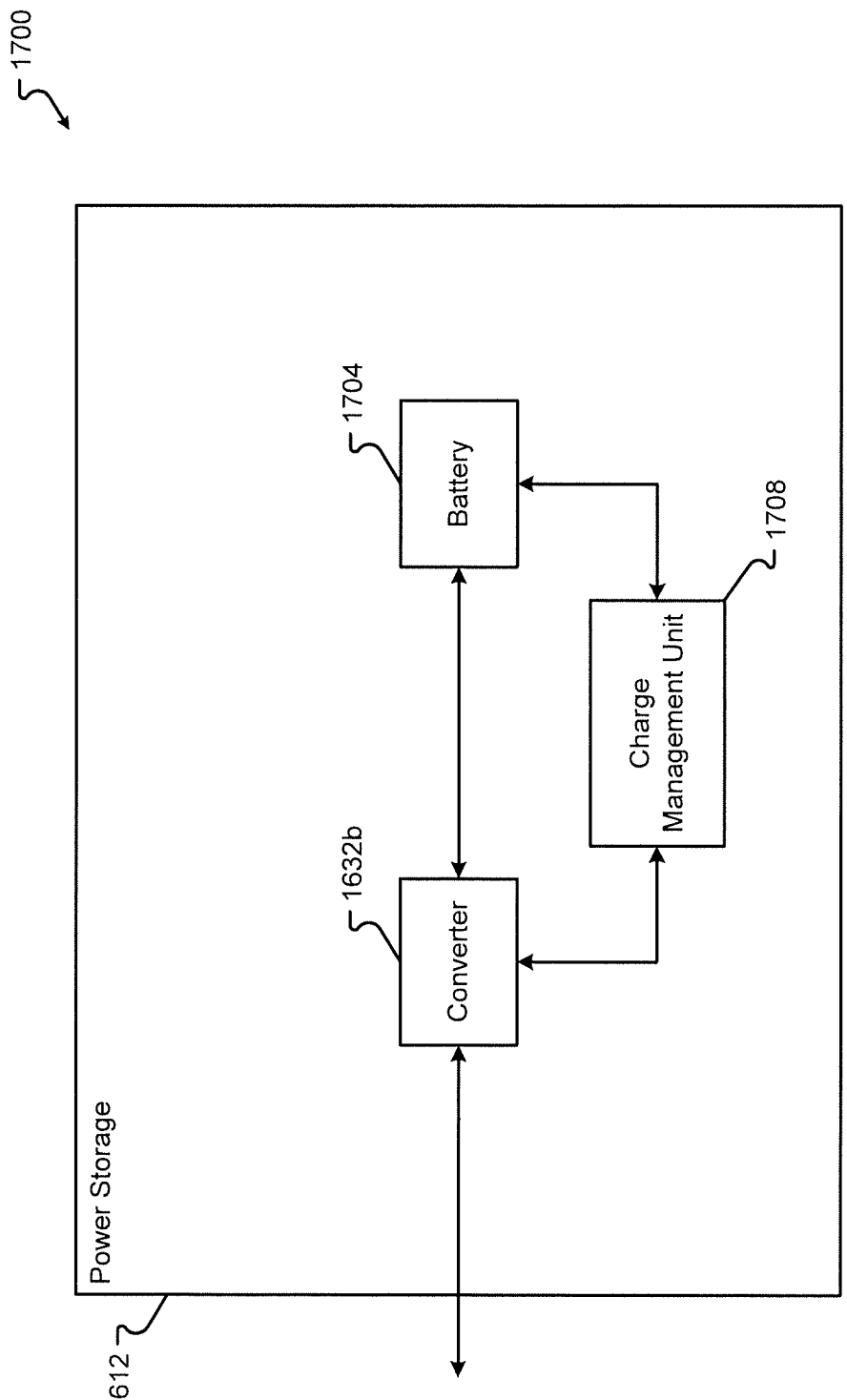
FIG. 17 is a block diagram of an embodiment of power storage associated with the electrical system of the vehicle.

An embodiment of the power storage 1612 may be as shown in FIG. 17. The power storage unit can include an electrical converter 1632*b*, one or more batteries, one or more rechargeable batteries, one or more capacitors, one or more accumulators, one or more supercapacitors, one or more ultrabatteries, and/or superconducting magnetics 1704, and/or a charge management unit 1708. The converter 1632*b* may be the same or similar to the electrical converter 1632*a* shown in FIG. 16. The converter 1632*b* may be a replacement for the electric converter 1632*a* shown in FIG. 16 and thus eliminate the need for the electrical converter 1632*a* as shown in FIG. 16. However, if the electrical converter 1632*a* is provided in the power generation unit 1504, the converter 1632*b*, as shown in the power storage unit 612, may be eliminated. The converter 1632*b* can also be redundant or different from the electrical converter 1632*a* shown in FIG. 16 and may provide a different form of energy to the battery and/or capacitors 1704. Thus, the converter 1632*b* can change the energy characteristics specifically for the battery/capacitor 1704.

The battery 1704 can be any type of battery for storing electrical energy, for example, a lithium ion battery, a lead acid battery, a nickel cadmium battery, etc. Further, the battery 1704 may include different types of power storage systems, such as, ionic fluids or other types of fuel cell systems. The energy storage 1704 may also include one or more high-capacity capacitors 1704. The capacitors 1704 may be used for long-term or short-term storage of electrical energy. The input into the battery or capacitor 1704 may be different from the output, and thus, the capacitor 1704 may be charged quickly but drain slowly. The functioning of the converter 1632 and battery capacitor 1704 may be monitored or managed by a charge management unit 1708.

The charge management unit 1708 can include any hardware (e.g., any electronics or electrical devices and/or components), software, or firmware operable to adjust the operations of the converter 1632 or batteries/capacitors 1704. The charge management unit 1708 can receive inputs or periodically monitor the converter 1632 and/or battery/capacitor 1704 from this information; the charge management unit 1708 may then adjust settings or inputs into the converter 1632 or battery/capacitor 1704 to control the operation of the power storage system 612.

Figure 18:
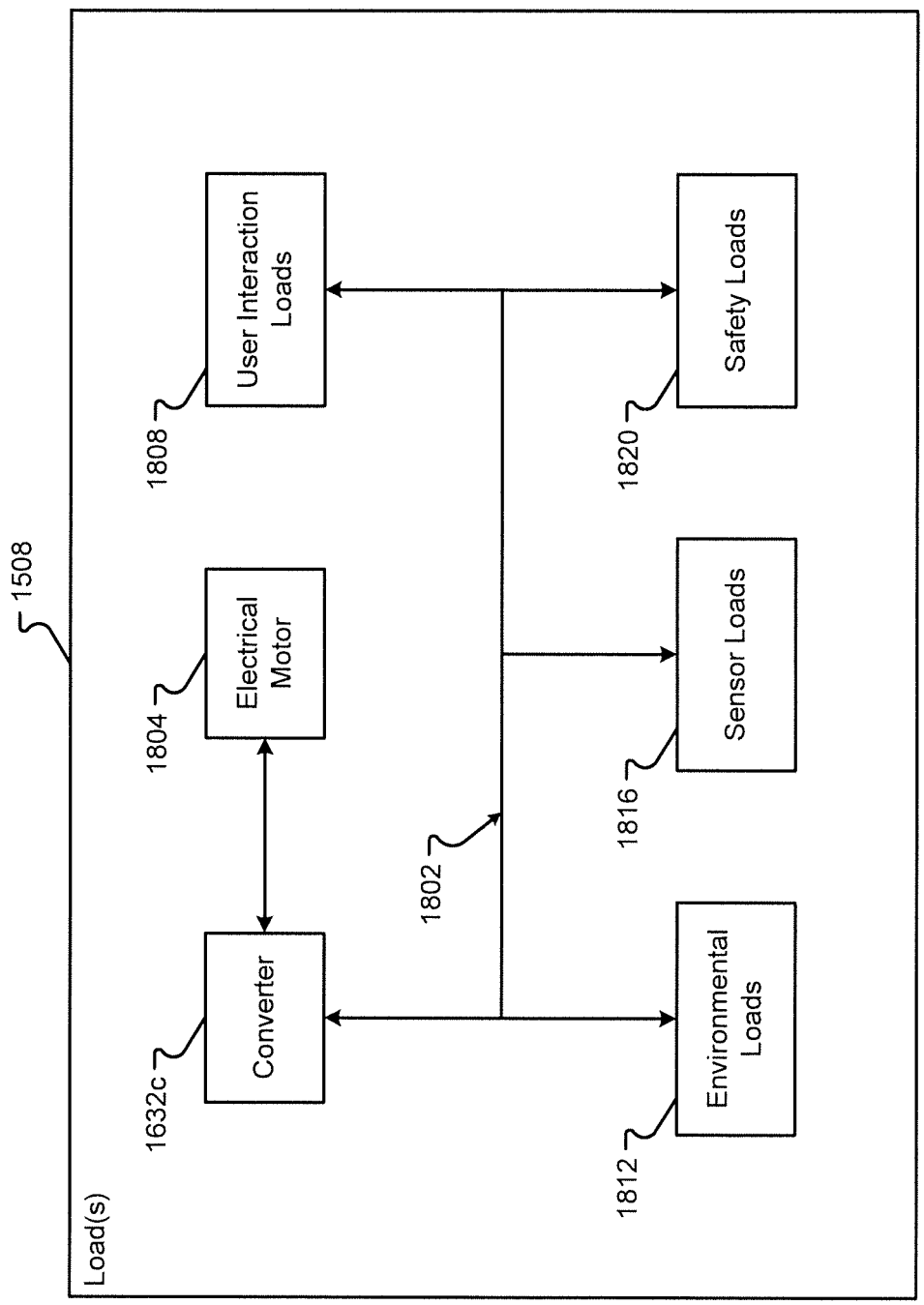
FIG. 18 is a block diagram of an embodiment of loads associated with the electrical system of the vehicle.

An embodiment of one or more loads 1508 associated with the vehicle 100 may be as shown in FIG. 18. The loads 1508 may include a bus or electrical interconnection system 1802, which provides electrical energy to one or more different loads within the vehicle 100. The bus 1802 can be any number of wires or interfaces used to connect the power generation unit 1504 and/or power storage 1612 to the one or more loads 1508. The converter 1632*c* may be an interface from the power generation unit 1504 or the power storage 612 into the loads 1508. The converter 1632*c* may be the same or similar to electric converter 1632*a* as shown in FIG. 16. Similar to the discussion of the converter 1632*b* in FIG. 17, the converter 1632*c* may be eliminated, if the electric converter 1632*a*, shown in FIG. 16, is present. However, the converter 1632*c* may further condition or change the energy characteristics for the bus 1802 for use by the loads 1508. The converter 1632*c* may also provide electrical energy to electric motor 1804, which may power the vehicle 100.

The electric motor 1804 can be any type of DC or AC electric motor. The electric motor may be a direct drive or induction motor using permanent magnets and/or winding either on the stator or rotor. The electric motor 1804 may also be wireless or include brush contacts. The electric motor 1804 may be capable of providing a torque and enough kinetic energy to move the vehicle 100 in traffic.

The different loads 1508 may also include environmental loads 1812, sensor loads 1816, safety loads 1820, user interaction loads 1808, etc. User interaction loads 1808 can be any energy used by user interfaces or systems that interact with the driver and/or passenger(s). These loads 1808 may include, for example, the heads up display, the dash display, the radio, user interfaces on the head unit, lights, radio, and/or other types of loads that provide or receive information from the occupants of the vehicle 100. The environmental loads 1812 can be any loads used to control the environment within the vehicle 100. For example, the air conditioning or heating unit of the vehicle 100 can be environmental loads 1812. Other environmental loads can include lights, fans, and/or defrosting units, etc. that may control the environment within the vehicle 100. The sensor loads 1816 can be any loads used by sensors, for example, air bag sensors, GPS, and other such sensors used to either manage or control the vehicle 100 and/or provide information or feedback to the vehicle occupants. The safety loads 1820 can include any safety equipment, for example, seat belt alarms, airbags, headlights, blinkers, etc. that may be used to manage the safety of the occupants. There may be more or fewer loads than those described herein, although they may not be shown in FIG. 18.

Figure 19A:
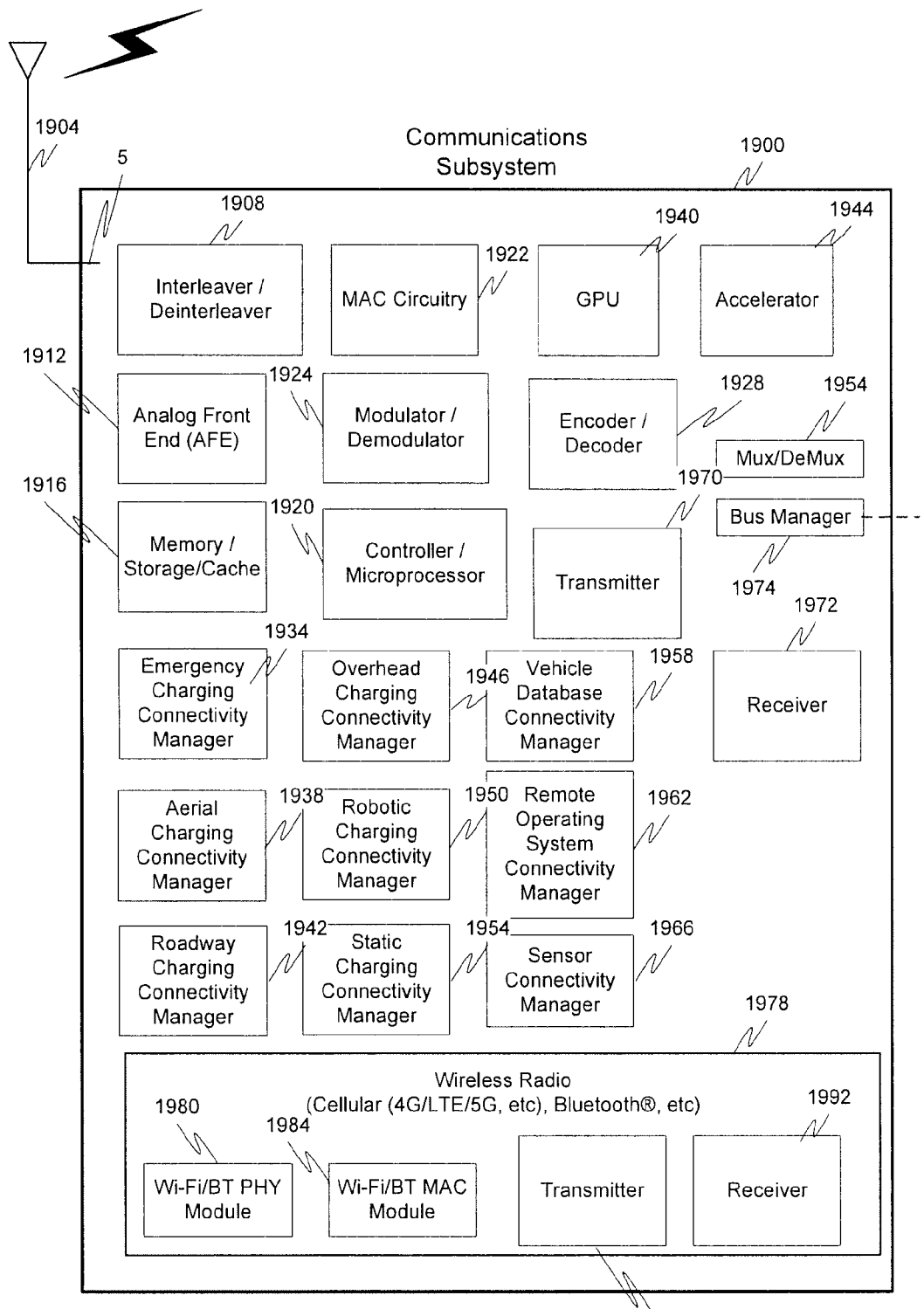
FIG. 19A is a block diagram of an exemplary embodiment of a communications subsystem of the vehicle.

FIG. 19 illustrates an exemplary hardware diagram of communications componentry that can be optionally associated with the vehicle.

The communications componentry can include one or more wired or wireless devices such as a transceiver(s) and/or modem that allows communications not only between the various systems disclosed herein but also with other devices, such as devices on a network, and/or on a distributed network such as the Internet and/or in the cloud.

The communications subsystem can also include inter- and intra-vehicle communications capabilities such as hotspot and/or access point connectivity for any one or more of the vehicle occupants and/or vehicle-to-vehicle communications.

Additionally, and while not specifically illustrated, the communications subsystem can include one or more communications links (that can be wired or wireless) and/or communications busses (managed by the bus manager 1974), including one or more of CANbus, OBD-II, ARCINC 429, Byteflight, CAN (Controller Area Network), D2B (Domestic Digital Bus), FlexRay, DC-BUS, IDB-1394, IEBus, I²C, ISO 9141-1/-2, J1708, J1587, J1850, J1939, ISO 11783, Keyword Protocol 2000, LIN (Local Interconnect Network), MOST (Media Oriended Systems Transport), Multifunction Vehicle Bus, SMARTwireX, SPI, VAN (Vehicle Area Network), and the like or in general any communications protocol and/or standard.

The various protocols and communications can be communicated one or more of wirelessly and/or over transmission media such as single wire, twisted pair, fibre optic, IEEE 1394, MIL-STD-1553, MIL-STD-1773, power-line communication, or the like. (All of the above standards and protocols are incorporated herein by reference in their entirety)

As discussed, the communications subsystem enables communications between any if the inter-vehicle systems and subsystems as well as communications with non-collocated resources, such as those reachable over a network such as the Internet.

The communications subsystem, in addition to well-known componentry (which has been omitted for clarity), the device communications subsystem 1900 includes interconnected elements including one or more of: one or more antennas 1904, an interleaver/deinterleaver 1908, an analog front end (AFE) 1912, memory/storage/cache 1916, controller/microprocessor 1920, MAC circuitry 1922, modulator/demodulator 1924, encoder/decoder 1928, a plurality of connectivity managers 1934-1966, GPU 1940, accelerator 1944, a multiplexer/demultiplexer 1954, transmitter 1970, receiver 1972 and wireless radio 1978 components such as a Wi-Fi PHY/Bluetooth® module 1980, a Wi-Fi/BT MAC module 1984, transmitter 1988 and receiver 1992. The various elements in the device 1900 are connected by one or more links/busses 5 (not shown, again for sake of clarity).

The device 400 can have one more antennas 1904, for use in wireless communications such as multi-input multi-output (MIMO) communications, multi-user multi-input multi-output (MU-MIMO) communications Bluetooth®, LTE, 4G, 5G, Near-Field Communication (NFC), etc. The antenna(s) 1904 can include, but are not limited to one or more of directional antennas, omnidirectional antennas, monopoles, patch antennas, loop antennas, microstrip antennas, dipoles, and any other antenna(s) suitable for communication transmission/reception. In an exemplary embodiment, transmission/reception using MIMO may require particular antenna spacing. In another exemplary embodiment, MIMO transmission/reception can enable spatial diversity allowing for different channel characteristics at each of the antennas. In yet another embodiment, MIMO transmission/reception can be used to distribute resources to multiple users for example within the vehicle and/or in another vehicle.

Antenna(s) 1904 generally interact with the Analog Front End (AFE) 1912, which is needed to enable the correct processing of the received modulated signal and signal conditioning for a transmitted signal. The AFE 1912 can be functionally located between the antenna and a digital baseband system in order to convert the analog signal into a digital signal for processing and vice-versa.

The subsystem 1900 can also include a controller/microprocessor 1920 and a memory/storage/cache 1916. The subsystem 1900 can interact with the memory/storage/cache 1916 which may store information and operations necessary for configuring and transmitting or receiving the information described herein. The memory/storage/cache 1916 may also be used in connection with the execution of application programming or instructions by the controller/microprocessor 1920, and for temporary or long term storage of program instructions and/or data. As examples, the memory/storage/cache 1920 may comprise a computer-readable device, RAM, ROM, DRAM, SDRAM, and/or other storage device(s) and media.

The controller/microprocessor 1920 may comprise a general purpose programmable processor or controller for executing application programming or instructions related to the subsystem 1900. Furthermore, the controller/microprocessor 1920 can perform operations for configuring and transmitting/receiving information as described herein. The controller/microprocessor 1920 may include multiple processor cores, and/or implement multiple virtual processors. Optionally, the controller/microprocessor 1920 may include multiple physical processors. By way of example, the controller/microprocessor 1920 may comprise a specially configured Application Specific Integrated Circuit (ASIC) or other integrated circuit, a digital signal processor(s), a controller, a hardwired electronic or logic circuit, a programmable logic device or gate array, a special purpose computer, or the like.

The subsystem 1900 can further include a transmitter 1970 and receiver 1972 which can transmit and receive signals, respectively, to and from other devices, subsystems and/or other destinations using the one or more antennas 1904 and/or links/busses. Included in the subsystem 1900 circuitry is the medium access control or MAC Circuitry 1922. MAC circuitry 1922 provides for controlling access to the wireless medium. In an exemplary embodiment, the MAC circuitry 1922 may be arranged to contend for the wireless medium and configure frames or packets for communicating over the wireless medium.

The subsystem 1900 can also optionally contain a security module (not shown). This security module can contain information regarding but not limited to, security parameters required to connect the device to one or more other devices or other available network(s), and can include WEP or WPA/WPA-2 (optionally+AES and/or TKIP) security access keys, network keys, etc. The WEP security access key is a security password used by Wi-Fi networks. Knowledge of this code can enable a wireless device to exchange information with an access point and/or another device. The information exchange can occur through encoded messages with the WEP access code often being chosen by the network administrator. WPA is an added security standard that is also used in conjunction with network connectivity with stronger encryption than WEP.

The exemplary subsystem 1900 also includes a GPU 1940, an accelerator 1944, a Wi-Fi/BT/BLE PHY module 1980 and a Wi-Fi/BT/BLE MAC module 1984 and wireless transmitter 1988 and receiver 1992. In some embodiments, the GPU 1940 may be a graphics processing unit, or visual processing unit, comprising at least one circuit and/or chip that manipulates and changes memory to accelerate the creation of images in a frame buffer for output to at least one display device. The GPU 1940 may include one or more of a display device connection port, printed circuit board (PCB), a GPU chip, a metal-oxide-semiconductor field-effect transistor (MOSFET), memory (e.g., single data rate random-access memory (SDRAM), double data rate random-access memory (DDR) RAM, etc., and/or combinations thereof), a secondary processing chip (e.g., handling video out capabilities, processing, and/or other functions in addition to the GPU chip, etc.), a capacitor, heatsink, temperature control or cooling fan, motherboard connection, shielding, and the like.

The various connectivity managers 1934-1966 (even) manage and/or coordinate communications between the subsystem 1900 and one or more of the systems disclosed herein and one or more other devices/systems. The connectivity managers include an emergency charging connectivity manager 1934, an aerial charging connectivity manager 1938, a roadway charging connectivity manager 1942, an overhead charging connectivity manager 1946, a robotic charging connectivity manager 1950, a static charging connectivity manager 1954, a vehicle database connectivity manager 1958, a remote operating system connectivity manager 1962 and a sensor connectivity manager 1966.

The emergency charging connectivity manager 1934 can coordinate not only the physical connectivity between the vehicle and the emergency charging device/vehicle, but can also communicate with one or more of the power management controller, one or more third parties and optionally a billing system(s). As an example, the vehicle can establish communications with the emergency charging device/vehicle to one or more of coordinate interconnectivity between the two (e.g., by spatially aligning the charging receptacle on the vehicle with the charger on the emergency charging vehicle) and optionally share navigation information. Once charging is complete, the amount of charge provided can be tracked and optionally forwarded to, for example, a third party for billing. In addition to being able to manage connectivity for the exchange of power, the emergency charging connectivity manager 1934 can also communicate information, such as billing information to the emergency charging vehicle and/or a third party. This billing information could be, for example, the owner of the vehicle, the driver of the vehicle, the driver of the vehicle, company information, or in general any information usable to charge the appropriate entity for the power received.

The aerial charging connectivity manager 1938 can coordinate not only the physical connectivity between the vehicle and the aerial charging device/vehicle, but can also communicate with one or more of the power management controller, one or more third parties and optionally a billing system(s). As an example, the vehicle can establish communications with the aerial charging device/vehicle to one or more of coordinate interconnectivity between the two (e.g., by spatially aligning the charging receptacle on the vehicle with the charger on the emergency charging vehicle) and optionally share navigation information. Once charging is complete, the amount of charge provided can be tracked and optionally forwarded to, for example, a third party for billing. In addition to being able to manage connectivity for the exchange of power, the aerial charging connectivity manager 1938 can similarly communicate information, such as billing information to the aerial charging vehicle and/or a third party. This billing information could be, for example, the owner of the vehicle, the driver of the vehicle, company information, or in general any information usable to charge the appropriate entity for the power received etc., as discussed.

The roadway charging connectivity manager 1942 and overhead charging connectivity manager 1946 can coordinate not only the physical connectivity between the vehicle and the charging device/system, but can also communicate with one or more of the power management controller, one or more third parties and optionally a billing system(s). As one example, the vehicle can request a charge from the charging system when, for example, the vehicle needs or is predicted to need power. As an example, the vehicle can establish communications with the charging device/vehicle to one or more of coordinate interconnectivity between the two for charging and share information for billing. Once charging is complete, the amount of charge provided can be tracked and optionally forwarded to, for example, a third party for billing. This billing information could be, for example, the owner of the vehicle, the driver of the vehicle, company information, or in general any information usable to charge the appropriate entity for the power received etc., as discussed. The person responsible for paying for the charge could also receive a copy of the billing information as is customary. The robotic charging connectivity manager 1950 and static charging connectivity manager 1954 can operate in a similar manner to that described herein.

The vehicle database connectivity manager 1958 allows the subsystem to receive and/or share information stored in the vehicle database. This information can be shared with other vehicle components/subsystems and/or other entities, such as third parties and/or charging systems. The information can also be shared with one or more vehicle occupant devices, such as an app on a mobile device the driver uses to track information about the vehicle and/or a dealer or service/maintenance provider. In general, any information stored in the vehicle database can optionally be shared with any one or more other devices optionally subject to any privacy or confidentially restrictions.

The remote operating system connectivity manager 1962 facilitates communications between the vehicle and any one or more autonomous vehicle systems. These communications can include one or more of navigation information, vehicle information, occupant information, or in general any information related to the remote operation of the vehicle.

The sensor connectivity manager 1966 facilitates communications between any one or more of the vehicle sensors and any one or more of the other vehicle systems. The sensor connectivity manager 1966 can also facilitate communications between any one or more of the sensors and/or vehicle systems and any other destination, such as a service company, app, or in general to any destination where sensor data is needed.

In accordance with one exemplary embodiment, any of the communications discussed herein can be communicated via the conductor(s) used for charging. One exemplary protocol usable for these communications is Power-line communication (PLC). PLC is a communication protocol that uses electrical wiring to simultaneously carry both data, and Alternating Current (AC) electric power transmission or electric power distribution. It is also known as power-line carrier, power-line digital subscriber line (PDSL), mains communication, power-line telecommunications, or power-line networking (PLN). For DC environments in vehicles PLC can be used in conjunction with CAN-bus, LIN-bus over power line (DC-LIN) and DC-BUS.

The communications subsystem can also optionally manage one or more identifiers, such as an IP (internet protocol) address(es), associated with the vehicle and one or other system or subsystems or components therein. These identifiers can be used in conjunction with any one or more of the connectivity managers as discussed herein.

Figure 19B:
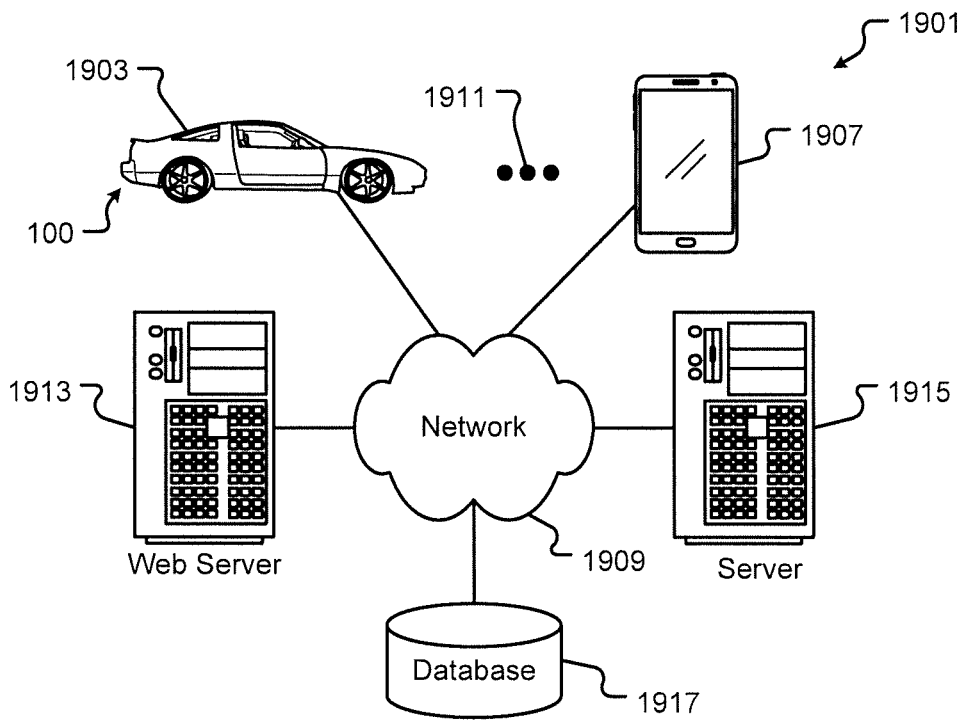
FIG. 19B is a block diagram of a computing environment associated with the embodiments presented herein.

FIG. 19B illustrates a block diagram of a computing environment 1901 that may function as the servers, user computers, or other systems provided and described above. The environment 1901 includes one or more user computers, or computing devices, such as a vehicle computing device 1903, a communication device 1907, and/or more 1911. The computing devices 1903, 1907, 1911 may include general purpose personal computers (including, merely by way of example, personal computers, and/or laptop computers running various versions of Microsoft Corp.'s Windows® and/or Apple Corp.'s Macintosh® operating systems) and/or workstation computers running any of a variety of commercially-available UNIX® or UNIX-like operating systems. These computing devices 1903, 1907, 1911 may also have any of a variety of applications, including for example, database client and/or server applications, and web browser applications. Alternatively, the computing devices 1903, 1907, 1911 may be any other electronic device, such as a thin-client computer, Internet-enabled mobile telephone, and/or personal digital assistant, capable of communicating via a network 1909 and/or displaying and navigating web pages or other types of electronic documents. Although the exemplary computer environment 1901 is shown with two computing devices, any number of user computers or computing devices may be supported.

Environment 1901 further includes a network 1909. The network 1909 may can be any type of network familiar to those skilled in the art that can support data communications using any of a variety of commercially-available protocols, including without limitation SIP, TCP/IP, SNA, IPX, Apple-Talk, and the like. Merely by way of example, the network 1909 maybe a local area network ("LAN"), such as an Ethernet network, a Token-Ring network and/or the like; a wide-area network; a virtual network, including without limitation a virtual private network ("VPN"); the Internet; an intranet; an extranet; a public switched telephone network ("PSTN"); an infra-red network; a wireless network (e.g., a network operating under any of the IEEE 802.9 suite of protocols, the Bluetooth® protocol known in the art, and/or any other wireless protocol); and/or any combination of these and/or other networks.

The system may also include one or more servers 1913, 1915. In this example, server 1913 is shown as a web server and server 1915 is shown as an application server. The web server 1913, which may be used to process requests for web pages or other electronic documents from computing devices 1903, 1907, 1911. The web server 1913 can be running an operating system including any of those discussed above, as well as any commercially-available server operating systems. The web server 1913 can also run a variety of server applications, including SIP servers, HTTP servers, FTP servers, CGI servers, database servers, Java servers, and the like. In some instances, the web server 1913 may publish operations available operations as one or more web services.

The environment 1901 may also include one or more file and or/application servers 1915, which can, in addition to an operating system, include one or more applications accessible by a client running on one or more of the computing devices 1903, 1907, 1911. The server(s) 1915 and/or 1913 may be one or more general purpose computers capable of executing programs or scripts in response to the computing devices 1903, 1907, 1911. As one example, the server 1915, 1913 may execute one or more web applications. The web application may be implemented as one or more scripts or programs written in any programming language, such as Java™, C, C#°, or C++, and/or any scripting language, such as Perl, Python, or TCL, as well as combinations of any programming/scripting languages. The application server(s) 1915 may also include database servers, including without limitation those commercially available from Oracle, Microsoft, Sybase™, IBM™ and the like, which can process requests from database clients running on a computing device 1903, 1907, 1911.

The web pages created by the server 1913 and/or 1915 may be forwarded to a computing device 1903, 1907, 1911 via a web (file) server 1913, 1915. Similarly, the web server 1913 may be able to receive web page requests, web services invocations, and/or input data from a computing device 1903, 1907, 1911 (e.g., a user computer, etc.) and can forward the web page requests and/or input data to the web (application) server 1915. In further embodiments, the server 1915 may function as a file server. Although for ease of description, FIG. 19B illustrates a separate web server 1913 and file/application server 1915, those skilled in the art will recognize that the functions described with respect to servers 1913, 1915 may be performed by a single server and/or a plurality of specialized servers, depending on implementation-specific needs and parameters. The computer systems 1903, 1907, 1911, web (file) server 1913 and/or web (application) server 1915 may function as the system, devices, or components described in FIGS. 1-19A.

The environment 1901 may also include a database 1917. The database 1917 may reside in a variety of locations. By way of example, database 1917 may reside on a storage medium local to (and/or resident in) one or more of the computers 1903, 1907, 1911, 1913, 1915. Alternatively, it may be remote from any or all of the computers 1903, 1907, 1911, 1913, 1915, and in communication (e.g., via the network 1909) with one or more of these. The database 1917 may reside in a storage-area network ("SAN") familiar to those skilled in the art. Similarly, any necessary files for performing the functions attributed to the computers 1903, 1907, 1911, 1913, 1915 may be stored locally on the respective computer and/or remotely, as appropriate. The database 1917 may be a relational database, such as Oracle 20i®, that is adapted to store, update, and retrieve data in response to SQL-formatted commands.

Figure 19C:
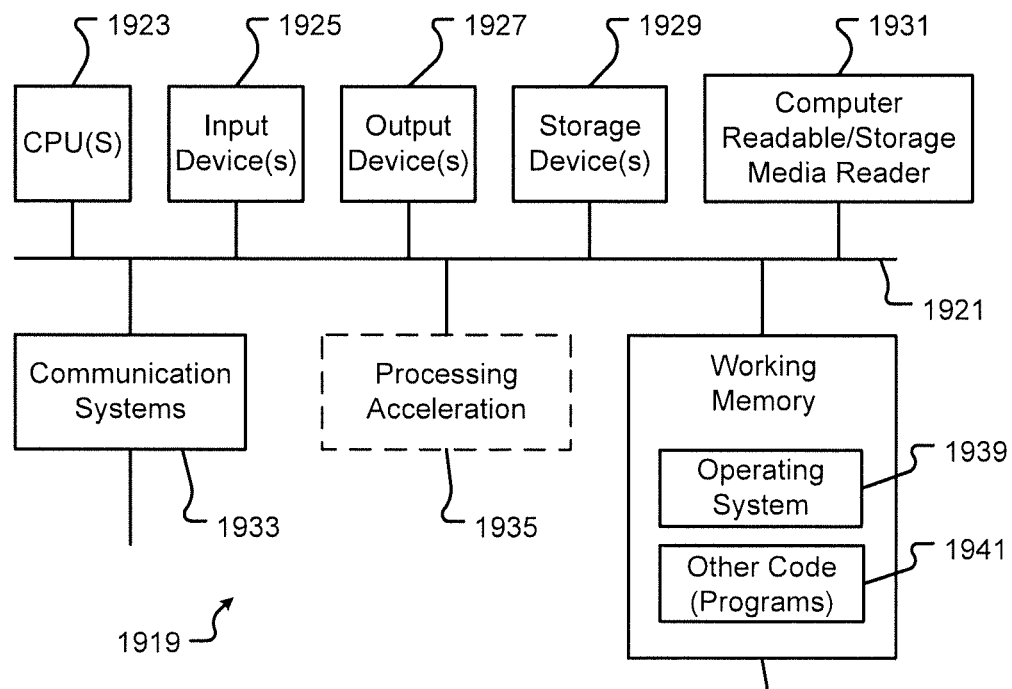
FIG. 19C is a block diagram of a computing device associated with one or more components described herein.

FIG. 19C illustrates one embodiment of a computer system 1919 upon which the servers, user computers, computing devices, or other systems or components described above may be deployed or executed. The computer system 1919 is shown comprising hardware elements that may be electrically coupled via a bus 1921. The hardware elements may include one or more central processing units (CPUs) 1923; one or more input devices 1925 (e.g., a mouse, a keyboard, etc.); and one or more output devices 1927 (e.g., a display device, a printer, etc.). The computer system 1919 may also include one or more storage devices 1929. By way of example, storage device(s) 1929 may be disk drives, optical storage devices, solid-state storage devices such as a random access memory ("RAM") and/or a read-only memory ("ROM"), which can be programmable, flash-updateable and/or the like.

The computer system 1919 may additionally include a computer-readable storage media reader 1931; a communications system 1933 (e.g., a modem, a network card (wireless or wired), an infra-red communication device, etc.); and working memory 1937, which may include RAM and ROM devices as described above. The computer system 1919 may also include a processing acceleration unit 1935, which can include a DSP, a special-purpose processor, and/or the like.

The computer-readable storage media reader 1931 can further be connected to a computer-readable storage medium, together (and, optionally, in combination with storage device(s) 1929) comprehensively representing remote, local, fixed, and/or removable storage devices plus storage media for temporarily and/or more permanently containing computer-readable information. The communications system 1933 may permit data to be exchanged with a network and/or any other computer described above with respect to the computer environments described herein. Moreover, as disclosed herein, the term "storage medium" may represent one or more devices for storing data, including read only memory (ROM), random access memory (RAM), magnetic RAM, core memory, magnetic disk storage mediums, optical storage mediums, flash memory devices and/or other machine readable mediums for storing information.

The computer system 1919 may also comprise software elements, shown as being currently located within a working memory 1937, including an operating system 1939 and/or other code 1941. It should be appreciated that alternate embodiments of a computer system 1919 may have numerous variations from that described above. For example, customized hardware might also be used and/or particular elements might be implemented in hardware, software (including portable software, such as applets), or both. Further, connection to other computing devices such as network input/output devices may be employed.

Examples of the processors 1923 as described herein may include, but are not limited to, at least one of Qualcomm® Snapdragon® 800 and 801, Qualcomm® Snapdragon® 620 and 615 with 4G LTE Integration and 64-bit computing, Apple® A7 processor with 64-bit architecture, Apple® M7 motion coprocessors, Samsung® Exynos® series, the Intel® Core™ family of processors, the Intel® Xeon® family of processors, the Intel® Atom™ family of processors, the Intel Itanium® family of processors, Intel® Core® i5-4670K and i7-4770K 22 nm Haswell, Intel® Core® i5-3570K 22 nm Ivy Bridge, the AMID® FX™ family of processors, AMD® FX-4300, FX-6300, and FX-8350 32 nm Vishera, AMD® Kaveri processors, Texas Instruments® Jacinto C6000™ automotive infotainment processors, Texas Instruments® OMAP™ automotive-grade mobile processors, ARM® Cortex™-M processors, ARM® Cortex-A and ARIV1926EJS™ processors, other industry-equivalent processors, and may perform computational functions using any known or future-developed standard, instruction set, libraries, and/or architecture.

Authentication can be an important capability of the computing environment 1901. For example, authentication of the operator and/or computing system 1903 can be used to control an operation or function of the computing system 1903 or vehicle 120 (such as locking or unlocking the vehicle, raising or lowering a window, selecting auto-adjustable seat, steering column/wheel, peddle, climate control, etc. settings, starting a power source or driving or otherwise operating the vehicle, enabling user or user portable device access to a local area network and/or on board computing components, completing a purchase of a product or service by the operator, a passenger or occupant, or the computing system 1903 itself, completing a license check to confirm proper usage of an on board component, such as a software and/or hardware and/or other component of the computing system or battery pack, and the like. Examples include authentication for such things as battery licensing, purchasing a charge (e.g., by amp-hour, distance traveled, overall wattage, amperes, etc.) or fuel, making a product purchase at a drive-thru, etc. As will be appreciated, in REVs amp-hour is directly proportional to the load, and wattage is a function of voltage and amperes.

Authentication can be a multi-factor authentication which enables or permits the operation or function to be performed or access to be granted only after an authentication mechanism successfully verifies or validates multiple items of information ("authentication information"). Any number of factors can be used for authentication. The use of multiple authentication factors in authentication assumes that an unauthorized actor is unlikely to supply the factors required for access. If, in an authentication attempt, at least one of the components is missing or supplied incorrectly, authentication is not successful and the requested function or access or other operation is denied.

Authentication can use a credential or key generated or derived by a cryptographic algorithm or engine from multiple factors. The key can be an authentication key, benign key, content-encryption key, crypto ignition key, cryptovariable, derived key, electronic key, ephemeral key, key encryption key, key production key, master key, master encryption key, public/private key, session key, symmetric key, asymmetric key, traffic encryption key, transmission security key, seed key, signature key, or stream key. Exemplary cryptographic algorithms used for key generation and/or authentication include a key derivation function, keystream generator, cryptographic hash function, key derivation function, cryptographic pseudorandom number generator, cryptanalytic algorithm, broken cryptography algorithm, asymmetric key algorithm, information-theoretically secure algorithm, integer factorization algorithm, symmetric key algorithm, Type 1, 2, or 2 3 encryption algorithm, advanced access content system, cipher block chain, and the like.

The factors can be static or dynamic. They can relate to an operator or passenger of the vehicle, his or her portable computing or communication device (e.g., smart phone, tablet computer, laptop, and the like), or the vehicle itself or a vehicle component (e.g., battery pack, chassis, motor or engine, etc.).

Operator or passenger factors include biometric data. Biometric data relates to a metric of a physiological or behavioral human characteristic. Physiological characteristics are related to the shape of the body. Examples include, but are not limited to, fingerprint, palm veins, face recognition (e.g., facial characteristic or digital face mapping parameter(s)), DNA, palm print, hand geometry (e.g., hand geometry characteristic or digital hand geometry mapping parameter(s)), iris recognition (e.g., iris characteristic or digital iris mapping parameter(s)), retina (e.g., retina characteristic or digital retina mapping parameter(s)), and odor and/or scent. Behavioral characteristics are related to the pattern of behavior of a person, including, but not limited to, typing rhythm, typing speed, pattern in key press intervals, gait, and voice (e.g., voice audible or spectral characteristic or digital voice print mapping parameter(s)).

Portable computing device or communication device 1907 factors include keyless remote identifier, communication device Electronic Serial Number ("ESN"), Mobile Equipment Identifier ("MEID"), International Mobile Equipment Identity ("MEI"), International Mobile Subscriber Identity ("IMSI") number (stored on a Subscriber Identity Module ("SIM") card), Temporary Mobile Subscriber Identity ("TMSI"), telephone number, and Mobile IP ("MIP") (optionally in conjunction with one or more public/private keys).

As will be appreciated, keyless remotes contain a short-range radio transmitter and must be within a certain range, usually about 5-20 meters, of the wireless radio signal receiver unit in the car to operate. When a button on the keyless remote is pushed, the keyless remote sends a coded signal by radio waves to the receiver unit in the car. Keyless remotes typically operate at a frequency of about 315 MHz for North America-made cars and at about 433.92 MHz for European, Japanese and Asian cars.

ESNs are often represented as either 11-digit decimal numbers or 8 digit hexadecimal numbers. For the decimal format the first three digits are the decimal representation of the first 8 bits (between 000 and 255 inclusive) and the next 8 digits are derived from the remaining 24 bits and will be between 00000000 and 16777215 inclusive. The decimal format of pseudo ESNs will therefore begin with 128. The decimal format separately displays 8 bit manufacturer codes in the first 3 digits, but 14 bit codes are not displayed as separate digits. The hexadecimal format displays an ESN as 8 digits and also does not separately display 14 bit manufacturer codes which occupy 3.5 hexadecimal digits.

A mobile equipment identifier (MEID) is a globally unique number identifying a physical piece of CDMA2000 mobile station equipment. The number format is defined by the 3GPP2 report SR0048 but in practical terms, it can be seen as an IMEI (discussed below) but with hexadecimal digits. An MEID is 56 bits long (14 hex digits). It comprises three fields, including an 8-bit regional code (RR), a 24-bit manufacturer code, and a 24-bit manufacturer-assigned serial number. The check digit (CD) is not considered part of the MEID.

The IMEI (15 decimal digits: 14 digits plus a check digit) or IMEISV (16 digits) includes information on the origin, model, and serial number of the device. The structure of the IMEI/SV is specified in 3GPP TS 23.003. The model and origin comprise the initial 8-digit portion of the IMEI/SV, known as the Type Allocation Code (TAC). The remainder of the IMEI is manufacturer-defined, with a Luhn check digit at the end.

The International Mobile Subscriber Identity or IMSI is used to identify the user of a cellular network and is a unique identification associated with all cellular networks. It is stored as a 64 bit field and is sent by the phone to the network. An IMSI is usually presented as a 15 digit number, but can be shorter. The first 3 digits are the mobile country code (MCC), which are followed by the mobile network code (MNC), either 2 digits (European standard) or 3 digits (North American standard). The length of the MNC depends on the value of the MCC. The remaining digits are the mobile subscription identification number (MSIN) within the network's customer base.

The Temporary Mobile Subscriber Identity (TMSI) is the identity that is most commonly sent between the mobile and the network. TMSI is randomly assigned by the Visitor Location Register ("VLR") to every mobile in the area, the moment it is switched on. The number is local to a location area, and so it has to be updated each time the mobile moves to a new geographical area. The Mobile IP allows for location-independent routing of IP datagrams on the Internet. Each mobile node is identified by its home address disregarding its current location in the Internet. While away from its home network, a mobile node is associated with a care-of address which identifies its current location and its home address is associated with the local endpoint of a tunnel to its home agent. Mobile IP specifies how a mobile node registers with its home agent and how the home agent routes datagrams to the mobile node through the tunnel.

The portable communication device 1907 or vehicle 120 can also use, as a factor, a valid passcode provided to the communication device 1907 or vehicle 120 for authentication purposes. If the user has already used a sequence of digits (passcode), this is automatically deleted and the authenticating server or server requesting authentication can send a new code to the communication device 1907. If the new code is not entered within a specified time limit, the authenticating server 2012 or server requesting authentication 2008 automatically sends a new passcode. This ensures that no old, already used codes are left on mobile devices or in vehicle memory. For added security, it is possible to specify how many incorrect entries are permitted before the authenticating server blocks access.

Factors about the vehicle itself include vehicle identification numbers ("VINs"), battery identifiers, and parameters sensed, captured or otherwise collected by one or more on board sensors.

A vehicle identification number (VIN), also called a chassis number, is a unique code, including a serial number, used by the automotive industry to identify individual motor vehicles. A VIN commonly includes a world manufacturer identifier to identify uniquely a manufacturer of the corresponding vehicle, a vehicle attribute or other descriptor of a characteristic of the corresponding vehicle, an indication that provides a clear identification of the corresponding vehicle, a check digit, a model year, a manufacturing plant code for the manufacturing plant making all or part of the vehicle, a sequential number, a vehicle descriptor section (to identify the vehicle type, and may include information on the automobile platform used, the model, and the body style), and a vehicle identifier section (to identify the individual vehicle in question and may include information on options installed, engine, or transmission, but often is a simple sequential number).

The parameters sensed, captured, or otherwise collected by an on board sensor and sensor connectivity manager 1966 can be static or dynamic. The parameter can be, for instance, an operating metric or other parameter associated with the vehicle, such as vehicle location (such as by determined by a Global Positioning System ("GPS") unit or other satellite positioning system), vehicle speed, acceleration, stored energy or fuel level, winding temperature, rotor speed, battery pack voltage level, output electrical current, electrical current direction of flow, leakage current, battery pack temperature, state-of-charge, state-of-health, or state-of-function, throttle position, manifold pressure, engine coolant temperature, mass air flow, camshaft position, crankshaft position, oxygen, detonation, EGR, intake air temperature, engine speed, brake or accelerator pedal position, brake pad wear, and fuel pressure. The controller/microprocessor 1920 or sensor connectivity manager 1966 of the vehicle 120 generally continuously or substantially continuously monitors sensor feedback signals to acquire the foregoing parameters. The parameter can be an associated with an interior or exterior of the vehicle, such as light level, still or video image of an object within or outside of the vehicle, sound signature of ambient noise within or outside of the vehicle, and received wireless signal.

Figure 20:
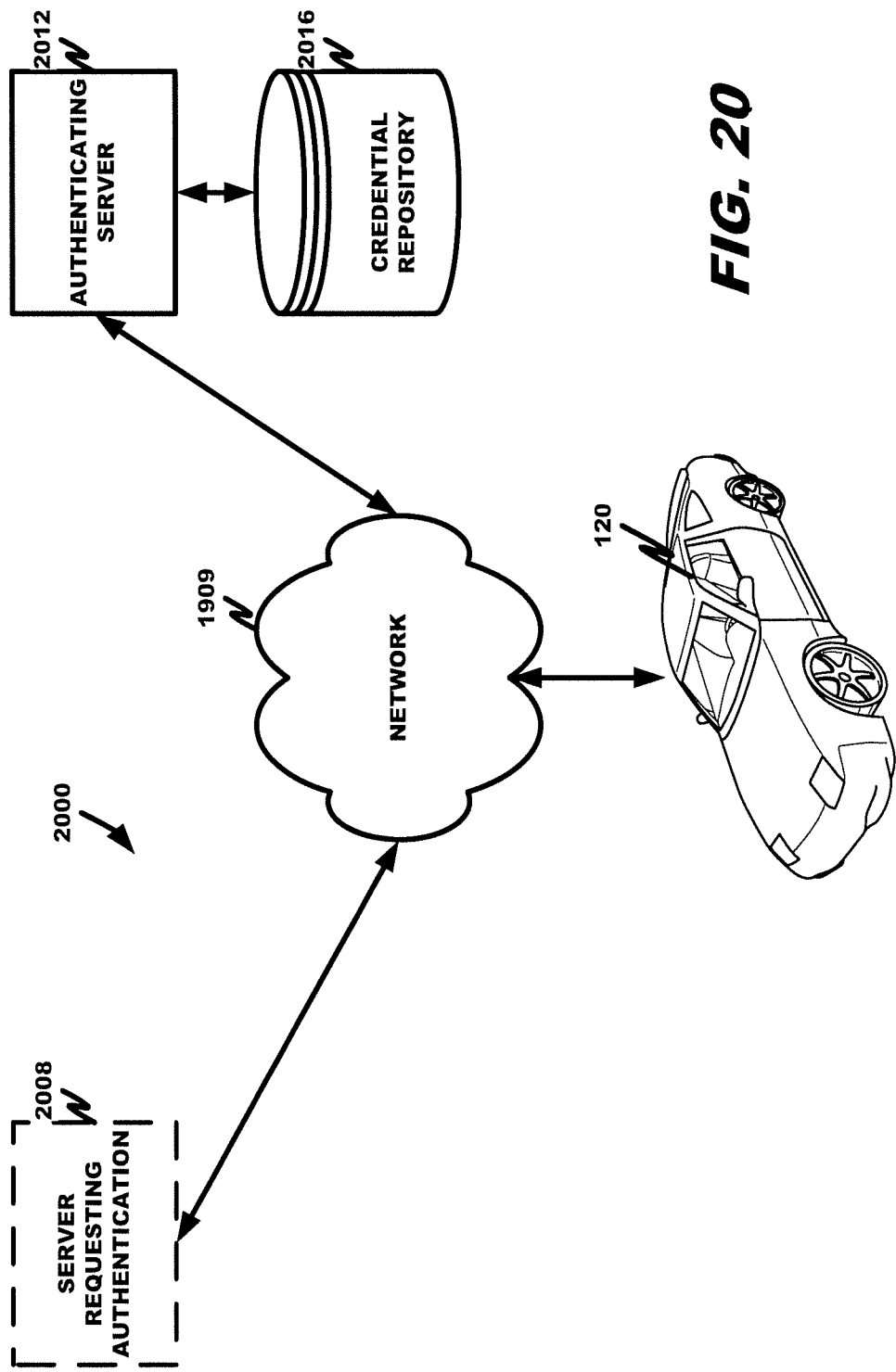
FIG. 20 is a block diagram of a distributed cryptographic system according to an embodiment.

Referring to FIG. 20, a cryptographic system 2000 is depicted according to an embodiment. The cryptographic system 2000 comprises a cryptographic manager (not shown) on board the vehicle 120 in communication, via network 1909, with a server 2008 requesting authentication of a vehicle occupant or the vehicle itself, and an authenticating server 2012 in communication with a credential repository 2016 to compare authentication information received from the cryptographic manager alone or from both the cryptographic manager and server 2008 requesting authentication with credentials stored locally in the credential repository 2016 to determine whether authentication is successful (the received authentication information matches one or more stored credentials) or unsuccessful (the received authentication information fails to match one or more stored credentials). The authentication information can be a factor or a key derived or generated from the factor.

Figure 21:
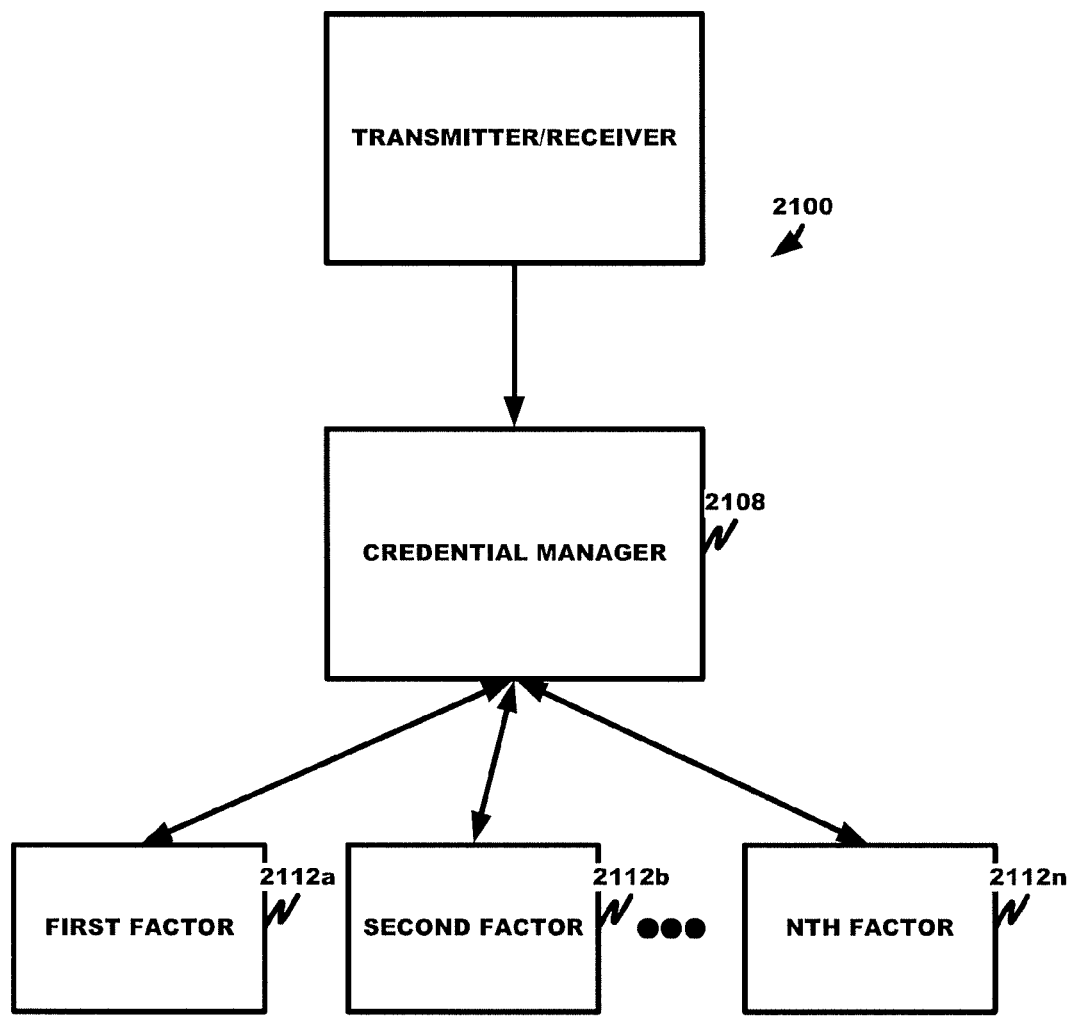
FIG. 21 is a block diagram of an on board cryptographic manager according to an embodiment.

Referring to FIG. 21, the cryptographic manager 2100 on board the vehicle 2004 comprises a transmitter 1970 or 1988 to send and a receiver 1972 or 1992 to receive wireless signals, a credential manager 2108 to receive, via receiver 1972 or 1992, requests for authentication via a user interface from a vehicle operator or passenger or via a remote communication device 1907 or server 1915, and stored first, second, . . . nth factors 2112*a-n*.

Figure 22:
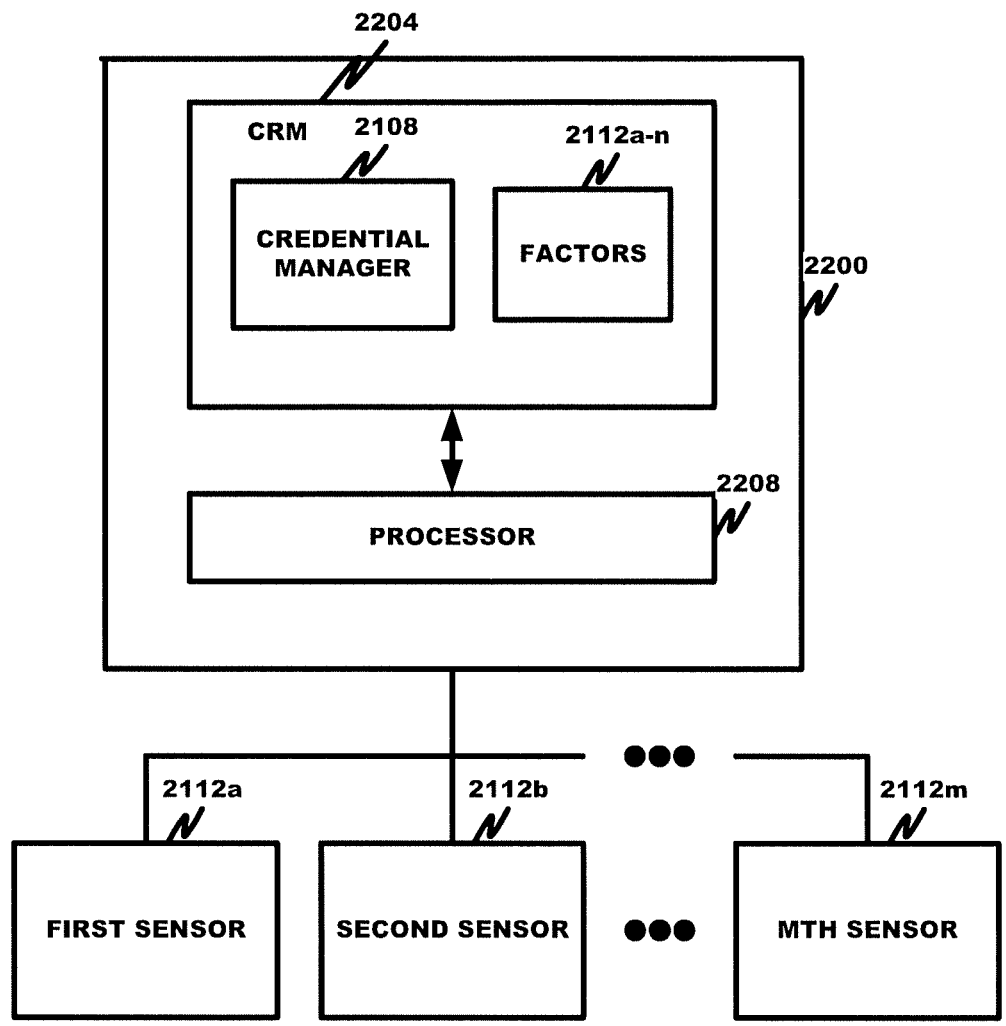
FIG. 22 is a block diagram of an on board cryptographic device executing the cryptographic manager according to an embodiment.

Referring to FIG. 22, the computational system 2200 on board the vehicle executing the credential manager 2108 comprises a computer readable medium 2204 in the memory 1916 comprising the credential manager 2108 and first, second, . . . nth factors 2112*a-n* and a processor 2208. The credential manager 2108 can receive the factors from first, second, . . . mth sensors 2212*a-m*. The first, second, . . . mth sensors 2112*a-m* can include a throttle or accelerator pedal position sensor, a brake pedal position sensor, manifold pressure sensor, engine coolant temperature sensor, mass air flow sensor, camshaft position sensor, crankshaft position sensor, pedal angle sensor, chassis position sensor, oxygen sensor, AC or DC current sensor, brake pad wear sensor, detonation sensor, EGR sensor and intake air temperature sensor. The cryptographic manager can optically read the VIN with a barcode scanner or digital camera or digitally read the VIN via OBD-II. An application on a portable computing device, such as a smartphone or tablet computer, can pass the VIN to the cryptographic manager. Biometric factors can be sensed an image processor, fingerprint, palm print, or palm vein scanner, retina or iris scanner, voice analyzer, keypad, and the like. Vehicle location can be determined by an SPS unit (such as a Global Positioning System or GPS unit). The identifiers associated with a portable computational device of an operator or passenger or on board communication device can be received by the cryptographic manager directly from the device. Ambient factors, such as light level can be captured by light sensor (e.g., photoresistor, photodiode, or phototransistor), still or video image by an image capture device, and sound signature can be captured by a microphone. Wireless signals can be captured by the receiver.

A number of examples will illustrate the concepts of this disclosure.

In a first example, the authenticating server 2012 is a licensing server performing a license check on a component of the vehicle 2004, such as a battery pack. The authenticating server 2012 requests multiple factors from the vehicle comprising, for example, a VIN or battery pack identifier and a biometric factor associated with the vehicle owner or a portable communication device of the vehicle owner (such as an electronic address). As will be appreciated, any other combination of factors can be used. The credential manager 2108 acquires the requested factors and forwards them to the authenticating server 2012. The authenticating server 2012 compares and successfully matches the received factors against stored credentials and successfully authenticates the operator of the vehicle as the owner of record and the licensed vehicle component as belonging to the owner of record.

In another example, the vehicle 120 is at a drive-through vendor to purchase an item. The server 2008 requesting authentication is associated with the drive-through vendor. The server 2008 provides, via a short range transmitter, a wireless signal comprising a request to provide factors to an authenticating server 2012 associated with a financial institution of the owner/operator of the vehicle. The request can comprise a description of the item(s) to be purchased (e.g., a QR code) and vendor identity. The vehicle provides factors to the vendor, via a short range transmitter, and the vendor scans the owner/operator's credit card. Both the server requesting authentication and the vehicle 2004 independently and separately forward the exchanged information to the authenticating server 2012, which compares a first of the factors, such as the vehicle's VIN, wireless remote signal description, owner/operator biometric factor, or electronic address of a portable communication device of the owner/operator, received from both the vehicle 2004 and server 2008 against a stored credential and compares the other second factor (such as a sensed vehicle parameter or sound signature of ambient noise) received from both the vehicle and server 2008 against one another. When the first factors each match the stored credential and the second factors match one another, the authenticating server successfully, authenticates the vehicle 120 as being associated with the owner/operator and can further compare credit card information received from the server 2008 and confirm that it is associated with the successfully authenticated vehicle as a second check on the identity of the person presenting the credit card.

In yet another example, the vehicle 120 is at a drive-through vendor to purchase an item. The server 2008 requesting authentication is associated with the drive-through vendor. The server 2008 provides, via a short range transmitter, a wireless signal comprising a request to provide factors to an authenticating server 2012 associated with a financial institution of the owner/operator. The request can comprise a description of the item(s) to be purchased (e.g., a QR code) and vendor identity. The vehicle provides factors to the vendor, via a short range transmitter. Both the server requesting authentication and the vehicle 2004 independently and separately forward the exchanged information to the authenticating server 2012, which compares a first of the factors, such as the electronic address of the owner/operator's communication device, wireless remote signal description, owner/operator biometric factor, or VIN received from both the vehicle 120 and server 2008 against a stored credential and compares the other second factor (such as a sensed vehicle parameter or sound signature of ambient noise) received from both the vehicle and server 2008 against one another. When the first factors each match the stored credential and the second factors match one another, the authenticating server successfully authenticates the owner/operator as being physically at the vendor and can further compare credit card information received from the server 2008 and confirm that it is associated with the successfully authenticated owner/operator as a second check on the identity of the person presenting the credit card.

In another example, an operator is seeking to perform a function or operation on the vehicle. Before the function or operation on the vehicle (e.g., start the ignition of the vehicle) can be performed, he or she must be authenticated successfully by the authenticating server as the owner of the vehicle or locally by the vehicle. The credential manager collects multiple factors, including the VIN of the vehicle, a biometric factor of the owner/operator or an electronic address of an on board or nearby communication device 1907 of the owner/operator and optionally forwards the authentication information to the server 2012. When the factors match values stored in the credential repository 2016 in association with the vehicle and its owner/operator or in the memory 1916 of the vehicle 120, the function or operation is enabled.

In another example, the vehicle 120 is monitored remotely (over the network 1909) by a remote monitoring service (which may be a fee-based service, warranty provider, vehicle manufacturer, etc.). The vehicle 120 periodically sends, via the vehicle database connectivity manager 1958, to the remote monitoring service wireless signals containing one or more vehicle parameter measurements received from one or more of the sensors 2112. The owner/operator or vehicle subsequently is involved in a transaction that requires authentication (e.g., battery pack license validation check, financial transaction, purchase of a good or service, and the like). The authenticating server 2012 receives, from the vehicle, multiple factors, such as an electronic address of the owner/operator's portable communication device (e.g., smart phone, tablet computer, and the like), wireless remote signal description, owner/operator biometric factor, or VIN along with a sensor measurement regarding a vehicle function or operation and timestamp of the sensor measurement. The authenticating server 2012 further receives, from the remote monitoring service, vehicle parameter measurements associated with the timestamp. The electronic address or VIN are compared with values stored in the credential repository 2016 and the sensor measurement values associated with the timestamp to authenticate the owner/operator or vehicle or both depending on the authentication information employed.

In yet another example, the vehicle 120 is at a drive-through vendor to purchase an item. The server 2008 requesting authentication is associated with the drive-through vendor. The server 2008 optionally provides, via a short range transmitter, a wireless signal comprising a request to provide factors to an authenticating server 2012 associated with a financial institution of the owner/operator. The request can comprise a description of the item(s) to be purchased (e.g., a QR code) and vendor identity. The server 208 receives from a local sensor a sensed ambient measurement, such as ambient light level or ambient noise sound signature. A different sensor on the vehicle captures the same measurement. Both the server requesting authentication and the vehicle 2004 independently and separately forward the sensed ambient measurement and authentication information regarding the owner/operator and/or vehicle (e.g., owner/operator biometric factor, VIN, electronic address of the owner/operator's portable communication device (e.g., smart phone, tablet computer, and the like), wireless remote signal description, and/or credit card information) to the authenticating server 2012, which compares a first of the factors, such as the authentication information received from both the vehicle 2004 and server 2008 against a stored credential and compares the other second factor, or the sensed ambient measurement, received from both the vehicle and server 2008 against one another. When the first factors each match the stored credential and the second factors match one another, the authenticating server successfully authenticates the owner/operator as being physically at the vendor and can further compare credit card information received from the server 2008 and confirm that it is associated with the successfully authenticated owner/operator as a second check on the identity of the person presenting the credit card.

An opportunity exists to use the unique information associated with a vehicle to assist with and be used as authentication information. Since VINs are unique, pairing this information with other types of IDs presents a robust manner of authenticating, for example, a driver and a vehicle, for a transaction. Specifically, the vehicle VIN, and/or a unique battery, module, or battery pack identifier, and/or an ignition key (or keyless remote) identifier and/or communication device ESN/SIM Card (optionally in conjunction with one or more public/private keys). The use of a vehicle as a source of authentication information can serve as "something that the user possesses". If a user wants to authenticate himself or herself, he or she can use a characteristic or descriptor associated with his or her vehicle or keyless remote (i.e. something that the individual user knows or possesses and may or may not be globally unique) plus a second unique factor (such as a valid, dynamic passcode or electronic address associated with a portable communication device of the user, VIN, battery pack ID, or user biometric factor). An advantage of this method is that there is no need for an additional, dedicated token, as users tend to carry routinely their mobile devices and are typically associated with a finite number of vehicles.

Multi-factor authentication can provide more reliable and robust authentication for an owner/operator or vehicle and reduce the time and effort required for authentication while at the same time not inconveniencing or distracting the owner/operator. VINs, vehicle sensor measurements, SPS units, microphones, and gyro/accelerometers can provide a trustworthy second factor in authentication.

Figure 23:
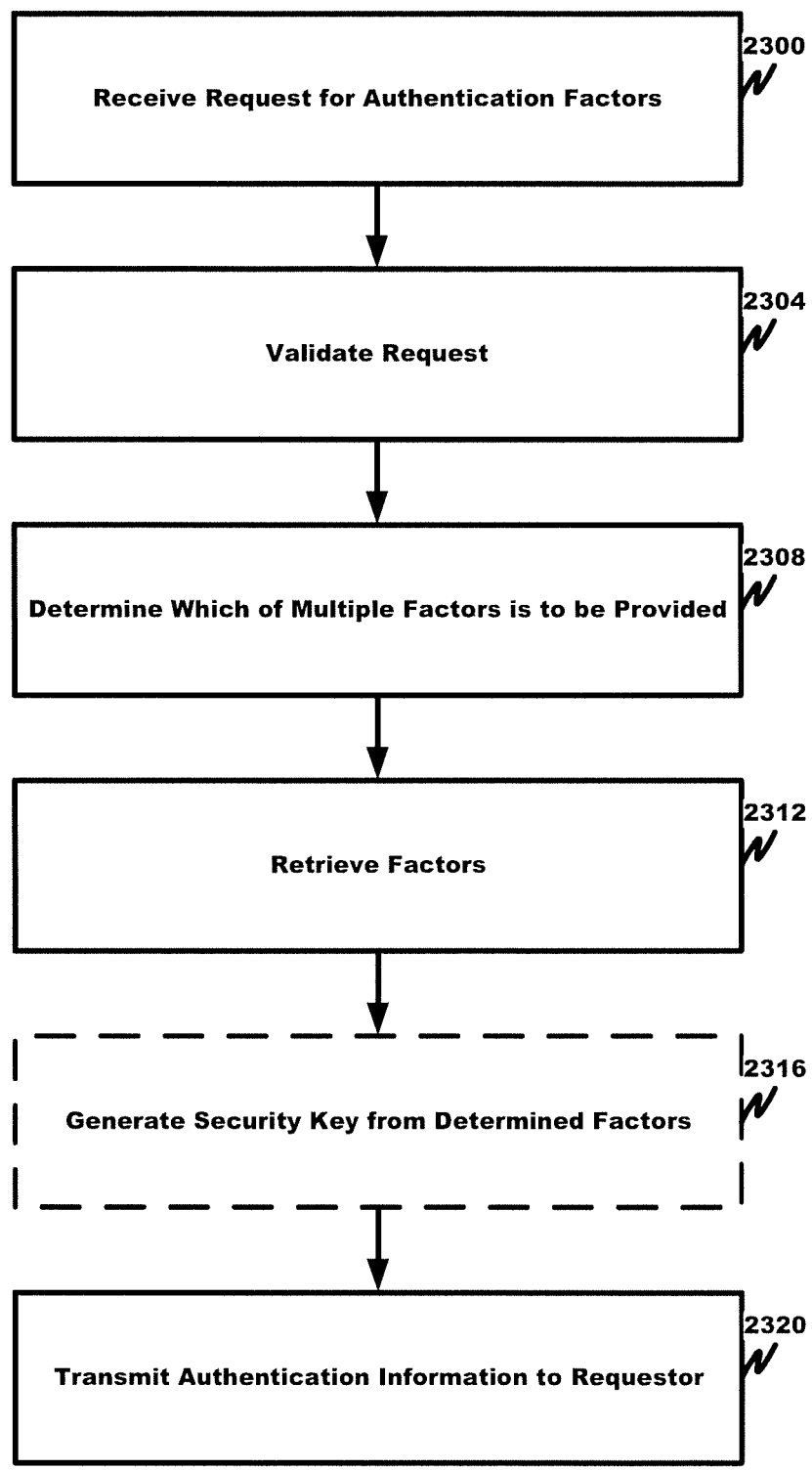
FIG. 23 is a flow chart according to an embodiment.
Figure 24:
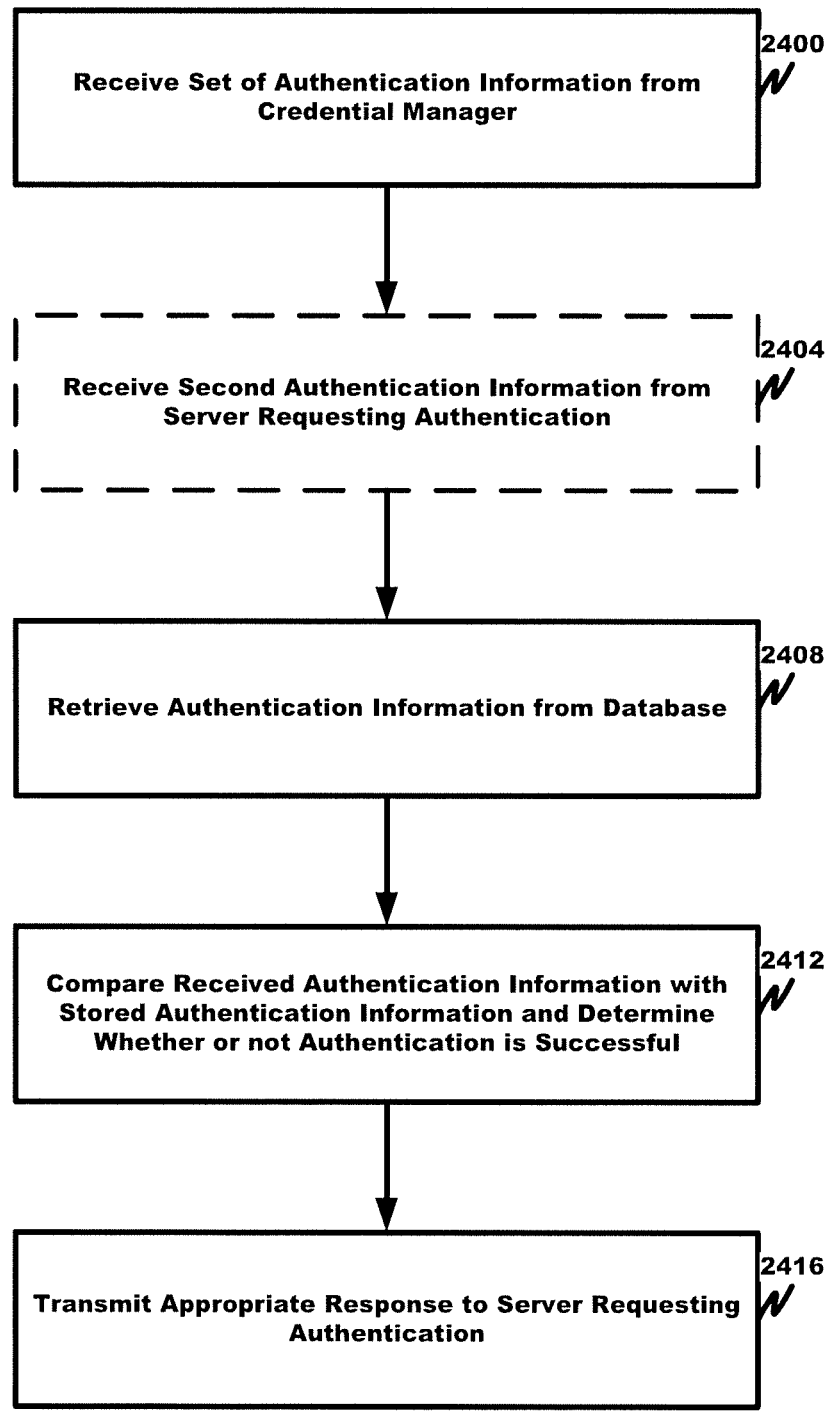
FIG. 24 is a flow chart according to an embodiment.

With reference to FIGS. 23 and 24, logical instructions according to an embodiment will be discussed.

In step 2300, the cryptographic manager 2100 receives a request, from the server requesting authentication or authenticating server depending on the application, for authentication credentials or factors.

In step 2304, the credential manager 2108 validates the request by known techniques.

In step 2308, the credential manager 2108 determines which of multiple first, second, . . . nth factors 2112*a-n* and, in step 2312, retrieves the determined factors.

In optional step 2316, the credential manager 2108 generates a security key from the determined factors.

In step 2320, the credential manager 2100 transmits authentication information to the requestor.

In step 2400, the authenticating server or server requesting authentication receives the transmitted authentication information from the cryptographic manager.

In step 2404, the authenticating server optionally receives second authentication information from the server requesting authentication.

In step 2408, the authenticating server retrieves authentication information for the vehicle and/or owner/operator from the credential database 2016.

In step 2412, the authenticating server compares the received authentication information with the retrieved authentication information and determines whether or not authentication is successful.

In step 2416, the authenticating server transmits the appropriate response (i.e., a comparison has failed to match and authentication failed or comparisons match and authentication is successful) to the server requesting authentication.

Figure 25:
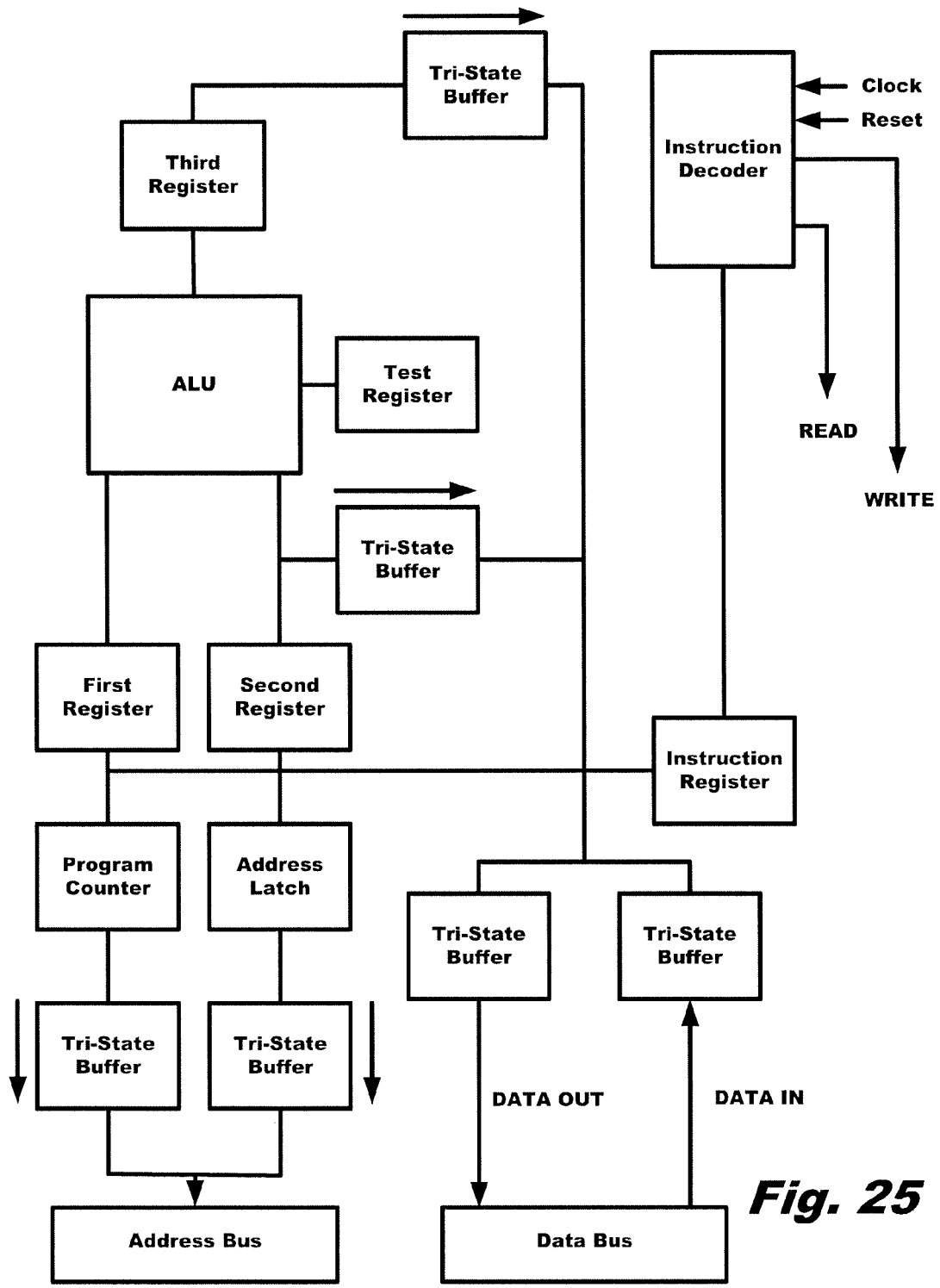
FIG. 25 is a block diagram of an exemplary computing system to execute the cryptographic manager.

With reference to FIG. 25, the logical instructions are executed by an arithmetic/logic unit ("ALU"), which performs mathematical operations, such as addition, subtraction, multiplication, and division, machine instructions, an address bus (that sends an address to memory), a data bus (that can send data to memory or receive data from memory), a read and write line to tell the memory whether to set or get the addressed location, a clock line that enables a clock pulse to sequence the processor, and a reset line that resets the program counter to zero or another value and restarts execution. The arithmetic/logic unit can be a floating point processor that performs operations on floating point numbers. The verification system further includes first, second, and third registers that are typically configured from flip-flops, an address latch, a program counter (which can increment by "1" and reset to "0"), a test register to hold values from comparisons performed in the arithmetic/logic unit, plural tri-state buffers to pass a "1" or "0" or disconnect its output (thereby allowing multiple outputs to connect to a wire but only one of them to actually drive a "1" or "0" into the line), and an instruction register and decoder to control other components. Control lines, in the verification system, from the instruction decoder can: command the first register to latch the value currently on the data bus, command the second register to latch the value currently on the data bus, command the third register to latch the value currently output by the ALU, command the program counter register to latch the value currently on the data bus, command the address register to latch the value currently on the data bus, command the instruction register to latch the value currently on the data bus, command the program counter to increment, command the program counter to reset to zero, activate any of the plural tri-state buffers (plural separate lines), command the ALU what operation to perform, command the test register to latch the ALU's test bits, activate the read line, and activate the write line. Bits from the test register and clock line as well as the bits from the instruction register come into the instruction decoder. Hardware similar or identical to that of FIG. 25 is in each of the server requesting authentication, cryptographic manager on board the vehicle, portable communication or computational device of the owner/operator, and authenticating server for executing the instructions of FIGS. 24-25. The ALU executes instructions for a random or pseudo-random number generation algorithm and generates the recipient identifier using the appropriate seed values.

Any of the steps, functions, and operations discussed herein can be performed continuously and automatically.

The exemplary systems and methods of this disclosure have been described in relation to vehicle systems and electric vehicles. However, to avoid unnecessarily obscuring the present disclosure, the preceding description omits a number of known structures and devices. This omission is not to be construed as a limitation of the scope of the claimed disclosure. Specific details are set forth to provide an understanding of the present disclosure. It should, however, be appreciated that the present disclosure may be practiced in a variety of ways beyond the specific detail set forth herein.

Furthermore, while the exemplary embodiments illustrated herein show the various components of the system collocated, certain components of the system can be located remotely, at distant portions of a distributed network, such as a LAN and/or the Internet, or within a dedicated system. Thus, it should be appreciated, that the components of the system can be combined into one or more devices, such as a server, communication device, or collocated on a particular node of a distributed network, such as an analog and/or digital telecommunications network, a packet-switched network, or a circuit-switched network. It will be appreciated from the preceding description, and for reasons of computational efficiency, that the components of the system can be arranged at any location within a distributed network of components without affecting the operation of the system.

Furthermore, it should be appreciated that the various links connecting the elements can be wired or wireless links, or any combination thereof, or any other known or later developed element(s) that is capable of supplying and/or communicating data to and from the connected elements. These wired or wireless links can also be secure links and may be capable of communicating encrypted information. Transmission media used as links, for example, can be any suitable carrier for electrical signals, including coaxial cables, copper wire, and fiber optics, and may take the form of acoustic or light waves, such as those generated during radio-wave and infra-red data communications.

While the flowcharts have been discussed and illustrated in relation to a particular sequence of events, it should be appreciated that changes, additions, and omissions to this sequence can occur without materially affecting the operation of the disclosed embodiments, configuration, and aspects.

A number of variations and modifications of the disclosure can be used. It would be possible to provide for some features of the disclosure without providing others.

In yet another embodiment, the systems and methods of this disclosure can be implemented in conjunction with a special purpose computer, a programmed microprocessor or microcontroller and peripheral integrated circuit element(s), an ASIC or other integrated circuit, a digital signal processor, a hard-wired electronic or logic circuit such as discrete element circuit, a programmable logic device or gate array such as PLD, PLA, FPGA, PAL, special purpose computer, any comparable means, or the like. In general, any device(s) or means capable of implementing the methodology illustrated herein can be used to implement the various aspects of this disclosure. Exemplary hardware that can be used for the present disclosure includes computers, handheld devices, telephones (e.g., cellular, Internet enabled, digital, analog, hybrids, and others), and other hardware known in the art. Some of these devices include processors (e.g., a single or multiple microprocessors), memory, nonvolatile storage, input devices, and output devices. Furthermore, alternative software implementations including, but not limited to, distributed processing or component/object distributed processing, parallel processing, or virtual machine processing can also be constructed to implement the methods described herein.

In yet another embodiment, the disclosed methods may be readily implemented in conjunction with software using object or object-oriented software development environments that provide portable source code that can be used on a variety of computer or workstation platforms. Alternatively, the disclosed system may be implemented partially or fully in hardware using standard logic circuits or VLSI design. Whether software or hardware is used to implement the systems in accordance with this disclosure is dependent on the speed and/or efficiency requirements of the system, the particular function, and the particular software or hardware systems or microprocessor or microcomputer systems being utilized.

In yet another embodiment, the disclosed methods may be partially implemented in software that can be stored on a storage medium, executed on programmed general-purpose computer with the cooperation of a controller and memory, a special purpose computer, a microprocessor, or the like. In these instances, the systems and methods of this disclosure can be implemented as a program embedded on a personal computer such as an applet, JAVA® or CGI script, as a resource residing on a server or computer workstation, as a routine embedded in a dedicated measurement system, system component, or the like. The system can also be implemented by physically incorporating the system and/or method into a software and/or hardware system.

Although the present disclosure describes components and functions implemented in the embodiments with reference to particular standards and protocols, the disclosure is not limited to such standards and protocols. Other similar standards and protocols not mentioned herein are in existence and are considered to be included in the present disclosure. Moreover, the standards and protocols mentioned herein and other similar standards and protocols not mentioned herein are periodically superseded by faster or more effective equivalents having essentially the same functions. Such replacement standards and protocols having the same functions are considered equivalents included in the present disclosure.

The present disclosure, in various embodiments, configurations, and aspects, includes components, methods, processes, systems and/or apparatus substantially as depicted and described herein, including various embodiments, subcombinations, and subsets thereof. Those of skill in the art will understand how to make and use the systems and methods disclosed herein after understanding the present disclosure. The present disclosure, in various embodiments, configurations, and aspects, includes providing devices and processes in the absence of items not depicted and/or described herein or in various embodiments, configurations, or aspects hereof, including in the absence of such items as may have been used in previous devices or processes, e.g., for improving performance, achieving ease, and/or reducing cost of implementation.

The foregoing discussion of the disclosure has been presented for purposes of illustration and description. The foregoing is not intended to limit the disclosure to the form or forms disclosed herein. In the foregoing Detailed Description for example, various features of the disclosure are grouped together in one or more embodiments, configurations, or aspects for the purpose of streamlining the disclosure. The features of the embodiments, configurations, or aspects of the disclosure may be combined in alternate embodiments, configurations, or aspects other than those discussed above. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment, configuration, or aspect. Thus, the following claims are hereby incorporated into this Detailed Description, with each claim standing on its own as a separate preferred embodiment of the disclosure.

Moreover, though the description of the disclosure has included description of one or more embodiments, configurations, or aspects and certain variations and modifications, other variations, combinations, and modifications are within the scope of the disclosure, e.g., as may be within the skill and knowledge of those in the art, after understanding the present disclosure. It is intended to obtain rights, which include alternative embodiments, configurations, or aspects to the extent permitted, including alternate, interchangeable and/or equivalent structures, functions, ranges, or steps to those claimed, whether or not such alternate, interchangeable and/or equivalent structures, functions, ranges, or steps are disclosed herein, and without intending to publicly dedicate any patentable subject matter.

Embodiments include a vehicle that can comprise:
a power source to propel the vehicle;
a user interface to receive commands from an occupant and provide output to the occupant;
a plurality of on board sensors to sense an operating parameter of the vehicle;
a computer readable medium for storing multiple factors; and
an on board microprocessor, coupled (or in communication) with the computer readable medium, that is programmed to:
receive and transmit the multiple factors to a remote server to authenticate the vehicle or a vehicle occupant, the multiple factors comprising a plurality of an electronic address of a portable communication device of the occupant, a wireless remote signal description, a biometric factor of the occupant, a vehicle-related identifier, a sensed vehicle parameter, a sensed environmental parameter, a passcode received from the remote server, or a derivative thereof.

Embodiments include a method that can comprise the step of:
collecting, by a vehicle microprocessor and on board sensor, multiple factors, the multiple factors comprising a plurality of an electronic address of a portable communication device of the occupant, a wireless remote signal description, a biometric factor of the occupant, a vehicle-related identifier, a sensed vehicle parameter, a sensed environmental parameter, a passcode received from the remote server, or a derivative thereof; and
transmitting multiple factors to a remote server to authenticate a vehicle or a vehicle occupant.

Embodiments include a vehicle that can comprise:
a power source to propel the vehicle;
a user interface to receive commands from an occupant and provide output to the occupant;
a plurality of on board sensors to sense an operating parameter of the vehicle;
a computer readable medium for storing multiple factors; and an on board microprocessor, coupled (or in communication) with the computer readable medium, that is programmed to:

receive a request, from the occupant via the user interface, to perform an operation or function;

determine multiple factors by the plurality of on board sensors;

compare the determined multiple factors against the stored multiple factors;

when the determined multiple factors each match a corresponding one of the stored multiple factors, the on board microprocessor performs the requested operation or function; and when one or more of the determined multiple factors does not match a corresponding one of the stored multiple factors, the on board microprocessor does not perform the requested operation or function, the determined and stored multiple factors each comprising a plurality of an electronic address of a portable communication device of the occupant, a wireless remote signal description, a biometric factor of the occupant, a sensed environmental parameter, and a passcode received from a remote server.

Aspects of one or more of the above embodiments can comprise a vehicle or method in which a derivative of one or more of the multiple factors is generated by the microprocessor. The key can be an authentication key, benign key, content-encryption key, crypto ignition key, cryptovariable, derived key, electronic key, ephemeral key, key encryption key, key production key, master key, master encryption key, public/private key, session key, symmetric key, asymmetric key, traffic encryption key, transmission security key, seed key, signature key, or stream key. The microprocessor can generate the key using a key derivation function, keystream generator, cryptographic hash function, key derivation function, cryptographic pseudorandom number generator, cryptanalytic algorithm, broken cryptography algorithm, asymmetric key algorithm, information-theoretically secure algorithm, integer factorization algorithm, symmetric key algorithm, Type 1, 2, or 2 3 encryption algorithm, advanced access content system, or cipher block chain.

Aspects of one or more of the above embodiments can comprise a vehicle or method in which the multiple factors comprise a biometric factor of the occupant. The biometric factor can relate to a metric of a physiological or behavioral human characteristic of the occupant, wherein the physiological characteristic is related to a shape of the body. The shape of the body can be a fingerprint, palm vein pattern, facial characteristic, palm print, hand geometry characteristic, iris characteristic, retina characteristic, or scent of the occupant. The behavioral characteristic can be related to a pattern of behavior of the occupant. The pattern of behavior can comprise typing rhythm, typing speed, pattern in key press intervals, gait, or voice characteristic. The plurality of sensors can comprise one or more of an image processor, fingerprint, palm print, or palm vein scanner, retina or iris scanner, voice analyzer, or keypad to collect the biometric factor.

Aspects of one or more of the above embodiments can comprise a vehicle or method in which the multiple factors comprise an electronic address of a portable communication device of the occupant, wherein the electronic address is one or more of communication device Electronic Serial Number ("ESN"), Mobile Equipment Identifier ("MEID"), International Mobile Equipment Identity ("IMEI"), International Mobile Subscriber Identity ("IMSI") number (stored on a Subscriber Identity Module ("SIM") card of the communication device), Temporary Mobile Subscriber Identity ("TMSI"), telephone number, and Mobile IP ("MIP").

Aspects of one or more of the above embodiments can comprise a vehicle or method in which the multiple factors comprise a wireless remote signal description emitted by a keyless remote. The keyless remote can comprise a short range radio transmitter emitting the wireless remote signal. The keyless remote can transmit the wireless remote signal as a coded signal by radio waves to a receiver in the vehicle.

Aspects of one or more of the above embodiments can comprise a vehicle or method in which the multiple factors comprise a passcode received by a receiver in the vehicle from the remote server. The passcode can delete automatically a passcode stored in the computer readable medium and previously used by the occupant. If the received passcode is not entered within a specified time limit, the remote server can automatically send a new passcode to the vehicle receiver.

Aspects of one or more of the above embodiments can comprise a vehicle or method in which the multiple factors comprise a vehicle-related identifier. The vehicle-related identifier can be a vehicle identification number ("VIN") of the vehicle or a unique identifier of a vehicle component. The microprocessor can one or more of optically read the vehicle-related identifier with a barcode scanner or digital camera or digitally read the vehicle-related identifier via OBD-II.

Aspects of one or more of the above embodiments can comprise a vehicle or method in which the multiple factors comprise a sensed vehicle parameter. The sensed vehicle parameter can be one or more of vehicle location, vehicle speed, acceleration, stored energy or fuel level, winding temperature, rotor speed, battery pack voltage level, output electrical current, electrical current direction of flow, leakage current, battery pack temperature, state-of-charge, state-of-health, or state-of-function, throttle position, manifold pressure, engine coolant temperature, mass air flow, camshaft position, crankshaft position, oxygen, detonation, EGR, intake air temperature, engine speed, brake pedal position, accelerator pedal position, brake pad wear, or fuel pressure. The plurality of sensors can comprise one or more of a throttle or accelerator pedal position sensor, a brake pedal position sensor, manifold pressure sensor, engine coolant temperature sensor, mass air flow sensor, camshaft position sensor, crankshaft position sensor, pedal angle sensor, chassis position sensor, oxygen sensor, AC or DC current sensor, brake pad wear sensor, detonation sensor, EGR sensor, satellite position system unit, or intake air temperature sensor to collect the sensed vehicle parameter.

Aspects of one or more of the above embodiments can comprise a vehicle or method in which a sensed environmental parameter is associated with an interior or exterior of the vehicle. The sensed environmental parameter can be one or more of light level, still or video image, and sound signature of ambient noise. The plurality of sensors can comprise one or more of a light sensor, still or video image by an image capture device, or a microphone to collect the sensed environmental parameter.

The phrases "at least one," "one or more," "or," and "and/or" are open-ended expressions that are both conjunctive and disjunctive in operation. For example, each of the expressions "at least one of A, B and C," "at least one of A, B, or C," "one or more of A, B, and C," "one or more of A, B, or C," "A, B, and/or C," and "A, B, or C" means A alone, B alone, C alone, A and B together, A and C together, B and C together, or A, B and C together.

The term "a" or "an" entity refers to one or more of that entity. As such, the terms "a" (or "an"), "one or more," and "at least one" can be used interchangeably herein. It is also to be noted that the terms "comprising," "including," and "having" can be used interchangeably.

The term "automatic" and variations thereof, as used herein, refers to any process or operation, which is typically continuous or semi-continuous, done without material human input when the process or operation is performed. However, a process or operation can be automatic, even though performance of the process or operation uses material or immaterial human input, if the input is received before performance of the process or operation. Human input is deemed to be material if such input influences how the process or operation will be performed. Human input that consents to the performance of the process or operation is not deemed to be "material."

Aspects of the present disclosure may take the form of an embodiment that is entirely hardware, an embodiment that is entirely software (including firmware, resident software, micro-code, etc.) or an embodiment combining software and hardware aspects that may all generally be referred to herein as a "circuit," "module," or "system." Any combination of one or more computer-readable medium(s) may be utilized. The computer-readable medium may be a computer-readable signal medium or a computer-readable storage medium.

A computer-readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer-readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer-readable storage medium may be any tangible medium that can contain or store a program for use by or in connection with an instruction execution system, apparatus, or device.

A computer-readable signal medium may include a propagated data signal with computer-readable program code embodied therein, for example, in baseband or as part of a carrier wave. Such a propagated signal may take any of a variety of forms, including, but not limited to, electro-magnetic, optical, or any suitable combination thereof. A computer-readable signal medium may be any computer-readable medium that is not a computer-readable storage medium and that can communicate, propagate, or transport a program for use by or in connection with an instruction execution system, apparatus, or device. Program code embodied on a computer-readable medium may be transmitted using any appropriate medium, including, but not limited to, wireless, wireline, optical fiber cable, RF, etc., or any suitable combination of the foregoing.

The term "database" or "data model" as used herein refers to any system, hardware, software, memory, storage device, firmware, component, etc., that stores data. The data model can be any type of database or storage framework described in conjunction with FIGS. 6 and 7, which is stored on any type of non-transitory, tangible computer readable medium. The data model can include one or more data structures, which may comprise one or more sections that store an item of data. A section may include, depending on the type of data structure, an attribute of an object, a data field, or other types of sections included in one or more types of data structures. The data model can represent any type of database, for example, relational databases, flat file databases, object-oriented databases, or other types of databases. Further, the data structures can be stored in memory or memory structures that may be used in either run-time applications or in initializing a communication.

The terms "determine," "calculate," "compute," and variations thereof, as used herein, are used interchangeably and include any type of methodology, process, mathematical operation or technique.

The term "electric vehicle" (EV), also referred to herein as an electric drive vehicle, may use one or more electric motors or traction motors for propulsion. An electric vehicle may be powered through a collector system by electricity from off-vehicle sources, or may be self-contained with a battery or generator to convert fuel to electricity. An electric vehicle generally includes a rechargeable electricity storage system (RESS) (also called Full Electric Vehicles (FEV)). Power storage methods may include: chemical energy stored on the vehicle in on-board batteries (e.g., battery electric vehicle or BEV), on board kinetic energy storage (e.g., flywheels), and/or static energy (e.g., by on-board double-layer capacitors). Batteries, electric double-layer capacitors, and flywheel energy storage may be forms of rechargeable on-board electrical storage.

The term "electronic address" refers to any contactable address, including a telephone number, instant message handle, e-mail address, Universal Resource Locator ("URL"), Universal Resource Identifier ("URI"), Address of Record ("AOR"), electronic alias in a database, like addresses, and combinations thereof.

The term "hybrid electric vehicle" refers to a vehicle that may combine a conventional (usually fossil fuel-powered) powertrain with some form of electric propulsion. Most hybrid electric vehicles combine a conventional internal combustion engine (ICE) propulsion system with an electric propulsion system (hybrid vehicle drivetrain). In parallel hybrids, the ICE and the electric motor are both connected to the mechanical transmission and can simultaneously transmit power to drive the wheels, usually through a conventional transmission. In series hybrids, only the electric motor drives the drivetrain, and a smaller ICE works as a generator to power the electric motor or to recharge the batteries. Power-split hybrids combine series and parallel characteristics. A full hybrid, sometimes also called a strong hybrid, is a vehicle that can run on just the engine, just the batteries, or a combination of both. A mid hybrid is a vehicle that cannot be driven solely on its electric motor, because the electric motor does not have enough power to propel the vehicle on its own.

The term "in communication with" as used herein refers to any coupling, connection, or interaction using electrical signals to exchange information or data, using any system, hardware, software, protocol, or format.

The term "network" as used herein refers to a system used by one or more user devices to communicate. The network can include one or more session managers, feature servers, communication endpoints, etc. that allow communications, whether voice or data, between two user devices. A network can be any network or communication system described herein. Generally, a network can be a local area network (LAN), a wide area network (WAN), a wireless LAN, a wireless WAN, the Internet, etc. that receives and transmits messages or data between devices. A network may communicate in any format or protocol known in the art, such as, transmission control protocol/internet protocol (TCP/IP), 802.11g, 802.11n, Bluetooth, or other formats or protocols.

The term "rechargeable electric vehicle" or "REV" refers to a vehicle with on board rechargeable energy storage, including electric vehicles and hybrid electric vehicles.

What is claimed is:

1. A vehicle, comprising:
a power source to propel the vehicle;
a user interface to receive commands from an occupant and provide output to the occupant;
a plurality of on board sensors to sense an operating parameter of the vehicle;
a computer readable medium for storing multiple authentication factors; and
an on board microprocessor, coupled with the computer readable medium, that is programmed to:
receive and transmit the multiple authentication factors or a key derived therefrom to a remote server to authenticate the vehicle or a vehicle occupant to the remote server, the multiple authentication factors comprising a plurality of an electronic address of a portable communication device of the occupant sensed by an on board sensor, a wireless remote signal description sensed by an on board sensor, a vehicle-related identifier, a vehicle parameter sensed by the on board processor, an environmental parameter sensed by the on board processor, and a passcode received by the microprocessor from the remote server.

2. The vehicle of claim 1, wherein the key is generated by the microprocessor using the multiple authentication factors as a seed value, wherein the key is an authentication key, benign key, content-encryption key, crypto ignition key, cryptovariable, derived key, electronic key, ephemeral key, key encryption key, key production key, master key, master encryption key, public/private key, session key, symmetric key, asymmetric key, traffic encryption key, transmission security key, seed key, signature key, or stream key, and wherein the microprocessor generates the key using a key derivation function, keystream generator, cryptographic hash function, key derivation function, cryptographic pseudorandom number generator, cryptanalytic algorithm, broken cryptography algorithm, asymmetric key algorithm, information-theoretically secure algorithm, integer factorization algorithm, symmetric key algorithm, Type 1, 2, or 2 3 encryption algorithm, advanced access content system, or cipher block chain.

3. The vehicle of claim 1, wherein the multiple authentication factors comprise a biometric factor of the occupant sensed by an on board sensor, wherein the biometric factor relates to a metric of a physiological or behavioral human characteristic of the occupant, wherein the physiological characteristic is related to a shape of the body, wherein the shape of the body is a fingerprint, palm vein pattern, facial characteristic, palm print, hand geometry characteristic, iris characteristic, retina characteristic, or scent of the occupant, wherein the behavioral characteristic is related to a pattern of behavior of the occupant, wherein the pattern of behavior comprises typing rhythm, typing speed, pattern in key press intervals, gait, or voice characteristic, and wherein the plurality of sensors comprise one or more of an image processor, fingerprint, palm print, or palm vein scanner, retina or iris scanner, voice analyzer, or keypad to collect the biometric factor.

4. The vehicle of claim 1, wherein the multiple authentication factors comprise an electronic address of a portable communication device of the occupant, wherein the electronic address is one or more of communication device Electronic Serial Number ("ESN"), Mobile Equipment Identifier ("MEID"), International Mobile Equipment Identity ("IMEI"), International Mobile Subscriber Identity ("IMSI") number (stored on a Subscriber Identity Module ("SIM") card of the communication device), Temporary Mobile Subscriber Identity ("TMSI"), telephone number, and Mobile IP ("MIP").

5. The vehicle of claim 1, wherein the multiple authentication factors comprise a wireless remote signal description emitted by a keyless remote, wherein the keyless remote comprises a short range radio transmitter emitting the wireless remote signal, and wherein the keyless remote transmits the wireless remote signal as a coded signal by radio waves to a receiver in the vehicle.

6. The vehicle of claim 1, wherein the multiple authentication factors comprise a passcode received by a receiver in the vehicle from the remote server, wherein the passcode deletes automatically a passcode stored in the computer readable medium and previously used by the occupant, and wherein, if the received passcode is not entered within a specified time limit, the remote server automatically sends a new passcode to the vehicle receiver.

7. The vehicle of claim 1, wherein the multiple authentication factors comprise a vehicle-related identifier, wherein the vehicle-related identifier is a vehicle identification number ("VIN") of the vehicle or a unique identifier of a vehicle component, and wherein the microprocessor one or more of optically reads the vehicle-related identifier with a barcode scanner or digital camera or digitally reads the vehicle-related identifier via OBD-II.

8. The vehicle of claim 1, wherein the multiple authentication factors comprise a sensed dynamically changing vehicle parameter, wherein the sensed vehicle parameter is one or more of vehicle location, vehicle speed, acceleration, stored energy or fuel level, winding temperature, rotor speed, battery pack voltage level, output electrical current, electrical current direction of flow, :leakage current, battery pack temperature, state-of-charge, state-of-health, or state-of-function, throttle position, manifold pressure, engine coolant temperature, mass air flow, camshaft position, crankshaft position, oxygen, detonation, EGR, intake air temperature, engine speed, brake pedal position, accelerator pedal position, brake pad wear, or fuel pressure, and wherein the plurality of sensors comprise one or more of a throttle or accelerator pedal position sensor, a brake pedal position sensor, manifold pressure sensor, engine coolant, temperature sensor, mass air flow sensor, camshaft position sensor, crankshaft position sensor, pedal angle sensor, chassis position sensor, oxygen sensor, AC or DC current sensor, brake pad wear sensor, detonation sensor, EGR sensor, satellite position system unit, or intake air temperature sensor to collect the sensed vehicle parameter.

9. The vehicle of claim 1, wherein the multiple authentication factors comprise a sensed dynamically changing environmental parameter, wherein the sensed environmental parameter is associated with an interior or exterior of the vehicle, wherein the sensed environmental parameter is one or more of light level, still or video image, and sound signature of ambient noise, and wherein the plurality of sensors comprise one or more of a light sensor, still or video image by an image capture device, or a microphone to collect the sensed environmental parameter.

10. A method, comprising:
collecting, by a vehicle microprocessor and on board sensor, multiple authentication factors, the multiple authentication factors comprising a plurality of an electronic address of a portable communication device of the occupant, a wireless remote signal description, a biometric factor of the occupant, a vehicle-related identifier, a sensed vehicle parameter, a sensed environmental parameter, and a passcode received from a remote server;

generating, by the microprocessor, the key from the multiple authentication factors using the multiple authentication factors as a seed value; and transmitting the key to the remote server to authenticate a vehicle or a vehicle occupant to the remote server.

11. The method of claim 10, further comprising:

generating, by the microprocessor, the key from the multiple authentication factors using the multiple authentication factors as a seed value, wherein the key is an authentication key, benign key, content-encryption key, crypto ignition key, cryptovariable, derived key, electronic key, ephemeral key, key encryption key, key production key, master key, master encryption key, public/private key, session key, symmetric key, asymmetric key, traffic encryption key, transmission security key, seed key, signature key, or stream key, and wherein the microprocessor generates the key using a key derivation function, keystream generator, cryptographic hash function, key derivation function, cryptographic pseudorandom number generator, cryptanalytic algorithm, broken cryptography algorithm, asymmetric key algorithm, information-theoretically secure algorithm, integer factorization algorithm, symmetric key algorithm, Type 1, 2, or 2 3 encryption algorithm, advanced access content system, or cipher block chain.

12. The method of claim 10, wherein the multiple authentication factors comprise a biometric factor of the occupant sensed by the on board sensor, wherein the biometric factor relates to a metric of a physiological or behavioral human characteristic of the occupant, wherein the physiological characteristic is related to a shape of the body, wherein the shape of the body is a fingerprint, palm vein pattern, facial characteristic, palm print, hand geometry characteristic, iris characteristic, retina characteristic, or scent of the occupant, wherein the behavioral characteristic is related to a pattern of behavior of the occupant, wherein the pattern of behavior comprises typing rhythm, typing speed, pattern in key press intervals, gait, or voice characteristic, and wherein the plurality of sensors comprise one or more of an image processor, fingerprint, palm print, or palm vein scanner, retina or iris scanner, voice analyzer, or keypad to collect the biometric factor.

13. The method of claim 10, wherein the multiple authentication factors comprise an electronic address of a portable communication device of the occupant, wherein the electronic address is one or more of communication device Electronic Serial Number ("ESN"), Mobile Equipment Identifier ("MEID"), International Mobile Equipment Identity ("IMEI"), International Mobile Subscriber Identity ("IMSI") number (stored on a Subscriber Identity Module ("SIM") card of the communication device), Temporary Mobile Subscriber Identity ("TMSI"), telephone number, and Mobile IP ("MIP").

14. The method of claim 10, wherein the multiple authentication factors comprise a wireless remote signal description emitted by a keyless remote, wherein the keyless remote comprises a short range radio transmitter emitting the wireless remote signal, and wherein the keyless remote transmits the wireless remote signal as a coded signal by radio waves to a receiver in the vehicle.

15. The method of claim 10, wherein the multiple authentication factors comprise a passcode received by a receiver in the vehicle from the remote server, wherein the passcode deletes automatically a passcode stored in the computer readable medium and previously used by the occupant, and wherein, if the received passcode is not entered within a specified time limit, the remote server automatically sends a new passcode to the vehicle receiver.

16. The method of claim 10, wherein the multiple authentication factors comprise a vehicle-related identifier, wherein the vehicle-related identifier is a vehicle identification number ("VIN") of the vehicle or a unique identifier of a vehicle component, and wherein the microprocessor one or more of optically reads the vehicle-related identifier with a barcode scanner or digital camera or digitally reads the vehicle-related identifier via OBD-II.

17. The method of claim 10, wherein the multiple authentication factors comprise a dynamically changing sensed vehicle parameter, wherein the sensed vehicle parameter is one or more of vehicle location, vehicle speed, acceleration, stored energy or fuel level, winding temperature, rotor speed, battery pack voltage level, output electrical current, electrical current direction of flow, leakage current, battery pack temperature, state-of-charge, state-of-health, or state-of-function, throttle position, manifold pressure, engine coolant temperature, mass air flow, camshaft position, crankshaft position, oxygen, detonation, EGR, intake air temperature, engine speed, brake pedal position, accelerator pedal position, brake pad wear, or fuel pressure, and wherein the plurality of sensors comprise one or more of a throttle or accelerator pedal position sensor, a brake pedal position sensor, manifold pressure sensor, engine coolant temperature sensor, mass air flow sensor, camshaft position sensor, crankshaft position sensor, pedal angle sensor, chassis position sensor, oxygen sensor, AC or DC current sensor, brake pad wear sensor, detonation sensor, EGF sensor, satellite position system unit, or intake air temperature sensor to collect the sensed vehicle parameter.

18. The method of claim 10, wherein the multiple authentication factors comprise a dynamically changing sensed environmental parameter, wherein the sensed environmental parameter is associated with an interior or exterior of the vehicle, wherein the sensed environmental parameter is one or more of light level, still or video image, and sound signature of ambient noise, and wherein the plurality of sensors comprise one or more of a light sensor, still or video image by an image capture device, or a microphone to collect the sensed environmental parameter.

19. A method, comprising:

receiving, by a remote server from a vehicle microprocessor, a plurality of authentication factors or a key derived therefrom, the plurality of authentication factors comprising a plurality of an electronic address of a portable communication device of the occupant, a wireless remote signal description, a biometric factor of the occupant, a vehicle-related identifier, a sensed vehicle parameter, a sensed environmental parameter, and a passcode received from the remote server;

comparing the plurality of authentication factors or a key derived therefrom against one or more corresponding stored values; and applying the following rules:

when the one or more corresponding values match the plurality of authentication factors or a key derived therefrom, the vehicle or a vehicle occupant thereof is authenticated successfully and a transaction between the vehicle and remote server is enabled; and when the one or more corresponding values do not match the plurality of authentication factors or a key derived therefrom, the vehicle or a vehicle occupant thereof is not authenticated successfully and the transaction between the vehicle and remote server is not enabled.

20. The method of claim 19, wherein the remote server receives the key derived from the plurality of authentication factors, wherein the key is derived using the plurality of authentication factors as a seed value, wherein the key is an authentication key, benign key, content-encryption key, crypto ignition key, cryptovariable, derived key, electronic key, ephemeral key, key encryption key, key production key, master key, master encryption key, public/private key, session key, symmetric key, asymmetric key, traffic encryption key, transmission security key, seed key, signature key, or stream key, and wherein the key is derived using a key derivation function, keystream generator, cryptographic hash function, key derivation function, cryptographic pseudorandom number generator, cryptanalytic algorithm, broken cryptography algorithm, asymmetric key algorithm, information-theoretically secure algorithm, integer factorization algorithm, symmetric key algorithm, Type 1, 2, or 2 3 encryption algorithm, advanced access content system, or cipher block chain.

21. The method of claim 19, wherein the transaction is a licensing validity check by a vendor, wherein the plurality of authentication factors comprise a wireless remote signal description emitted by a keyless remote, wherein the keyless remote comprises a short range radio transmitter emitting the wireless remote signal, and wherein the keyless remote transmits the wireless remote signal as a coded signal by radio waves to a receiver in the vehicle.

22. The method of claim 19, wherein the transaction is a purchase of a good or service by the vehicle occupant, wherein the plurality of authentication factors comprise a passcode received by a receiver in the vehicle from the remote server, wherein the passcode deletes automatically a passcode stored in the computer readable medium and previously used by the occupant, and wherein, if the received passcode is not entered within a specified time limit, the remote server automatically sends a new passcode to the vehicle receiver.

23. The method of claim 19, wherein the plurality of authentication factors comprise a sensed dynamically changing vehicle parameter, wherein the sensed vehicle parameter is one or more of vehicle location, vehicle speed, acceleration, stored energy or fuel level, winding temperature, rotor speed, battery pack voltage level, output electrical current, electrical current direction of flow, leakage current, battery pack temperature, state-of-charge, state-of-health or state-of-function, throttle position, manifold pressure, engine coolant temperature, mass air flow, camshaft position, crankshaft position, oxygen, detonation, EGR, intake air temperature, engine speed, brake pedal position, accelerator pedal position, brake pad wear, or fuel pressure, and wherein the plurality of sensors comprise one or more of a throttle or accelerator pedal position sensor, a brake pedal position sensor, manifold pressure sensor, engine coolant temperature sensor, mass air flow sensor, camshaft position sensor, crankshaft position sensor, pedal angle sensor, chassis position sensor, oxygen sensor, AC or DC current sensor, brake pad wear sensor, detonation sensor, EGR sensor, satellite position system unit, or intake air temperature sensor to collect the sensed vehicle parameter.

24. The method of claim 19, wherein the plurality of authentication factors comprise a sensed dynamically changing environmental parameter, wherein the sensed environmental parameter is associated with an interior or exterior of the vehicle, wherein the sensed environmental parameter is one or more of light level, still or video image, and sound signature of ambient noise, and wherein the plurality of sensors comprise one or more of a light sensor, still or video image by an image capture device, or a microphone to collect the sensed environmental parameter.

\* \* \* \* \*

UNITED STATES PATENT AND TRADEMARK OFFICE
CERTIFICATE OF CORRECTION

PATENT NO. : 9,984,522 B2
APPLICATION NO. : 15/339599
DATED : May 29, 2018
INVENTOR(S) : Ricci Page 1 of 1

It is certified that error appears in the above-identified patent and that said Letters Patent is hereby corrected as shown below:

Claim 8, Column 42, Line 37, the ":" before "leakage" should be deleted.
Claim 8, Column 42, Lines 46-47, "engine coolant, temperature sensor" should be changed to --engine coolant temperature sensor--.
Claim 17, Column 44, Line 38, "EGF sensor" should be changed to --EGR sensor--.
Claim 23, Column 46, Line 15, insert a --,-- after "state-of-health".

Signed and Sealed this
Second Day of October, 2018

Andrei Iancu
*Director of the United States Patent and Trademark Office*